(12) United States Patent
Murphy et al.

(10) Patent No.: US 9,708,635 B2
(45) Date of Patent: *Jul. 18, 2017

(54) METHODS OF MAKING A NUCLEIC ACID ENCODING A HUMAN VARIABLE REGION

(71) Applicant: Regeneron Pharmaceuticals, Inc., Tarrytown, NY (US)

(72) Inventors: Andrew J. Murphy, Croton-On-Hudson, NY (US); George D. Yancopoulos, Yorktown Heights, NY (US); Margaret Karow, Santa Rosa Valley, CA (US); Lynn Macdonald, White Plains, NY (US); Sean Stevens, San Diego, CA (US); Aris N. Economides, Tarrytown, NY (US); David M. Valenzuela, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/719,819

(22) Filed: Dec. 19, 2012

(65) Prior Publication Data

US 2013/0210137 A1 Aug. 15, 2013

Related U.S. Application Data

(60) Continuation of application No. 13/154,976, filed on Jun. 7, 2011, which is a continuation of application No. 11/595,427, filed on Nov. 9, 2006, which is a continuation of application No. 10/624,044, filed on Jul. 21, 2003, now abandoned, which is a division of application No. 09/784,859, filed on Feb. 16, 2001, now Pat. No. 6,596,541, which is a continuation-in-part of application No. 09/732,234, filed on Dec. 7, 2000, now Pat. No. 6,856,251.

(60) Provisional application No. 60/244,665, filed on Oct. 31, 2000.

(51) Int. Cl.

| | |
|---|---|
| A01K 67/027 | (2006.01) |
| C07K 16/00 | (2006.01) |
| C07K 16/46 | (2006.01) |
| C12N 15/90 | (2006.01) |
| C12P 21/00 | (2006.01) |
| C12N 15/67 | (2006.01) |
| C12N 15/85 | (2006.01) |
| C07K 16/28 | (2006.01) |

(52) U.S. Cl.
CPC .......... *C12P 21/00* (2013.01); *A01K 67/0275* (2013.01); *A01K 67/0278* (2013.01); *C07K 16/00* (2013.01); *C07K 16/28* (2013.01); *C07K 16/462* (2013.01); *C12N 15/67* (2013.01); *C12N 15/85* (2013.01); *C12N 15/8509* (2013.01); *C12N 15/902* (2013.01); *C12N 15/907* (2013.01); *A01K 2207/15* (2013.01); *A01K 2217/05* (2013.01); *A01K 2227/105* (2013.01); *A01K 2267/01* (2013.01); *C07K 2317/10* (2013.01); *C07K 2317/21* (2013.01); *C07K 2317/24* (2013.01); *C07K 2317/51* (2013.01); *C07K 2317/515* (2013.01); *C07K 2317/56* (2013.01); *C12N 2800/204* (2013.01)

(58) Field of Classification Search
CPC ............ A01K 67/0278; A01K 67/0275; A01K 2227/105; A01K 2267/01; A01K 2207/15; A01K 2227/10; C07K 16/00; C07K 16/462; C12N 15/85; C12N 15/907; C12N 15/902; C12N 2800/30; A61K 49/00

See application file for complete search history.

(56) References Cited

U.S. PATENT DOCUMENTS

| | | | |
|---|---|---|---|
| 5,202,238 A | 4/1993 | Fell, Jr. et al. | |
| 5,436,149 A | 7/1995 | Barnes | |
| 5,545,807 A * | 8/1996 | Surani et al. | 800/6 |
| 5,614,396 A | 3/1997 | Bradley et al. | |
| 5,625,126 A * | 4/1997 | Lonberg et al. | 800/18 |
| 5,770,429 A | 6/1998 | Lonberg et al. | |
| 5,789,215 A | 8/1998 | Berns et al. | |

(Continued)

FOREIGN PATENT DOCUMENTS

| | | |
|---|---|---|
| EP | 438 474 A1 | 7/1991 |
| EP | 1 204 740 B1 | 5/2002 |

(Continued)

OTHER PUBLICATIONS

Clark et al (Nature Reviews: Genetics. 2003, 825-833.*

(Continued)

*Primary Examiner* — Anoop Singh
(74) *Attorney, Agent, or Firm* — Brendan T. Jones; Neil Miyamoto; Foley Hoag LLP

(57) ABSTRACT

A method for engineering and utilizing large DNA vectors to target, via homologous recombination, and modify, in any desirable fashion, endogenous genes and chromosomal loci in eukaryotic cells. These large DNA targeting vectors for eukaryotic cells, termed LTVECs, are derived from fragments of cloned genomic DNA larger than those typically used by other approaches intended to perform homologous targeting in eukaryotic cells. Also provided is a rapid and convenient method of detecting eukaryotic cells in which the LTVEC has correctly targeted and modified the desired endogenous gene(s) or chromosomal locus (loci) as well as the use of these cells to generate organisms bearing the genetic modification.

10 Claims, 7 Drawing Sheets

(56) References Cited

U.S. PATENT DOCUMENTS

| | | | |
|---|---|---|---|
| 5,877,397 A | 3/1999 | Lonberg et al. | |
| 5,928,914 A | 7/1999 | Leboulch et al. | |
| 5,939,598 A | 8/1999 | Kucherlapati et al. | |
| 5,942,435 A | 8/1999 | Wheeler | |
| 6,069,010 A | 5/2000 | Choi | |
| 6,075,181 A | 6/2000 | Kucherlapati et al. | |
| 6,096,878 A | 8/2000 | Honjo et al. | |
| 6,114,598 A * | 9/2000 | Kucherlapati | A01K 67/0275 435/325 |
| 6,130,364 A | 10/2000 | Jakobovits et al. | |
| 6,331,415 B1 | 12/2001 | Cabilly et al. | |
| 6,528,313 B1 | 3/2003 | Le Mouellic et al. | |
| 6,570,061 B1 | 5/2003 | Rajewsky et al. | |
| 6,586,251 B2 | 7/2003 | Economides et al. | |
| 6,596,541 B2 | 7/2003 | Murphy et al. | |
| 6,638,768 B1 | 10/2003 | Le Mouellic et al. | |
| 6,653,113 B1 | 11/2003 | Berns et al. | |
| 6,673,986 B1 | 1/2004 | Kucherlapati et al. | |
| 6,833,268 B1 | 12/2004 | Green et al. | |
| 6,998,514 B2 | 2/2006 | Bruggemann | |
| 7,105,348 B2 | 9/2006 | Murphy et al. | |
| 7,129,084 B2 | 10/2006 | Buelow et al. | |
| 7,145,056 B2 | 12/2006 | Jakobovits et al. | |
| 7,435,871 B2 | 10/2008 | Green et al. | |
| 7,501,552 B2 | 3/2009 | Lonberg et al. | |
| 8,759,105 B2 | 6/2014 | Economides et al. | |
| 8,791,323 B2 | 7/2014 | Murphy et al. | |
| 9,012,717 B2 | 4/2015 | Macdonald et al. | |
| 2002/0028488 A1 | 3/2002 | Singh et al. | |
| 2002/0178456 A1 | 11/2002 | Buelow | |
| 2003/0182675 A1 | 9/2003 | Etches et al. | |
| 2004/0018626 A1 | 1/2004 | Murphy et al. | |
| 2004/0158880 A1 | 8/2004 | Buelow et al. | |
| 2005/0054055 A1 | 3/2005 | Kucherlapati et al. | |
| 2005/0144655 A1 | 6/2005 | Economides et al. | |
| 2005/0153392 A1 | 7/2005 | Buelow et al. | |
| 2006/0015957 A1* | 1/2006 | Lonberg et al. | 800/18 |
| 2006/0026696 A1 | 2/2006 | Buelow et al. | |
| 2006/0026703 A1 | 2/2006 | Lonberg et al. | |
| 2006/0040363 A1 | 2/2006 | Kucherlapati et al. | |
| 2007/0280945 A1 | 12/2007 | Stevens et al. | |
| 2011/0258710 A1 | 10/2011 | Murphy et al. | |
| 2013/0137101 A1 | 5/2013 | Economides et al. | |
| 2013/0254911 A1 | 9/2013 | Macdonald et al. | |
| 2014/0178879 A1 | 6/2014 | Economides et al. | |

FOREIGN PATENT DOCUMENTS

| | | |
|---|---|---|
| EP | 1399575 A2 | 3/2004 |
| JP | 3068507 B2 | 7/2000 |
| WO | WO-90/04036 A1 | 4/1990 |
| WO | WO-91/00906 A1 | 1/1991 |
| WO | WO-93/04169 A1 | 3/1993 |
| WO | WO-94/02602 A1 | 2/1994 |
| WO | WO-94/04667 A1 | 3/1994 |
| WO | WO-94/25585 A1 | 11/1994 |
| WO | WO-96/30498 A1 | 10/1996 |
| WO | WO-98/24893 A2 | 6/1998 |
| WO | WO-99/45962 A1 | 9/1999 |
| WO | WO-01/19394 A2 | 3/2001 |
| WO | WO-02/12437 A2 | 2/2002 |
| WO | WO-02/36789 A2 | 5/2002 |
| WO | WO-02/066630 A1 | 8/2002 |
| WO | WO-03/047336 A2 | 6/2003 |
| WO | WO-03/081993 A2 | 10/2003 |
| WO | WO-2006/068953 A2 | 6/2006 |
| WO | WO-2008/054606 A2 | 5/2008 |
| WO | WO-2008/076379 A2 | 6/2008 |
| WO | WO-2009/018411 A1 | 2/2009 |
| WO | WO-2009/023540 A1 | 2/2009 |
| WO | WO-2011/014469 A1 | 2/2011 |
| WO | WO-2011/097603 A1 | 8/2011 |
| WO | WO-2011/163311 A1 | 12/2011 |
| WO | WO-2012/141798 A1 | 10/2012 |
| WO | WO-2014/071397 A2 | 5/2014 |
| WO | WO-2015/088643 A1 | 6/2015 |
| WO | WO-2016/081923 A2 | 5/2016 |

OTHER PUBLICATIONS

Niemann et al (Rev. Sci, Tech. Off. Int. Spiz. 2005, (24), 285-298.*
Ristevski et al Molecular Biotechnology, 2005, 153-163.*
Gama Sosa et al (Brain Struct Funct, 2010, 214:91-109.*
Smith Journal of Biotechnology 99 (2002) 1-22.*
Qi et al Hypertension. 2005, 45:1004-1011.*
Parng, The Journal of Immunology, 1996, 157: 5478-5486.*
Kaushik, Veterinary Immunology and irnmunopathology 87 (2002) 347-350.*
Wagner et al Abstract Nucleic Acids Res. 1994; 22(8):1389-93.*
Butler Rev Scientifique et Technique Office International Des Epizooties. 1998, 17, 1, 43-70.*
Sen and Baltimore Cell, 1986, 46, 705-716).*
Hochepied et al Stem Cells, 2004, 22: 441-447.*
Schoonjans et al Stem Cells, 2003, 21: 90-97.*
Anna B. Auerbach, Acta Biochimica Polonica , 2004, 51 :9-31.*
Pera Journal of Cell Science 113:5-10, 2000.*
Sen and Baltimore, Cell, 1986, 705-716.*
Taki et al Science, 1993: 262, 5137,. 1268-127I.*
Cox et al Trends in Biotechnology vol. 19 No. 7 Jul. 2001, 247-250.*
Pawlitzsky et al The Journal of Immunology, 2006, 176: 6839-6851.*
Johnston et al The Journal of Immunology, 2006, 176: 4221-4234.*
Ebert et al (Immunity, 2011, 25; 34(2):175-87.*
Hewitt et al Nature Immunology, 2008, 9(4), 396-404.*
NCBI accession No. AF477986.1, Feb. 2012, pp. 1-2.*
Retter et al The Journal of Immunology, 2007, 179: 2419-2427.*
Sheng et al, Nucleic Acid Research, 1995, 23, 1990-1996.*
Zhang, et al., Nat Genet, 20:123-8, 1998.*
Hill et al., Genomics, 64:111-3, 2000.*
Sen and Baltimore, Cell, 1986, see p. 705-716.*
Taki et al (Science, 1993: 262, 5137,. 1268-127I.*
Pawlitzsky et al (The Journal of Immunology, 2006, 176: 6839-6851.*
MacDonald et al, PNAS, 2010, 111, 5147-5152.*
Angrand, P.O. et al., "Simplified Generation of Targeting Constructs Using ET Recombination," Nucleic Acids Res., 27(17): e16 (1999).
Cheng, S. et al., "Long PCR," Nature 369(6482):684-685 (1994).
Deng, C. et al., "Reexamination of Gene Targeting Frequency as a Function of the Extent of Homology Between the Targeting Vector and the Target Focus," Mol. Cell. Biol. 12(8):3365-3371 (1992).
Durdik, J. et al., "Isotype Switching by a Microinjected mu Immunoglobulin Heavy Chain Gene in Transgenic Mice," Proc. Natl. Acad. Sci. USA 86(7):2346-2350 (1989).
Fishwild, D.M. et al., "High-Avidity Human IgGkappa Monoclonal Antibodies From a Novel Strain of Minilocus Transgenic Mice," Nat. Biotechnol. 14(7):845-851 (1996).
Foord, O.S. et al., "Long-Distance PCR," PCR Methods Appl. 3(6):S149-S161 (1994).
Forozan, F. et al., "Genome Screening by Comparative Genomic Hybridization," Trends Genet. 13(10:405-409 (1997).
Gerstein, R.M. et al., "Isotype Switching of an Immunoglobulin Heavy Chain Transgene Occurs by DNA Recombination Between Different Chromosomes," Cell, 63(3):537-548 (1990).
Herault, Y. et al., "Engineering Chromosomes in Mice Through Targeting Meiotic Recombination (Tamere)," Nat. Genet., 20(4):381-384 (1998).
Hill, F. et al., "BAC Trimming: Minimizing Clone Overlaps," Genomics, 64(1):111-113 (2000).
Houldsworth, J. et al., "Comparative Genomic Hybridization: An Overview," Am. J. Pathol. 145(6): 1253-1260 (1994).
Kawasaki, K. et al., "One-Megabase Sequence Analysis of the Human Immunoglobulin λ Gene Locus," Genome Research, 7:250-261 (1997).

(56) References Cited

OTHER PUBLICATIONS

Laan, M et al., "Solid-Phase Minisequencing Confirmed by FISH Analysis in Determination of Gene Copy Number," Hum. Genet. 96(3):275-280 (1995).
Lie, Y.S. et al., "Advances in Quantitative PCR Technology: 5' Nuclease Assays," Curr. Opin. Biotechnol., 9(1):43-48 (1998).
Lizardi, P.M. et al., "Mutation Detection and Single-molecule Counting Using Isothermal Rolling Circle Amplification," Nat. Genet. 19(3):225-232 (1998).
Mitra, R.D. et al., "In Situ Localized Amplification and Contact Replication of Many Individual DNA Molecules," Nucleic Acis Res., 27(24):e34 (1999).
Muyrers, J.P. et al., "Rapid Modfication of Bacterial Artificial Chromosomes by ET-Recombination," Nucelic Acids Res., 27(6):1555-1557 (1999).
Ponce, M.R. et al., "PCR Amplification of Long DNA Fragments," Nucleic Acids Res., 20(3):623 (1992).
Popov, A.V. et al., "Assembly and Extension of Yeast Artificial Chromosome Large Locus," Gene, 177(1-2):195-201 (1996).
Scott, C.T., "Mice with a Human Touch," Nat. Biotech., 25(10):1075-1077 (2007).
Smithies, O. et al., "Insertion of DNA Sequences into the Human Chromosomal Beta-Globin Locus by Homologous Recombination," Nature, 317(6034):230-234 (2007).
Tan, W. et al., "Molecular Beacons: a Novel DNA Probe for Nucleic Acid and Protein Studies," Eur. J. Chem., 6(7):1107-1111 (2000).
Taylor, L.D., "Human Immunoglobulin Transgenes Undergo Rearrangement, Somatic Mutation and Class Switching in Mice That Lock Endogenous IgM," Int. Immunol. 6(4):579-591 (1994).
Thomas, K.R. et al., "Site-directed Mutagenesis by Gene Targeting in Mouse Embryo-Derived Stem Cells," Cell, 51(3):503-512 (1987).
Thompson, C.T et al., "Cytogenetic Profiling Using Fluorescence in Situ Hybridization (FISH) and Comparative Genomic Hybridization (CGH)," J. Cell. Biochem. Suppl., 17G:139-143 (1993).
Tomizuka, K. et al., "Double Trans-Chromosomic Mice: Maintenance of Two Indivudual Human Chromosome Fragments Containing Ig Heavy and Kappa Loci and Expression of Fully Human Antibodies," Proc. Natl. Acad. Sci. USA., 97(2):722-727 (2000).
Yang, X.W. et al., "Homologous Recombination Based Modification in*Escherichia coli* and Germline Transmission in Transgenic Mice of a Bacterial Artificial Chromosome," Nat. Biotechnol., 15(9):859-865 (1997).
Yu, D. et al., "An Efficient Recombination System for Chromosome Engineering in *Escherichia coli*," Proc. Natl. Acad. Sci. USA, 97(11):5978-5983 (2000).
Zhang, Y. et al., "A New Logic for DNA Engineering Using Recombination in *Escherichia coli*," Nat. Genet., 20(2):123-128 (1998).
Chapter 1: Gene Targeting, Principles, and Practice in Mammalian Cells, Gene Targeting —A Practical Approach, 2nd Ed. Edited by Joyner AL, Hasty P. et al., pp. 1-35 (2000).
Butler, Revue Scientifique at Technique Office International Des Epizooties, 17(1):43-70 (1998).
Soukharev, S. et al., "Segmental Genomic Replacement in Embryonic Stem Cells by Double lox Targeting," Nucleic Acids Res., 27(18):e21 (1999).
Clark, M., "Antibody Humanization: A Case of the 'Emperor's New Clothes'?", Immunol. Today 21(8):397-402 (2000).
Jensen, M. et al., "One Step Generation of Fully Chimeric Antibodies Using Cgamma1- and Ckappa Mutant Mice," J. Immunother., 30(3):338-349 (2007).
Hochepied, T. et al., "Breaking the Species Barrier: Deprivation of Germline-Competent Embryonic Stem Cells from Musspretus x C57BL/6 Hybrids," Stem Cells, 22(4):441-447 (2004).
Schoonjans, L. et al., "Improved Generation of Germline-Competent Embryonic Stem Cell Lines from Inbred Mouse Strains," Stem Cells, 21(1):90-97 (2003).

Bogen, B. et al., "A Rearranged λ2 Light Gene Chain Retards But Does Not Exclude χ and λ1 Expression." Eur. J. Immunol., 21:2391-2395 (1991).
Bruggemann, M. "Human Antibody Expression in Transgenic Mice," Archivum Immunologiae et Therapiae Experimentalis, 49:203-208 (2001).
Bruggemann, M. et al., "Strategies for Expressing Human Antibody Repertoires in Transgenic Mice," Review Immunology Today, 17(8):391-397 (1996).
Davies, N.P. et al., "Creation of Mice Expressing Human Activity Light Chains by Introduction of a Yeast Artificial Chromosome Containing the Core Region of the Human Immunoglobulin κ Locus." Bio/Technology, 11:911-914 (1993).
Gu, H. et al., "Independent Control of Immunoglobulin Switch Recombination at Individual Switch Regions Evidenced through Cre-loxP-Mediated Gene Targeting," Cell, 73:1155-1164 (1993).
Jessen, J.R. et al., "Modification of Bacterial Artificial Chromosomes Through Chi-stimulated Homologous Recombination and its Application in Zebrafish Transgenesis," Proc. Natl. Acad. Sci, USA, 95:5121-5126 (1998).
Lefranc, M.-P., "Nomenclature of the Human Immunoglobulin Lambda (IGL) Genes," Exp. Clin. Immunogenet., 18:242-254 (2001).
Lefranc, M.-P., "Nomenclature of the Human Immunoglobulin Heavy (IGH) Genes," Exp. Clin. Immunogenet., 18:100-116 (2001).
Mendez, M.J. et al., "Functional Transplant of Megabase Human Immunoglobulin Loci Recapitulates Human Antibody Response in Mice," Nature Genetics, 15:146-156 (1997).
Narayanan, K. et al., "Efficient and Precise Engineering of a 200 kb β-*globin* Human/Bacterial Artificial Chromosome in *E. coli* DH10B Using an Inducible Homologous Recombination System." Gene Therapy, 6:442-447 (1999).
Neuberger, M.S. et al., "Isotype Exclusion and Transgene Down-Regulation in Immunoglobulin-λ Transgenic Mice," Nature 338:350-363 (1989).
Schlake, T. et al., "Use of Mutated FLP Recognition Target (FRT) Sites for the Exchange of Expression Cassettes at Defined Chromosomal Loci," Biochemistry, 33:12746-12751 (1994).
Shi, Y.-P. et al., "The Mapping of Transgenes by Fluorescence in situ Hybridization on G-banded Mouse Chromosomes," Mammalian Genome, 5:337-341 (1994).
Smith, D.R. et al., "Genomic Analysis of Transgenic Animals," Methods Mol. Biol. 18:323-327 (1993).
Takada, S. et al., "Construction of Chimaeric Processed Immunoglobulin Genes Containing Mouse Variable and Human Constant Region Sequences," Nature, 314:452-454 (1985).
Taki, S. et al., "Targeted Insertion of a Variable Region Gene into the Immunoglobulin Heavy Chain Locus," Science, 262:1268-1271 (1993).
Thykjaer, T. et al., "Gene Targeting Approaches Using Positive-negative Selection and Large Flanking Regions," Plant Molecular Biology, 35:523-530 (1997).
Waterhouse, P. et al., "Combinatorial Infection and in Vivo Recombination: A strategy for Making Large Phage Antibody Repertoires," Nucleic Acids Research, 21(9):2265-2266 (1993).
Wilke, K. et al., "Diagnosis of Haploidy and Triploidy Based on Measurement of Gene Copy Number By Real-Time PCR," Human Mutation 16:431-436 (2000).
Zou, R.-Y. et al., "Cre-loxP-Mediated Gene Replacement: A Mouse Strain Producing Humanized Antibodies," Current Biology, 4:1099-1103 (1994).
Altenburger, W. et al., "DNA Sequence of the Constant Gene Region of the Mouse Immunoglobulin Kappa Chain," Nucleic Acids Research, 9(4):971-981 (1981).
Auerbach, A. B. et al., "Production of Functional Transgenic Mice by DNA Pronuclear Microinjection," Acta Biochimica Polonia, 51(1):9-31 (2004).
Baker, A.M. et al., "Adaptation of TCR Expression Vectors for the Construction of Mouse-Human Chimeric MBP-Specific TCR Transgenes," Journal of Neuroscience Research, 45:487-491 (1996).

(56) References Cited

OTHER PUBLICATIONS

Blomberg, B. et al., "Organization of Four Mouse Lambda Light Chain Immunoglobulin Genes," Proc. Natl. Acad. Sci. USA, 78(6):3765-3769 (1981).
Bouhassira, E.E. et al., "Transcriptional Behavior of LCR Enhancer Elements Integrated at the Same Chromosomal Locus by Recombinase-Mediated Cassette Exchange," Blood, 90(9):3332-3344 (1997).
Brüggemann, M. et al., "Immunoglobulin Heavy Chain Locus of the Rat: Striking Homology to Mouse Antibody Genes," Proc. Natl. Acad. Sci. USA, 83:6075-6079 (1986).
Brüggemann, M., Molecular Biology of B Cells:"Chapter 34—Human Monoclonal Antibodies from Translocu Mice," pp. 547-561 (2003).
Clark, J. et al., "A Future for Transgenic Livestock," Nature Reviews, 4:825-833 (2003).
de Bono, B. et al., "$V_H$ Gene Segments in the Mouse and Human Genomes," J. Mol. Biol., 342:131-143 (2004).
Devoy, A. et al., "Genomically Humanized Mice: Technologies and Promises," Nature, 13:14-20 (2012).
Featherstone, K. et al., "The Mouse Immunoglobulin Heavy Chain V-D Intergenic Sequence Contains Insulators That May Regulate Ordered V(D)J Recombination," J. of Biol. Chem., 285(13):9327-9338 (2010).
Feng, Y.Q. et al., "Site-specific Chromosomal Integration in Mammalian Cells: Highly Efficient CRE Recombinase-mediated Cassette Exchange," J. Mol. Biol., 292:779-785 (1999).
Fleischer, B. et al., "Infection and Immunity: Reactivity of Mouse T-cell Hybridomas Expressing Human Vbeta Gene Segments with *Staphylococcal* and *Streptococcal* Superantigens," Infect. Immun., 64(3):987-994 (1996).
Frengen, E. et al., "Modular Bacterial Artificial Chromosome Vectors for Transfer of Large Inserts into Mammalian Cells," Genomics, 68:118-126 (2000).
Gama Sosa, M.A. et al., "Animal Transgenesis: An Overview," Brain Struct Funct, 214:91-109 (2010).
Ganten, D. et al., "Species Specificity of Renin Kinetics in Transgenic Rats Harboring the Human Renin and Angiotensinogen Genes," Proc. Natl. Acad. Sci. USA, 89:7806-7810 (1992).
Giraldo, P. et al., "Size Matters: Use of YACs, BACs, and PACs in Transgenic Animals," Transgenic Research, 10:83-103 (2001).
Glanville, J. et al., "Naive Antibody Gene-Segment Frequencies are Heritable and Unaltered by Chronic Lymphocyte Ablation," PNAS, 108(50):20066-20071 (2011).
Green, L. L. et al., Regulation of B Cell Development by Variable Gene Complexity in Mice Reconstituted with Human Immunoglobulin Yeast Artificial Chromosomes, J. Exp. Med., 188(3):483-495 (1998).
Green, L. L., Antibody Engineering via Genetic Engineering of the Mouse: XenoMouse Strains are a Vehicle for the Facile Generation of Therapeutic Human Monoclonal Antibodies, J. of Immun. Meth., 231:11-23 (1999).
Green, L.L. et al., "Antigen-specific Human Monocolonal Antibodies from Mice Engineered with Human Ig Heavy and Light Chain YACs," Nature Genetics, 7:13-21 (1994).
Han, C. et al., "Comprehensive Analysis of Reproductive ADAMs: Relationship of ADAM4 and ADAM6 with an ADAM Complex Required for Fertilization in Mice," Biology of Reproduction, 80:1001-1008 (2009).
Hansen, S. et al., "Crescendo's Cash Fragments," BioCentury, The Bernstein Report on BioBusiness, Dec. 23, 2013, p. A13.
Hewitt, S. I. et al., "Association Between the *Igk* and *Igh* Immunoglobulin loci Mediated by the 3' *Igk* Enhancer Induces 'decontraction' of the *Igh* Locus in Pre-B Cells," Nature Immunology, 9(4):396-404 (2008).
Iannaccone, P. M. et al., "Rapid Communication: Pluripotent Embryonic Stem Cells from the Rat are Capable of Producing Chimeras," Developmental Biology, 163:288-292 (1994).
Jakobovits, A. et al., "Production of Transgenic Mice with Yeast Artificial Chromosomes," Methods in Molecular Biology, 136:435-453 (2000).
Jakobovits, A., "Humanizing the Mouse Genome," Current Biology, 4(8):761-763 (1994).
Jakobovits, A., "Production of Fully Human Antibodies by Transgenic Mice," Current Opinion in Biotechnology, 6:561-566 (1995).
Kaushik, A. et al., "Novel Insight into Antibody Diversification from Cattle," Veterinary Immun. and Immuno., 87:347-350 (2002).
Kolb, A.F. et al., "Insertion of a Foreign Gene into the β-casein Locus by Cre-mediated Site-Specific Recombination," Gene, 227:21-31 (1999).
Kouskoff, V. et al., "Cassette Vectors Directing Expression of T Cell Receptor Genes in Transgenic Mice," J. of Immun. Methods, 180:273-280 (1995).
Ma, B. et al., "Human Antibody Expression in Transgenic Rats: Comparison of Chimeric IgH Loci with Human $V_H$, D and $J_H$ but Bearing Different Rat C-gene Regions," J. Immunol. Methods, (2013).
Macdonald, L.E. et al., "Precise and in situ Genetic Humanization of 6 Mb of Mouse Immunoglobulin Genes," PNAS, 111(14):5147-5152 (2014).
Matsuda, F. et al., "The Complete Nucleotide Sequence of the Human Immunoglobulin Heavy Chain Variable Region Locus," J. Exp. Med. 188(11):2151-2162 (1998).
Monaco, A.P. et al., "YACs, BACs, PACs and MACs: Artificial Chromosomes as Research Tools," TIBTECH, 12:280-286 (1994).
Murphy, A., "VelocImmune: Immunoglobulin Variable Region Humanized Mice," pp. 100-107 (2009).
Murphy, A.J. et al., "Mice with Megabase Humanization of their Immunoglobulin Genes Generate Antibodies as Efficiently as Normal Mice," PNAS, 111(14):5153-5158 (2014).
Müller, U., "Ten Years of Gene Targeting: Targeted Mouse Mutants, from Vector Design to Phenotype Analysis," Mech. of Dev., 82:3-21 (1999).
Niemann, H. et al., "Transgenic Farm Animals: Present and Future," Rev. Sci. Tech. Off. Int. Spiz., 24:285-298 (2005).
Osoegawa, K. et al., "An Improved Approach for Construction of Bacterial Artificial Chromosome Libraries," Genomics, 52:1-8 (1998).
Parng, C-L. et al., "Gene Conversion Contributes to Ig Light Chain Diversity in Cattle," The J. of Immun., 157:5478-5486 (1996).
Presentation by George D. Yancopoulos, M.D., Ph.D. dated May 13, 2013.
Qi, N. R. et al., "A New Transgenic Rat Model of Hepatic Steatosis and the Metabolic Syndrome," Hypertension, 45:1004-1011 (2005).
Ravetch, J.V. et al., "Evolutionary Approach to the Question of Immunoglobulin Heavy Chain Switching: Evidence from Cloned Human and Mouse Genes," Proc. Natl. Acad. Sci. USA, 77(11):6734-6738 (1980).
*Regeneron Pharmaceuticals, Inc.* v. *ABLEXIS LLC*, Complaint for Patent Infringement dated Mar. 5, 2014.
*Regeneron Pharmaceuticals, Inc.* v. *KYMAB LIMITED*, Amended Defence and Counterclaim dated Apr. 17, 2014.
*Regeneron Pharmaceuticals, Inc.* v. *KYMAB LIMITED*, Amended Particulars of Infringement dated Apr. 1, 2014. pp. 1-13.
*Regeneron Pharmaceuticals, Inc.* v. *MERUS B.V.*, Complaint for Patent Infringement dated Mar. 5, 2014.
*Regeneron Pharmaceuticals, Inc.* v. *NOVO NORDISK A/S* (a company established under the laws of the Kingdom of Denmark) Particulars of Infringement dated Jan. 3, 2014.
*Regeneron Pharmaceuticals, Inc.* v. *NOVO NORDISK A/S*, Defence and Counterclaim dated Mar. 27, 2014.
Ristevski, S. et al., "Making Better Transgenic Models," Molecular Biotechnology, 29:153-163 (2005).
Ronai, D. et al., "Variegated Expression of the Endogenous Immunoglobulin Heavy-Chain Gene in the Absence of the Intronic Locus Control Region," Mol. Cell. Biol., 19(10):7031-7039 (1999).
Schäble, K.F. et al., "The Variable Genes of the Human Immunoglobulin א Locus," Biol. Chem. Hoppe-Seyler, 374:1001-1022 (1993).

(56) References Cited

OTHER PUBLICATIONS

Sen, R. et al., "Multiple Nuclear Factors Interact with the Immunoglobulin Enhancer Sequences," Reprinted from Cell, 46:705-716 (1986).
Shah, R. et al., "Stable Transfection of Rat Preproinsulin H Gene Into Rat Hematopoietic Stem Cells via Recombinant Adeno-Associated Virus," Life Sciences, 65(20):2041-2047 (1999).
Shimizu, A. et al., "Organization of the Constant-Region Gene Family of the Mouse Immunoglobulin Heavy Chain," Cell, 28:499-506 (1982).
Shizuya, H. et al., "Cloning and Stable Maintenance of 300-kilobase-pair Fragments of Human DNA in *Escherichia Coli* using an F-factor-based Vector," Proc. Natl, Acad. Sci. USA, 89:8794-8797 (1992).
Smith, K.R. et al., "Gene Transfer in Higher Animals: Theoretical Considerations and Key Concepts," J. of Biotechnology, 99:1-22 (2002).
Statement of Andrew Murphy dated Jan. 27, 2014.
Statement of Sue Klapholz, M.D., Ph.D. dated Jan. 27, 2014.
Susulic, V.S. et al., "Targeted Disruption of the β3-Adrenergic Receiptor Gene," The Journal of Biological Chemistry, 270(49):29483-29492 (1995).
Tan, K.T. et al., "A Human-Mouse Chimeric Immunoglobulin Gene with a Human Variable Region is Expressed in Mouse Myeloma Cells," The Journal of Immunology, 135(5):3564-3567 (1985).
Valenzuela, D.M. et al., "High-throughput Engineering of the Mouse Genome Couples with High-Resolution Expression Analysis," Nature Biotechnology, 21(6):652-659 (2003).
Vollmer, J. et al., "Antigen Contacts by Ni-reactive TCR:αβ typical Chain Cooperation Versus α Chain-Dominated Specificity," International Immunology, 12(12):1723-1731 (2000).
Wagner, S.D. et al., "Antibodies Generated from Human Immunoglobulin Miniloci in Transgenic Mice," Nucleic Acids Research, 22(8):1389-1393 (1994).
Yang, X.W. et al., "Homologous Recombination Based Modification in *Esherichia Coli* and Germline Transmission in Transgenic Mice of a Bacterial Artificial Chromsome," Nature Biotechnology, 15:859-865 (1997).
Decision of Technical Board Appeal for EP 1360287, published Mar. 10, 2016.
Approved Judgment of *Regeneron Pharmaceuticals* vs. *Kymab Limited*, published Feb. 1, 2016.
*Regeneron Pharmaceuticals, Inc.* v. *Merus B.V.*, Brief for Appellant Regeneron Pharmaceuticals, Inc. dated Feb. 16, 2016.
*Regeneron Pharmaceuticals, Inc.* v. *Merus B.V.*, Brief for Defendant-Appellee [Non-Confidential] dated Apr. 14, 2016.
Abuin et al., "Recycling selectable markers in mouse embryonic stem cells," Mol Cell Biol, 16(4):1851-6 (1996).
Andrews declaration, document D59 from T1526/11, Feb. 2011.
Askew et al., "Site-directed point mutations in embryonic stem cells: a gene-targeting tag-and-exchange strategy," Mol Cell Biol, 13(7):4115-24 (1993).
Bagchi et al., "CHD5 is a tumor suppressor at human 1p36," Cell, 128(3):459-75 (2007).
Bolland et al., "Antisense intergenic transcription in V(D)J recombination," Nat Immunol, 5:630-7 (2004).
Bradley, "Embryonic stem cells: proliferation and differentiation," Curr Opin Cell Biol, 2(6):1013-7 (1990).
Cleary et al., "Disruption of an imprinted gene cluster by a targeted chromosomal translocation in mice," Nat Gen, 29(1):78-82 (2001).
Corcoran et al., "Impaired immunoglobulin gene rearrangement in mice lacking the IL-7 receptor," Nature, 391:904-7 (1998).
Corcoran et al., "The interleukin-7 receptor alpha chain transmits distinct signals for proliferation and differentiation during B lymphopoiesis," EMBO J, 15(8):1924-32 (1996).
Cvetkovic et al., "Appropriate tissue- and cell-specific expression of a single copy human angiotensinogen transgene specifically targeted upstream of the HPRT locus by homologous recombination," J Biol Chem, 275(2):1073-8 (2000).

Das et al., "Evolutionary dynamics of the immunoglobulin heavy chain variable region genes in vertebrates," Immunogenetics, 60(1):47-55 (2008).
Davis et al., "A null c-myc mutation causes lethiality before 10.5 days of gestation in homozygotes and reduced fertility in heterozygous female mice," Genes and Development, 7:671-82 (1993).
Decision of UK court regarding DX145 (D1), dated Sep. 7, 2015.
Declaration from Dr. Anne Corcoran.
Declaration from Professor Allan Bradley.
Declaration from Professor Francis Stewart.
Dr. Andrei Popov declaration, D53 from case T1526/11 (2009).
Ebert et al., "The distal VH gene cluster of the Igh locus contains distinct regulatory elements with pax5 transcription factor-dependent activity in pro-B cells," Immunity, 34:175-87 (2011).
Fedorov et al., "A comparison of the germline potential of differently aged ES cell lines and their transfected descendants," Transgenic Res, 6(3):223-31 (1997).
Haines et al., "Germline diversity of the expressed BALB/c VhJ558 gene family," Mol Immunol, 38:9-18 (2001).
Hansen et al., "Large-scale gene trapping in C57BL/6N mouse embryonic stem cells," Genome Research, 18(10):1670-9 (2008).
Huang et al., "Association of telomere length with authentic pluripotency of ES/iPS cells," Cell Research, 21(5):779-92 (2011).
Keane et al., "Mouse genomic variation and its effect on phenotypes and gene regulation," Nature, 477:289-294 (2011).
Kuehn, M.R. et al., "A potential animal model for Lesch-Nyham syndrome through introduction of HPRT mutations into mice," Nature, 326(6110):295-8 (1987).
Kuroiwa et al., "Sequential targeting of the genes encoding immunoglobulin-u and prion protein in cattle," Nature Genetics, 36(7):775-80 (2004).
Lee et al., "Complete humanization of the mouse immunoglobulin loci enables efficient therapeutic antibody discovery," Nature Biotechnol, 32(4):356-63 (2014).
Lewis et al., "A common human B globin splicing mutation modeled in mice," Blood, 91(6):2152-6 (1998).
Liang et al., "Extensive genomic copy number variation in embryonic stem cells," PNAS, 105(45):17453-6 (2008).
Little, M.—'Recombinant antibodies for immunotherapy' 2009, Cambridge University Press, New York, pp. 89-107.
Liu et al., "Embryonic lethality and tumorigenesis caused by segmental aneuploidy on mouse chromosome 11," Genetics, 150(3):1155-68 (1998).
Liu et al., "Trisomy eight in ES cells is a common potential problem in gene targeting and interferes with germ line transmission," Developmental Dynamics, 209(1):85-91 (1997).
Lu et al., "Long targeting arms do not increase the efficiency of homologous recombination in the B-globin locus of murine embryonic stem cells," Blood, 102(4):1531-3 (2003).
Matzuk et al., "a-Inhibin is a tumour-suppressor gene with gonadal specificity in mice," Nature, 360:313-9 (1992).
McCafferty et al., "Antibody engineering: A practical approach," Oxford University Press, New York (1996).
McMahon et al., "The Wnt-1 (int-1) proto-oncogene is required for development of a large region of the mouse brain," Cell, 62(6):1073-85 (1990).
Nagy et al., "Derivation of completely cell culture-derived mice from early-passage embryonic stem cells," PNAS, 90(18):8424-8 (1993).
Nakatani et al., "Abnormal behavior in chromosome-engineered mouse model for human 15q11-13 duplication seen in autism," Cell, 137(7):1235-46 (2009).
Nobrega et al., "Megabase deletions of gene deserts result in viable mice," Nature, 431:988-93 (2004).
Opposition Statement filed by Kymab Limited in European Patent No. EP 2,264,163.
Opposition Statement filed by Merus B.V. in European Patent No. EP 2,264,163.
Opposition Statement filed by Novo Nordisk A/S in European Patent No. EP 2,264,163.

(56) References Cited

OTHER PUBLICATIONS

Prosser et al., "A resource of vectors and ES cells for targeted deletion of microRNAs in mice," Nat Biotechnol, 29(9):840-5 (2011).
*Regeneron Pharmaceuticals, Inc.* v. *Kymab Limited*—Proceedings dated Nov. 18, 2015.
*Regeneron Pharmaceuticals, Inc.* v. *Kymab Limited*—Proceedings dated Nov. 19, 2015.
*Regeneron Pharmaceuticals, Inc.* v. *Kymab Limited*—Proceedings dated Nov. 20, 2015.
*Regeneron Pharmaceuticals, Inc.* v. *Kymab Limited*—Proceedings dated Nov. 23, 2015.
*Regeneron Pharmaceuticals, Inc.* v. *Kymab Limited*—Proceedings dated Nov. 24, 2015.
*Regeneron Pharmaceuticals, Inc.* v. *Kymab Limited*—Proceedings dated Nov. 25, 2015.
*Regeneron Pharmaceuticals, Inc.* v. *Kymab Limited*—Proceedings dated Nov. 26, 2015.
*Regeneron Pharmaceuticals, Inc.* v. *Kymab Limited*—Proceedings dated Nov. 27, 2015.
*Regeneron Pharmaceuticals, Inc.* v. *Kymab Limited*—Proceedings dated Nov. 30, 2015.
*Regeneron Pharmaceuticals, Inc.* v. *Kymab Limited*—Proceedings dated Dec. 7, 2015.
*Regeneron Pharmaceuticals, Inc.* v. *Kymab Limited*—Proceedings dated Dec. 8, 2015.
Reh WA & Vasquez KM, Encyclopedia of Life Sciences, John Wiley and sons, Ltd, 2014.
Retter et al., "Sequence and characterization of the Ig heavy chain constant and partial variable region of the mouse strain 129S1," J Immunol, 179:2419-27 (2007).
Ringrose et al., "Quantitative comparison of DNA looping in vitro and in vivo: cromatin increases effective DNA flexibility at short distances," The EMBO Journal, 18(23):6630-41 (1999).
Sharova et al., "Global gene expression profiling reveals similarities and differences among mouse pluripotent stem cells of different origins and strains," Developmental Biol, 307(2):446-59 (2007).
Shen et al., "A general method to modify BACs to generate large recombinant DNA fragments," Mol Biotechnol, 31:181-6 (2005).
Skarnes et al., "A conditional knockout resource for the genome-wide study of mouse gene function," Nature, 474:337-42 (2011).
Smith et al., "A site-directed chromosomal translocation induced in embryonic stem cells by Cre-loxP recombination," Nature Genetics, 9(4):376-85 (1995).
Stacey et al., "Use of double-replacement gene targeting to replace the murine a-lactalbumin gene with its human counterpart in embryonic stem cells and mice," Mol Cell Biol, 14(2):1009-16 (1994).
Storb et al., "Ig gene expression and regulation in Ig transgenic mice" —in Honjo et al., Immunoglobulin Genes (2nd edition), 345-63 (1995).
Takahashi et al., "Induction of pluripotent stem cells from mouse embryonic and adult fibroblast cultures by defined factors," Cell, 126(4):663-76 (2006).
Technical primer—undated.
Toyooka et al., "Identification and characterization of subpopulations in undifferentiated ES cell culture," Development, 135(5):909-18 (2008).
Valenzuela et al., Supplementary Data for "High-throughput Engineering of the Mouse Genome Couples with High-Resolution Expression Analysis," Nature Biotechnology, 21(6): 652-659 (2003).
VelocImmune history narrative—undated.
Wallace et al., "Manipulating the mouse genome to engineer precise functional syntenic replacements with human sequence," Cell, 128:197-209 (2007).
Wu et al., "A protocol for constructing gene targeting vectors: generating knockout mice for the cadherin family and beyond," Nature Protocols, 3(6):1056-76 (2008) [document D52 from T1526/11].

Yu et al., "A mouse model of Down syndrome trisomic for all human chromosome 21 syntenic regions," Human Mol Genetics, 1-12 (2010).
Zambrowicz et al., "Disruption and sequence identification of 2,000 genes in mouse embryonic stem cells," Nature, 392:608-11 (1998).
Zheng et al., "Engineering a mouse balancer chromosome," Nature Genetics, 22:375-8 (1999).
Abremski and Hoess, "Bacteriophage P1 Site-specific Recombination, Purification and Properties of the Cre Recombinase Protein," Journal of Biological Chemistry 259(3):1509-1514 (1984).
Akahori et al., "Nucleotide sequences of all the gamma gene loci of murine immunoglobulin heavy chains," Genomics Apr. 1, 1997;41(1):100-4.
Aldhous, "Transgenic mice display a class (switching) act," Science 262(5137):1212-1213 (1993).
Alt et al., "Immunoglobulin genes in transgenic mice," Trends in Genetics 1:231-236 (1985).
Alt et al., "Regulation of genome rearrangement events during lymphocyte differentiation," Immunol Rev 89:5-30 (1986).
Alt et al., "Control of recombination events during lymphocyte differentiation: heavy chain variable region gene assembly and heavy chain class switching," Ann NY Acad Sci 546:9-24 (1988).
Andrews et al., "The FLP Recombinase of the 2µ Circle DNA of Yeast: Interaction with Its Target Sequences," Cell 40:795-803 (1985).
Asakawa et al., "Human BAC library: construction and rapid screening," Gene 191(1):69-79 (1997).
Berman et al., "Content and organization of the human Ig $V_H$ locus: definition of three new $V_H$ families and linkage to the Ig $C_H$ locus," The EMBO Journal, vol. 7 No. 3 pp. 727-738 (1988).
Bethke and Sauer, "Segmental Genomic Replacement by Cre-Mediated Recombination: Genotoxic Stress Activation of the p53 Promoter in Single-Copy Transformants," Nucleic Acids Res 25(14):2828-2834 (1997).
Birshtein BK. The role of CTCF binding sites in the 3' immunoglobulin heavy chain regulatory region. Front Genet. Nov. 16, 2012;3:251.
Blackwell et al., "Recombination between immunoglobulin variable region gene segments is enhanced by transcription," Nature 324(6097):585-589 (1986).
Blair et al., The Liberation of Embryonic Stem Cells, PLoS Genetics, vol. 7 pp. 1-6 (2011).
Bono et al., "$V_H$ Gene Segments in the Mouse and Human Genome," J. Mol. Biol. 342, 131-143 (2004).
Braun, "MyoD expression marks the onset of skeletal myogenesis in Myf-5 mutant mice," Development, 120:3083-3092 (1994).
Brinster et al., "Introns increase transcriptional efficiency in transgenic mice," Proc Natl Acad Sci USA 85(3):836-840 (1988).
Brinster, R.L. et al., "Targeted correction of a major histocompatibility class II E alpha gene by DNA microinjected into mouse eggs," Proc. Natl. Acad. Sci. (U.S.A.) 86:7087-7091 (1989).
Brüggemann et al., "The Immunogenicity of Chimeric Antibodies," J Exp Med 170:2153-2157 (1989).
Bruggemann et al., "A repertoire of monoclonal antibodies with human heavy chains from transgenic mice," Proc Natl Acad Sci USA 86:6709-6713 (1989).
Bruggemann et al., "Construction, Function and Immunogenicity of Recombinant Monoclonal Antibodies," Behring Inst. Mitt. 87:21-24 (1990).
Bruggemann et al., "Human antibody production in transgenic mice: expression from 100 kb of the human IgH locus," Eur J Immunolog 21(5):1323-1326 (1991).
Bruggemann and Neuberger, "Generation of Antibody Repertoires in Transgenic Mice," Methods 2(2):159-165 (1991).
Bruhns, "Properties of mouse and human IgG receptors and their contribution to disease models," Blood 119:5640-5649 (2012).
Buttin, "Exogenous Ig Gene Rearrangement in Transgenic Mice: A New Strategy for Human Monoclonal Antibody Production?" Trends in Genetics 3(8):205-206 (1987).
Carson et al., "A linkage map of the mouse immunoglobulin lambda light chain locus," Immunogenetics 29:173-179 (1989).

(56) References Cited

OTHER PUBLICATIONS

Chang et al., "Immunologic memory to phosphocholine. IV. Hybridomas representative of Group I (T15-like) and Group II (non-T15-like) antibodies utilize distinct VH genes," J Immunol 132(3):1550-1555 (1984).
Chauveau et al., "Insertion of the IgH locus 3' regulatory palindrome in expression vectors warrants sure and efficient expression in stable B cell transfectants" Gene. Nov. 19, 1998;222(2):279-85.
Chen et al., "Immunoglobulin heavy chain gene replacement: a mechanism of receptor editing," Immunity 3(6):747-755 (1995).
Choi et al., "Transgenic mice containing a human heavy chain immunoglobulin gene fragment cloned in a yeast artificial chromosome," Nature Genetics 4(2):117-123 (1993).
Clark, et al., Genes of the RecE and RecE Pathways of Conjugational Recombination in *Escherichia coli*, National Library of Medicine, (1984), pp. 453-462.
Cox, "The FLP protein of the yeast 2-microns plasmid: expression of a eukaryotic genetic recombination system in *Escherichia coli*," Proc Natl Acad Sci USA 80(14):4223-4227 (1983).
DeChiara et al., "A Growth-Deficiency Phenotype in Heterozygous Mice Carrying an Insulin-Like Growth Factor II Gene Disrupted by Targeting," Nature 345:78-80 (1990).
Delpy et al., "B Cell Development Arrest Upon Insertion of a neo Gene Between JH and Eu: Promoter Competition Results in Transcriptional Silencing of Germline JH and Complete V(D)J Rearrangements," J Immunol 169:6875-6882 (2002).
Doetschman et al., "Targeted Correction of a Mutant HPRT Gene in Mouse Embryonic Stem Cells," Nature 330:576-578 (1987).
Eliceiri et al., "Stable integration and expression in mouse cells of yeast artificial chromosomes harboring human genes," Proc Natl Acad Sci 88:2179-2183 (1991).
Fiering et al., An "in-out" strategy using gene targeting and FLP recombinase for the functional dissection of complex DNA regulatory elements: Analysis of the ,8-globin locus control region, Proc. Natl. Acad. Sci. USA vol. 90, pp. 8469-8473, (1993).
Fujieda et al., "Multiple Types of Chimeric Germline Ig Heavy Chain Transcripts in Human B Cells," J Immunol 157(8):3450-3459 (1996).
Gallo et al., "The human immunoglobulin loci introduced into mice," Eur J Immunol 30:534-540 (2000).
Garrett et al., "Chromatin Architecture near a Potential 3' End of the Igh Locus Involves Modular Regulation of Histone Modifications during B-Cell Development and in vivo Occupancy at CTCF sites," Mol Cell Biol. 25(4): 1511-25 (2005).
Giusti et al., "Somatic recombination of heavy chain variable region transgenes with the endogenous immunoglobulin heavy chain locus in mice," Proc Natl Acad Sci USA 89:10321-10325 (1992).
Giusti and Manser, "Somatic Generation of Hybrid Antibody H Chain Genes in Transgenic Mice via Interchromosomal Gene Conversion," J Exp Med 179:235-248 (1994).
Goodhardt et al., "Rearrangement and expression of rabbit immunoglobulin K light chain genes in transgenic mice," Proc Natl Acad Sci USA 84:4229-4233 (1987).
Guo et al., "CTCF-binding elements mediate control of V(D)J recombination" Nature Sep. 2011 II ;477(7365):424-30.
Haines and Brodeur, "Accessibility Changes Across the Mouse IgH-V Locus During B Cell Development," Eur J Immunol 28:4228-4235 (1998).
Hall and Kolodner, "Homologous Pairing and Strand Exchange Promoted by the *Escherichia coli* RecT protein," Proc Natl Acad Sci USA 91:3205-3209 (1994).
Hall et al., "Identification and Characterization of the *Escherichia coli* RecT Protein, a Protein Encoded by the recE Region that Promotes Renaturation of Homologous Single-Stranded DNA," Journal of Bacteriology 175(4):277-287 (1993).
Harding and Lonberg, "Class switching in human immunoglobulin transgenic mice," Ann NY Acad Sci 764:536-546 (1995).
Hardy and Hayakawa, "B cell development pathways," Annu Rev Immunol 19:595-621 (2001).

Hasty et al., "Gene targeting, principles, and practice in mammalian cells," Chapter 1, Gene Targeting a Practical Approach, Ed. Alexandra Joyner, Oxford University Press, pp. 1-35 (2000).
Hoess et al., "The Role of the loxP Spacer Region in P1 Site-Specific Recombination," Nucleic Acids Research 14(5):2287-2300 (1986).
Hofker et al., "Complete physical map of the human immunoglobulin heavy chain constant region gene complex," Proc Natl Acad Sci USA 86(14):5567-5571 (1989).
Iglesias et al., "Early B cell development requires µ signaling," Eur J Immunol 23:2622-2630 (1993).
Ishida et al., "Production of Human Monoclonal and Polyclonal Antibodies in TransChromo Animals," Cloning Stem Cells 4:91-102 (2002).
Jakobovits, "The long-awaited magic bullets: therapeutic human monoclonal antibodies from transgenic mice," Exp. Opin. Invest. Drugs vol. 7: 607-614 (1998).
Jakobovits et al, "From XenoMouse technology to panitumumab, the first fully human antibody product from transgenic mice," Nat. Biotech. 25(10):1134-1143 (2007).
Janeway et al., "Immuno Biology, the Immune System in Health and Disease," Fourth Edition, Current Biology Publications (1999).
Johnson et al., "A method of estimating the numbers of human and mouse immunoglobulin V-genes," Genetics. Mar. 1997;145(3):777-86.
Kim et al., "The B-cell-specific transcription coactivator OCAB/OBF-1/Bob-1 is essential for normal production of immunoglobulin isotypes," Nature 383(600):542-547 (1996).
Kim, et al., Inactivation of the human β-globin gene by targeted insertion into the β-globin locus control region, Genes and Development vol. 6, pp. 928-938 (1992).
Kingzette et al., "Trans-chromosomal recombination within the Ig heavy chain switch region in B lymphocytes," 95:11840-11845 (1998).
Kirschbaum et al., The mouse immunoglobulin x locus contains about 140 variable gene segments, Eur. J. Immunol, vol. 26, pp. 1613-1620 (1996).
Kirschbaum et al., "The central part of the mouse immunoglobulin kappa locus," Eur J Immunol. Jul. 1999;29(7):2057-64.
Kirschbaum et al., "The 3' part of the immunoglobulin kappa locus of the mouse," Eur J Immunol. May 1998;28(5):1458-66.
Kitamura et al., "A B cell-deficient mouse by targeted disruption of the membrane exon of the immunoglobulin mu chain gene," Nature 350:423-426 (1991).
Kohler and Milstein, "Continuous cultures of fused cells secreting antibody of predefined specificity," Nature 256:495-497 (1975).
Koller et al., "Germ-Line Transmission of a Planned Alteration Made in a Hypoxanthine Phosphoribosyltransferase Gene by Homologous Recombination in Embryonic Stem Cells," Proc Natl Acad Sci USA 86:8927-8931 (1989).
Kolodner et al., "Homologous Pairing Proteins Encoded by the *Escherichia coli* recE and recT Genes," Molecular Microbiology 11(1):23-30 (1994).
Koop et al., "Analysis and comparison of the mouse and human immunoglobulin heavy chain JH-Cmu-Cdelta locus," Mol Phylogenet Evol 5(1):33-49 (1996).
Koval and Matthews, "Toroidal Structure of Lambda-Exonuclease," Science 277(5333):1824-1927 (1997).
Kuhn et al., "Generation and Analysis of Interleukin-4 Deficient Mice," Science 254(5032):707-710 (1991).
Kuroiwa et al., "Manipulation of human minichromosomes to carry greater than megabase-sized chromosome inserts," Nature Biotech 18:1086-1090 (2000).
Kusano et al., "Involvement of RecE Exonuclease and RecT annealing protein in DNA Double-Strand Break Repair by Homologous Recombination," Gene 138:17-25 (1994).
Lander et al., "Initial sequencing and analysis of the human genome," Nature 409:860-921 (2001).
Lieberson et al., "An enhancer at the 3' end of the mouse immunoglobulin heavy chain locus," Nucleic Acids Res. Feb. 25, 1991;19(4):933-7.
Liu et al., "Mapping of Heavy Chain Genes for Mouse Immunoglobulins M and D," Science 209:1348-1353 (1980).

(56) References Cited

OTHER PUBLICATIONS

Liu, et al., MICER Targeting Vectors for Manipulating the Mouse Genome, Methods in Molecular Biology, vol. 693 pp. 245-256 (2011).
Lonberg et al., "Antigen-specific human antibodies from mice comprising four distinct genetic modifications," Nature 368(6474):856-859 (1994).
Malureanu, Targeting Vector Construction Through Recombineering, Methods in Molecular Virology, vol. 693 pp. 181-203 (2011).
Malynn et al., "Expression of the immunoglobulin heavy-chain variable gene repertoire," Curr Top Microbiol Immunol 135:75-94 (1987).
Martensson and Ceredig, "Role of the surrogate light chain and the pre-B-cell receptor in mouse B-cell development," Immunology 101:435-441 (2000).
Martinez-Jean et al., "Nomenclature and overview of the mouse (Mus musculus and Mus sp.) immunoglobulin kappa (IGK) genes," Exp Clin Immunogenet. 2001;18(4):255-79.
Metzger et al., "Conditional site-specific recombination in mammalian cells using a ligand-dependent chimeric Cre recombinase," Proc Natl Acad Sci USA 92(15):6991-6995 (1995).
Meyer-Leon et al., "Site-specific genetic recombination promoted by the FLP protein of the yeast 2-micron plasmid in vitro," Cold Spring Harb Symp Quant Biol 49:797-804 (1984).
Michaelson et al., "Regulation of the replication of the murine immunoglobulin heavy chain gene locus: evaluation of the role of the 3' regulatory region," Mol Cell Biol. Oct. 1997;17(10):6167-74.
Moreadith et al., "Gene targeting in embryonic stem cells: the new physiology and metabolism," J. Mol. Med. 75(3):208-216 (1997).
Morrison et al., "Chimeric human antibody molecules: mouse antigen-binding domains with human constant region domains," Proc Natl Acad Sci USA 81:6851-6855 (1984).
Mortensen et al., "Production of Homozygous Mutant ES Cells with a Single Targeting Construct," Mol Cell Biol 12(5):2391-2395 (1992).
Mullins et al., "Transgenesis in the rat and larger mammals," J. Clin. Invest. 97:1557-1560 (1996).
Murphy, "Lambda-Gam Protein Inhibits the Helicase and Chi-Stimulated Recombination Activities of Escherichia coli RecBCD Enzyme," Journal of Bacteriology 173(18):5808-5821 (1991).
Myers and Stahl, "Chi and the RecBC D Enzyme of Escherichia coli," Annu Rev Genet 28:49-70 (1994).
Nadeau et al., "Lengths of chromosomal segments conserved since divergence of man and mouse," Proc Natl Acad Sci 81:814-818 (1984).
Neuberger et al., "Diversification and Selection Mechanisms for the Production of Protein Repertoires, Lessons from the Immune System," Appl Biochem Biotechnol 83(1-3):53-60 (2000).
Nicholson et al., "Antibody Repertoires of Four- and Five-Feature Translocus Mice Carrying Human Immunoglobulin Heavy Chain and Kappa and Gamma Light Chain Yeast Artificial Chromosomes," J Immunol 163:6898-6906 (1999).
Noirot and Kolodner, "DNA Strand Invasion Promoted by Escherichia Coli RecT Protein," J Biol Chem 273(20):12274:12280 (1998).
Ober et al., "Differences in promiscuity for antibody-FcRn interactions across species: implications for therapeutic antibodies," Int. Immunol. 13:1551-1559 (2001).
Olson, et al., "Know Your Neighbors: Three Phenotypes in Null Mutants of the Myogenic bHLH Gene MRF4," Cell, 85(1):1-4, (1996).
Ong et al., "3' IgH Enhancer Elements Shift Synergistic Interactions During B Cell Development," J Immunol. 160:4896-4903 (1998).
Orkin et al., "Mutation in an intervening sequence splice junction in man," Proc Natl Acad Sci USA 78:5041-5045 (1981).
Pan et al., "Regulation of the Promoter for Human Immunoglobulin Lambda3 Germ-Line Transcription and its Interaction with the 3' Alpha Enhancer," Eur J Immunol 39:1019-1029 (2000).
Pera et al., "Human Embryonic Stem Cells," Journal of Cell Science 113:5-10 (2000).
Perlot et al., "Elucidation of IgH intronic enhancer functions via germline deletion," Proc Natl Acad Sci USA 102(40): 14362-7 (2005).
Perlot et al., "Analysis of mice lacking DNase I hypersensitive sites at the 5' End of the IgH locus," PLoS One 5(11):e13992 (2010).
Pham et al., "Long-range disruption of gene expression by a selectable marker cassette," Proc. Natl. Acad. Sci., vol. 93, pp. 13090-13095 (1996).
Pierce, Genetics: A Conceptual Approach, 4th ed. Ch. 19: Molecular Genetic Analysis and Biotechnology. pp. 513-527. W.H. Freeman and Company, New York (2012).
Popov et al., "A human immunoglobulin lambda locus is similarly well expressed in mice and humans," J. Exp. Med. 189(1):1611-1619 (1999).
Poteete et al., "Modulation of Escherichia coli RecBCD Activity by the Bacteriophage Lambda Gam and P22 Abc Functions," Journal of Bacteriology 170(5):2012-2021 (1988).
Primrose & Twyman, Principles of Genome Analysis and Genomics, 3rd ed. Ch. 3: Subdividing the genome, pp. 34-46. Blackwell, Massachusetts (2003).
Rajewsky et al., "Evolutionary and Somatic Selection of the Antibody Repertoire in the Mouse," Science 238:1088-1094 (1987).
Ramirez-Solis et al., "Chromosome Engineering in Mice," Nature 378:720-724 (1995).
Rivero-Muller, et al., Assisted large fragment insertion by Red/ET-recombination (ALFIRE)—an alternative and enhanced method for large fragment recombineering, Nucleic Acids Research vol. 35 (2007).
Roque et al., "A developmentally modulated chromatin structure at the mouse immunoglobulin kappa 3' enhancer," Mol Cell Biol. Jun. 1996;16(6):3138-55.
Röschenthaler et al., "The 5' part of the mouse immunoglobulin kappa locus," Eur J Immunol. Jul. 1999;29(7):2065-71.
Röschenthaler et al., "The 5' part of the mouse immunoglobulin kappa locus as a continuously cloned structure" Eur J Immunol. Dec. 2000;30(12):3349-54.
Schedl et al., "Transgenic Mice Generated by Pronuclear Injection of a Yeast Artificial Chromosome," Nucleic Acids Res 20:3073-3077 (1992).
Schedl et al., "A Method for the Generation of YAC Transgenic Mice by Pronuclear Microinjection," Nucleic Acids Res 21(20):4783-4787 (1993).
Schlissel and Morrow, "Ig Heavy Chain Protein Controls B Cell Development by Regulating Germ-Line Transcription and Retargeting V(D)J Recombination," J. Immunol. 153(4):1645-1657 (1994).
Schupp et al., "A yeast artificial chromosome contig spanning the mouse immunoglobulin kappa light chain locus," Immunogenetics. 1997;45(3):180-7.
Schwartzberg et al., "Germ-Line Transmission of a c-abl Mutation Produced by Targeted Gene Disruption in ES Cells," Reports 799-803 (1989).
Seidl et al., Position-dependent inhibition of class switch recombination by PGK-neo cassettes inserted into the immunoglobulin heavy chain constant region locus Proc. Natl. Acad. Sci. USA vol. 96, pp. 3000-3005, Mar. 1999.
Sekiguchi et al., Chronic Graft-Versus-Host in Ig Knocking Transgenic Mice Abrogates B Cell Tolerance in Anti-Double-Stranded DNA B Cells, J Immunol. 168:4142-4153 (2002).
Selmayr et al., "B-cell lymphoma idiotypes chimerized by gene targeting can induce tumor immunity," Cancer Gene Ther 7(3):501-506 (2000).
Shimizu et al., "Immunoglobulin Double-Isotype Expression by Trans-mRNA in a Human Immunoglobulin Transgenic Mouse," Proc Natl Acad Sci USA 86:8020-8023 (1989).
Shimizu et al., "Trans-Splicing as a Possible Molecular Mechanism for the Multiple Isotype Expression of the Immunoglobulin Gene," J. Exp. Med., 173:1385-93 (1991).
Silver, "Mouse Genetics," Oxford University Press, 1995.
Schroeder et al., "Structure and evolution of mammalian VH families," Int. Immunology 2(1):41-50.
Snustad & Simmons, Principles of Genetics, 6th ed. Ch. 14—The Techniques of Molecular Genetics, pp. 366-376. Wiley (2012).

(56) References Cited

OTHER PUBLICATIONS

Spanopoulou et al., "Functional immunoglobulin transgenes guide ordered B-cell differentiation in Rag-1-deficient mice," Genes Dev 8(9):1030-1042 (1994).
Steven, S., "Human Antibody Discovery VelocImmune—A novel platform," Pharma Focus Asia (8)72-74 (2008).
Storb et al., "Physical Linkage of Mouse Lambda Genes by Pulsed-Field Gel Electrophoresis Suggests that the Rearrangement Process Favors Proximate Target Sequences," Mol Cell Biol 9(2):711-718 (1989).
Taylor et al., "A transgenic mouse that expresses a diversity of human sequence heavy and light chain immunoglobulins," Nucleic Acids Research 20(23):6287-6295 (1992).
Thiebe et al., "The variable genes and gene families of the mouse immunoglobulin kappa locus," Eur J Immunol. Jul. 1999;29(7):2072-81.
Third Party Observation Filed During Prosecution of European Patent Application No. 02709544.7.
Thomas et al., "Targeted Disruption of the Murine int-I Proto-Oncogene Resulting in Severe Abnormalities in Midbrain and Cerebellar Development," Nature 346(6287):847-850 (1990).
Thompson et al., "Germline transmission and expression of a corrected HPRT gene produced by gene targeting in embryonic stem cells," Cell 56(2):313-321 (1989).
Thresher et al., "Electron Microscopic Visualization of RecT Protein and its Complexes with DNA," J Mol Biol 254:364-371 (1995).
Tomizuka et al., "Functional expression and germline transmission of a human chromosome fragment in chimaeric mice," Nature Genetics 16(2):133-143 (1997).
Tuaillon et al., "Human immunoglobulin heavy-chain minilocus recombination in transgenic mice: gene-segment use in mu and gamma transcripts," Proc Natl Acad Sci USA 90(8):3720-3724 (1993).
Ulrich, et al., Exponential Megapriming PCR (EMP) Cloning—Seamless DNA Insertion into any Target Plasmid without Sequence Constraints, PLOS One vol. 7, Dec. 2012.
Venter et al., "The sequence of the human genome," Science 201(5507):1304-1351 (2001).
Vollmer et al., Functional Expression and Analysis of a Human HLA-DQ Restricted, Nickel-Reactive T Cell Receptor in Mouse Hybridoma Cells, J Invest. Dermatol. 113:175-181 (1999).
Vora and Manswer, "Altering the Antibody Repertoire via Transgene Homologous Recombination: Evidence for Global and Clone-autonomous Regulation of Antigen driven B Cell Differentiation," J Exp Med 181:271-281 (1995).
Wagner et al., "The diversity of antigen-specific monoclonal antibodies from transgenic mice bearing human immunoglobulin gene miniloci," Eur J Immunol 24:2672-2681 (1994).
Waterson et al., "Initial sequencing and comparative analysis of the mouse genome," Nature 420:520-562 (2002).
Willers et al., "Apparent Trans-Chromosomal Antibody Class Switch in Mice Bearing an Igh(a) mu-Chain Transgene on an Igh(b) Genetic Background," Immunobiol 200(1):150-164 (1999).
Wu et al., "Comparative DNA Sequence Analysis of Mouse and Human Protocadherin Gene Clusters," Genome Res. 11:389-404 (2001).
Xu and Davis, "Diversity in the CDR3 Region of Vh is Sufficient for Most Antibody Specificities," Immunity 13:37-45 (2000).
Yamamura et al., "Cell-type-specific and regulated expression of a human gamma1 heavy-chain immunoglobulin gene in transgenic mice," Proc Natl Acad Sci USA 83:2152-2156 (1986).
Yancopoulos and Alt, "Regulation of the Assembly and Expression of Variable-Region Genes," Ann Rev Immunol 4:339-368 (1986).
Yancopoulos et al., "Developmentally regulated and strain-specific expression of murine VH gene families," J Exp Med 168(1):417-435 (1988).
Yancopoulos and Al, "Reconstruction of an immune system," Science 241(4873):1581-1583 (1988).
Yang et al., "Fully human anti-interleukin-8 monoclonal antibodies: potential therapeutics for the treatment of inflammatory disease states," Journal of Leukocyte Biology 66(3):401-410 (1999).
Zachau et al., "The immunoglobulin kappa gene families of human and mouse: a cottage industry approach," Biol Chem. Sep.-Oct. 2000;381(9-10):951-4.
Zhou et al., "Generation of Mutated Variants of the Human Form of the MHC Class I-related Receptor, FcRn, with Increased Affinity for Mouse Immunoglobulin G," J. Mol. Biol. 332:901-913 (2003).
Zocher et al., "Clustered and interspersed gene families in the mouse immunoglobulin kappa locus," Eur J Immunol. Dec. 1995;25(12):3326-31.
Pawlitzky, I. et al., "Identification of a Canadian Regulatory Element within the 5' Flanking Region of the Mouse *Igh* Locus Defined by Pro-B Cell-Specific Hypersensitivity Associated with Binding of PU.1, Pax5, and E2A," J Immunol, 176:6839-6851 (2006).
*Regeneron Pharmaceuticals, Inc.* v. *Ablexis, LLC*, Defendant Ablexis, LLC's Proposed Claim Construction dated Jul. 2014.
*Regeneron Pharmaceuticals, Inc.*v. *Ablexis, LLC*, Defendant Ablexis, LLC's Invalidity Contentions dated Jun. 30, 2014.
Dariavach, P. et al., "The IgH 3'-enhancer," Eur. J. Immunol., 21:1499-1504 (1991).
*Regeneron Pharmaceuticals, Inc.* v. *Merus B.V.*, Defendant Merus B.V.'s Invalidity Contentions dated Jun. 30, 2014.
Opposition to EP Patent EP-B-1360287, *Regeneron Pharmaceuticals, Inc.* v. *Kymab Limited* 's Statement of Facts and Arguments.
Third Party Observation for Application No. EP20100010741 dated Jul. 9, 2014.
*Regeneron Pharmaceuticals, Inc.* v. *Merus B.V.*, Defendant Merus B.V.'s Proposed Claim Constructions.
*Regeneron Pharmaceuticals, Inc.* v. *Merus B.V.*, Defendant Merus B.V.'s Statement of Facts and Arguments.
Opposition to EP Patent EP-B-1360287, Notice of Novo Nordisk AS Intervention dated Apr. 3, 2014.
Opposition to EP Patent EP-B-1360287, Comments by Opponent Kymab LTD., dated Feb. 10, 2014.
Opposition to EP Patent EP-B-1360287, Regeneron Pharmaceuticals, Inc. Response to Opposition dated Jan. 28, 2014.
Johnston et al., "Complete sequence assembly and characterization of the C57BL/6 mouse Ig heavy chain V region," J Immunol. 176(7):4221-34 (2006).
Celera press release, "Celera Genomics Publishes First Analysis of Human Genome," 4 pages, Feb. 12, 2001.
Chevillard et al., "A Three-Megabase Yeast Artificial Chromosome Contig Spanning the C57BL Mouse Igh Locus," J. Immunol 168:5659-5666 (2002).
European Patent Application No. 02709544.7, Statement of Andrew Murphy, dated Jan. 27, 2014.
European Patent Application No. 02709544.7, Statement of Sean Stevens, Ph.D., dated Aug. 7, 2009.
European Patent Application No. 02709544.7, Statement of Sue Klapholz, M.D., Ph.D., dated Jan. 27, 2014.
Genbank, "Mouse unique YAC end WI-I-yFCLA12-R [R450,609] Whitehead I Mouse YAC Library *Mus musculus* domesticus genomic clone WI-I-yFCLA12 Right Arm, genomic survey sequence," retrieved from http://www.ncbi.nlm.nih.gov/nucgss/B07543, on Aug. 28, 2014.
George, et al., "Yeast artificial chromosome contigs reveal that distal variable-region genes reside at least 3 megabases from the joining regions in the murine immunoglobulin kappa locus," Proc. Natl. Acad. Sci. 92:12421-12425 (1995).
Giusti and Manser, "Hypermutation is Observed Only in Antibody H Chain V Region Transgenes That Have Recombined with Endogenous Immunoglobulin of cis-acting Elements Required for Somatic Mutation," J. Exp. Med. 177(3):797-809 (1993).
Hale and Garrard, "A targeted kappa immunoglobulin gene containing a deletion of the nuclear matrix association region exhibits spontaneous hyper-recombination in pre-B cells," Mol. Immun. 35:609-620 (1998).
Herault et al., "Engineering Chromosomes in Mice Through Targeted Meiotic Recombination," Nature Genetics, 20(4):381-384 (2001).

(56) References Cited

OTHER PUBLICATIONS

Honjo and Matsuda, "Immunoglobulin heavy chain loci of mouse and human," Chapters 7, Immunoglobulin Genes, Second Edition, Eds. Honjo and Alt, 145-171 (1995).
Karu et. al., "Recombinant Antibody Technology," ILAR Journal 37(3):132-141 (1995).
Mainville, et al., "Deletional Mapping of Fifteen Mouse V, Gene Families Reveals a Common Organization for Three Igh Haplotypes," J. Immunol. 165:1038-1046 (1996).
Max, E. "Immunoglobulins, Molecular Genetics," Chapter 10, Fundamental Immunology, Ed. Paul, W., 315-370 (1993).
Opposition to European Patent EP-B-1360287, Defendant Merus B.V.'s Statement of Facts and Arguments, dated 2014.
Opposition to European Patent EP-B-1360287, Second Statement of Craig H. Bassing Ph.D., dated Sep. 2, 2014.
Opposition to European Patent EP-B-1360287, Statement of Victor L. J. Tybulewicz, dated Jul. 15, 2014.
Opposition to European Patent EP-B-1360287, Statement of Craig H. Bassing, Ph.D., dated Jul. 16, 2014.
Opposition to European Patent EP-B-1360287, Statement of Prof. Anthony Defranco, dated Sep. 2, 2014.
Opposition to European Patent EP-B-1360287, Statement of Prof. Hendriks, dated Jul. 16, 2014.
*Regeneron Pharmaceuticals, Inc. v. Ablexis, LLC*, Plaintiff Regeneron Pharmaceuticals, Inc.'s Initial Disclosures Pursuant to Federal Rule of Civil Procedure 26(a)(1), dated May 9, 2014.
*Regeneron Pharmaceuticals, Inc. v. Merus B.V.*, Defendant Merus B.V.'s Propose Claim Construction Chart, dated Jun. 30, 2014.
*Regeneron Pharmaceuticals, Inc. v. Merus B.V.*, Defendant Merus's Answer and Counterclaim, dated Jul. 3, 2014.
*Regeneron Pharmaceuticals, Inc. v. Merus B.V.*, Opinion and Order by Hon. Katherine B. Forrest, dated Jun. 18, 2014.
*Regeneron Pharmaceuticals, Inc. v. Merus B.V.*, Plaintiff Regeneron Pharmaceuticals, Inc.'s Disclosure of Asserted Claims and Infringement Contentions, dated May 19, 2014.
*Regeneron Pharmaceuticals, Inc. v. Merus B.V.*, Plaintiff Regeneron Pharmaceuticals, Inc.'s Initial Disclosures Pursuant to Federal Rule of Civil Procedure 26(a)(1), dated May 9, 2014.
*Regeneron Pharmaceuticals, Inc. v. Merus B.V.*, Plaintiff Regeneron Pharmaceuticals, Inc.'s Responses to Defendant Merus B.V.'s First Set of Interrogatories (Nos. 1-3), dated Jun. 5, 2014.
*Regeneron Pharmaceuticals, Inc. v. Merus B.V.*, Regeneron Pharmaceuticals, Inc.'s Answer to Merus B.V.'s Counterclaims, dated Jul. 24, 2014.
*Regeneron Pharmaceuticals, Inc. v. Merus B.V.*, Regeneron Pharmaceuticals, Inc.'s Second Supplemental Responses and Objections to Merus B.V.'s First Set of Request for Production of Documents to Plaintiff Regeneron Pharmaceuticals Inc. (Nos. 55, 56, 154), dated Aug. 26, 2014.
*Regeneron Pharmaceuticals Inc. v. Merus B.V. et al.*, Defendants' Responsive Claim Construction Brief, dated Aug. 21, 2014.
*Regeneron Pharmaceuticals Inc., v. Merus B.V. et al.* Joint Claim Construction and Prehearing Statement, dated Jul. 28, 2014.
*Regeneron Pharmaceuticals Inc., v. Merus B.V. et al.* Regeneron's Reply Claim Construction Brief Aug. 28, 2014.
*Regeneron Pharmaceuticals, Inc. v. Ablexis B.V.*, Letter to Judge Forrest responding to court Request, dated Jul. 23, 2014.
*Regeneron Pharmaceuticals, Inc. v. Ablexis B.V.*, Plaintiff Regeneron Pharmaceuticals, Inc.'s Responses to Defendant Ablexis LLC's First Set of Interrogatories (Nos. 1-4), dated May 14, 2014.
*Regeneron Pharmaceuticals, Inc. v. Ablexis B.V.*, Regeneron Pharmaceuticals, Inc.'s Answers to Ablexis LLC's Counterclaims, dated May 27, 2014.
*Regeneron Pharmaceuticals, Inc. v. Ablexis, LLC* Plaintiff Regeneron Pharmaceuticals, Inc.'s Disclosure of Asserted Claims and Infringement Contentions, dated May 19, 2014.
*Regeneron Pharmaceuticals, Inc. v. Ablexis, LLC*, Defendant Ablexis Proposed Claim Construction Chart, dated Jul. 2014.
*Regeneron Pharmaceuticals, Inc. v. Ablexis, LLC*, Defendant Ablexis, LLC's Answer, Affirmative Defenses, and Counterclaims to Regeneron Pharmaceuticals, Inc.'s Complaint, dated May 5, 2014.
*Regeneron Pharmaceuticals, Inc. v. Ablexis, LLC*, Expert Declaration of William T. Garrard, dated Aug. 21, 2014.
*Regeneron Pharmaceuticals, Inc. v. Merus B.V.*, Plaintiff Regeneron Pharmaceuticals, Inc.'s First Supplemental Responses to Court Interrogatory Nos. 1-2, dated Sep. 5, 2014.
*Regeneron Pharmaceuticals, Inc. v. Merus B.V.*, Plaintiff Regeneron Pharmaceuticals, Inc.'s Responses to Court Interrogatory Nos. 1-2, dated Sep. 5, 2014.
*Regeneron Pharmaceuticals, Inc. v. Merus, B.V.et al.*, Errata to Expert Declaration of Jeffrey V. Ravetch, M.D., Ph.D., dated Sep. 8, 2014.
*Regeneron Pharmaceuticals, Inc. v. Merus, B.V.et al.*, Expert Declaration of Jeffrey V. Ravetch, Ph.D., public version, dated Aug. 28, 2014.
*Regeneron Pharmaceuticals, Inc., v. Merus B.V.* Regeneron's Opening Claim Construction Brief, dated Aug. 8, 2014.
*Regeneron Pharmaceuticals, Inc., v. Merus, B.V.* Defendants' Sur-Reply Claim Construction Brief, Sep. 9, 2014.
Selsing and Daitch "Immunoglobulin lambda genes," Chapter 9, Immunoglobulin Genes, Second Edition, Eds. Honjo and Alt, 193-203 (1995).
Third Party Observation Filed During Prosecution of European Patent Application No. 02709544.7, faxed Apr. 2, 2012.
Zachua, "The human immunoglobulin kappa gene," Chapters 8, Immunoglobulin Genes, Second Edition, Eds. Honjo and Alt, 173-191 (1995).
*Regeneron Pharmaceuticals, Inc. v. Merus B.V.*, Sur-Reply Declaration of Dr. Raphael Clynes, dated Sep. 4, 2014.
*Regeneron Pharmaceuticals, Inc. v. Merus B.V.*, Reply Expert Declaration of William T. Garrard, Ph.D., dated Sep. 4, 2014.
*Regeneron Pharmaceuticals, Inc. v. Merus B.V.*, Claim Construction Opinion & Order dated Nov. 21, 2014.
*Regeneron Pharmaceuticals, Inc. v. Merus B.V.*, Defendant Merus's Answer and Second Amended Counterclaim dated Oct. 27, 2014.
Clark, M.R. et al., "IgG Effector Mechanisms," Chem. Immunol., Basel, Karger, 65:88-110 (1997).
*Regeneron Pharmaceuticals Inc.v. Kymab Limited Witness*, Statement of Nicola Helen Dagg dated Jan. 31, 2014.
Opposition to European Patent EP 1360287 Declaration of Daniel J. Capon, Ph.D. dated Jul. 7, 2014.
European Extended Search Report for EP 14163642.3 dated Jul. 18, 2014.
European Extended Search Report for EP 14172437.7 dated Jan. 30, 2015.
European Extended Search Report for EP 14172420.3 dated Sep. 8, 2014.
Gavilondo, J.V. et al., "Antibody Engineering at the Millennium," BioTechniques, 29:128-145 (2000).
Hurle, M.R. et al., "Protein Engineering Techniques for Antibody Humanization," Biotechnology, 5:428-433 (1994).
Joyner, A.L., Gene Targeting a Practical Approach (2005).
*Regeneron Pharmaceuticals, Inc. v. Merus B.V.*, Defendant Merus's Answer and Third Amended Counterclaims dated Dec. 8, 2014.
*Regeneron Pharmaceuticals, Inc. v. Merus B.V.*, Merus's Response to Regeneron's Motion to Dismiss Third Counterclaim dated Sep. 29, 2014.
Opposition Decision for EP 02709544.7 dated Nov. 28, 2014.
Partial European Search Report for EP 14172437.7 dated Sep. 8, 2014.
Statement of Dr. Michael L. Gallo dated Sep. 11, 2014.
Third Party Observation for EP 20100010741 dated Feb. 10, 2014.
Opposition to Australian Patent Application 2009263082, Declaration of Robert Brink, Jun. 2, 2015.
Selten et al., "The Primary Structure of the Putative Oncogene pim-1 Shows Extensive Homology with Protein Kinases," Cell, 46: 603-611 (1986).
Doetschman et al., "Targeted correction of a mutant HPRT gene in mouse embryonic stem cells," Nature, 330(10): 576-578 (Dec. 10, 1987).

(56) References Cited

OTHER PUBLICATIONS te Riele et al., "Consecutive inactivation of both alleles of the pim-1 proto-oncogene by homologous recombination in embryonic stem cells," Nature, 348: 649-651 (1990).
van Deursen et al., "Modulation of gene activity by consecutive gene targeting of one creatine kinase M allele in mouse embryonic stem cells," Nucleic Acids Research, 19(10): 2637-2643 (1991).
Bruggeman, "The Preparation of Human Antibodies from Mice Harbouring Human Immunoglobulin Loci," Transgenic Animals, (1997).
Condamine et al., "Pattern of transcription of the homeo gene in the mouse embryo," Genes and Development, 2: 125-135 (1988).
Le Mouellig et al., "Targeted replacement of the homeobox gene Hox-3.1 by the *Escherichia coli* lacZ in mouse chimeric embryos," Proc. Natl. Acad. Sci. USA, 87: 4712-4716 (1990).
Clark, "IgG Effector Mechanisms," Chem Immunol., 65: 88-110(1997).
Opposition to European Patent EP-B-1360287, Statement of Daniel J. Capon, Ph.D., dated Jul. 7, 2014.
Dougier, "Interallelic class switch recombination can reverse allelic exclusion and allow trans-complementation of an IgH locus switching defect," Eur. J. Immunol., 36: 2181-2191 (2006).
Extended European Search Report for EP 2786657, dated Jan. 30, 2015.
Opposition to European Patent EP-B-1360287, Response to Application to amend the specification of a patent under Section 75 of the Patents Act 1977, dated Jun. 23, 2015.
Opposition to European Patent EP-B-1360287, Kymab Appeal Response, dated Jul. 2, 2015.
Opposition to European Patent EP-B-1360287, Merus Appeal Response, dated Jul. 2, 2015.
Opposition to European Patent EP-B-1360287, Novo Appeal Response, dated Jul. 15, 2015.
Opposition to European Patent EP-B-1360287, Patentee Grounds of Appeal, dated Feb. 15, 2015.
Opposition to European Patent EP-B-1360287, Summons to Oral Proceedings, dated Aug. 14, 2015.
European Patent Application 01992495, EPO Communication, dated Jan. 1, 2005.
European Patent Application 02709544, Regeneron Amendments to Claims, dated Dec. 22, 2008.
European Patent Application 10010741, EPO Communication, dated Jun. 2, 2015.
European Patent Application 10010741, Regeneron Request, dated Apr. 2, 2015.
European Patent Application 10010741, Regeneron Response to Third Party Observations, Jul. 1, 2014.
European Patent Application 14172437, Partial European Search Report, dated Sep. 8, 2014.
European Patent Application 14154967, Regeneron's Response to EPO Communication, dated Mar. 23, 2015.
European Patent Application 14163642, Extended European Search Report, dated Jul. 18, 2014.
European Patent Application 14163642, EPO Communication, dated Jul. 18, 2014.
European Patent Application 14172420, EPO Communication, dated Sep. 8, 2014.
European Patent Application 14172420, Extended European Search Report, dated Sep. 8, 2014.
Opposition to European Patent EP 1360287, Merus Response to Appeal, dated Jul. 2, 2015.
European Patent Application 2786657, Extended European Search Report, dated Jan. 30, 2015.
Gavilondo et al., "Antibody Engineering at the Millennium," Biotechniques, 29: 128-145 (2000).
Herring et al., "Vector-Hexamer PCR Isolation of all Insert Ends from a YAC Contig of the Mouse Igh Locus," Genome Res., 9: 673-681 (1998).
Hurle et al., "Protein engineering techniques for antibody humanization," Curr Opin Biotechnol., 5:428-433 (1994).

Joyner, "Gene Targeting: A Practical Approach," (2005).
O'Connor et al., "Construction of Large DNA Segments in *Escherichia coli*," Science., 244: 1307-1312 (1989).
Opposition to European Patent 02709544, German Document, dated Nov. 28, 2014.
*Regeneron Pharmaceuticals, Inc.* v. *Kymab Limited*, Amended Claim Form, dated Sep. 25, 2013.
*Regeneron Pharmaceuticals, Inc.* v. *Kymab Limited*, Amended Consolidated Particulars of Infringement, dated May 21, 2014.
*Regeneron Pharmaceuticals, Inc.* v. *Kymab Limited*, Amended Consolidated Particulars of Claim, dated Apr. 29, 2015.
Richards-Smith et al., "Deletion mapping of the mouse ornithine decarboxylase-related locus Odc-rs8 within Igh-V," Mammalian Genome, 3: 568-574 (1992).
Opposition to European Patent 1360287, Statement of Michael L. Gallo, dated Sep. 11, 2014.
European Patent Application 20100010741, Third Party Observation, dated Oct. 2, 2014.
*Regeneron Pharmaceuticals, Inc.* v. *Kymba Limited*, Witness Statement of Nicola Helen Dagg, dated Jan. 31, 2014.
*Regeneron Pharmaceuticals, Inc.* v. *Merus B.V.*, Complaint for Patent Infringement, dated Mar. 5, 2014.
*Regeneron Pharmaceuticals, Inc.* v. *Merus B.V.*, Regeneron Corporate Disclosure Statement, dated Mar. 19, 2014.
*Regeneron Pharmaceuticals, Inc.* v. *Merus B.V.*, Merus B.V. Corporate Disclosure Statement, dated Apr. 29, 2014.
*Regeneron Pharmaceuticals, Inc.* v. *Merus B.V.*, Merus B.V. Corporate Disclosure Statement, dated May 1, 2014.
*Regeneron Pharmaceuticals, Inc.* v. *Merus B.V.*, Merus B.V.'s Notice of Motion to Dismiss, dated May 5, 2014.
*Regeneron Pharmaceuticals, Inc.* v. *Merus B.V.*, Declaration of Patricia Carson in Support of Defendant Merus B.V.'s Motion to Dismiss, dated May 5, 2014.
*Regeneron Pharmaceuticals, Inc.* v. *Merus B.V.*, Memo in Support of Defendant Merus B.V.'s Motion to Dismiss, dated May 5, 2014.
*Regeneron Pharmaceuticals, Inc.* v. *Merus B.V.*, Stipulation Regarding Form of Document Production, dated May 19, 2014.
*Regeneron Pharmaceuticals, Inc.* v. *Merus B.V.*, Plaintiff Regeneron Pharmaceuticals, Inc.'s Opposition to Defendant Merus B.V.'s Motion to Dismiss, dated May 19, 2014.
*Regeneron Pharmaceuticals, Inc.* v. *Merus B.V.*, Regeneron's and Merus's Joint Protective Order, dated May 19, 2014.
*Regeneron Pharmaceuticals, Inc.* v. *Merus B.V.*, Order Ruling on Motion for Local Rule, dated May 20, 2014.
*Regeneron Pharmaceuticals, Inc.* v. *Merus B.V.*, Memorandum Decision and Order, dated May 28, 2014.
*Regeneron Pharmaceuticals, Inc.* v. *Merus B.V.*, Merus's Reply Memorandum of Law in Support of Merus B.V.'s Motion to Dismiss, dated May 30, 2014.
*Regeneron Pharmaceuticals, Inc.* v. *Merus B.V.*, Declaration of James McConnell in Support of Defendant Merus's Reply Memo in Support of Merus B.V.'s Motion to Dismiss, dated May 30, 2014.
*Regeneron Pharmaceuticals, Inc.* v. *Merus B.V.*, Regeneron's Opposition to Merus's Emergency Motion to Strike Portions of Dr. Smeland's Testimony, dated Jun. 5, 2015.
*Regeneron Pharmaceuticals, Inc.* v. *Merus B.V.*, Opinion and Order of Judge Katherine B. Forrest, dated Jun. 18, 2014.
*Regeneron Pharmaceuticals, Inc.* v. *Merus B.V.*, Defendant Merus's Answer and Counterclaims, dated Jul. 3, 2014.
*Regeneron Pharmaceuticals, Inc.* v. *Merus B.V.*, Defendant Merus Moves to Compel Regeneron Pharmaceuticals to answer Merus's Interrogatory No. 3, dated Jul. 17, 2014.
*Regeneron Pharmaceuticals, Inc.* v. *Merus B.V.*, Merus Moves to Compel Regeneron to comply with three Court ordered rules, dated Jul. 17, 2014.
*Regeneron Pharmaceuticals, Inc.* v. *Merus B.V.*, Regeneron Opposition to Merus Move to Compel Regeneron to answer Merus's Interrogatory No. 3, dated Jul. 21, 2014.
*Regeneron Pharmaceuticals, Inc.* v. *Merus B.V.*, Regeneron Opposition to Merus Move to Compel Regeneron to comply with three Court ordered rules, dated Jul. 21, 2014.
*Regeneron Pharmaceuticals, Inc.* v. *Merus B.V.*, Discovery Order #5, dated Jul. 22, 2014.

(56) References Cited

OTHER PUBLICATIONS

*Regeneron Pharmaceuticals, Inc.* v. *Merus B.V.*, Discovery Order #6, dated Jul. 22, 2014.
*Regeneron Pharmaceuticals, Inc.* v. *Merus B.V.*, Discovery Order #7, dated Jul. 22, 2014.
*Regeneron Pharmaceuticals, Inc.* v. *Merus B.V.*, Regeneron Pharmaceutical's Answer to Merus B.V.'s Counterclaims, dated Jul. 24, 2014.
*Regeneron Pharmaceuticals, Inc.* v. *Merus B.V.*, Order re Markman Hearing, dated Jul. 24, 2014.
*Regeneron Pharmaceuticals, Inc.* v. *Merus B.V.*, Joint Claim Construction and Prehearing Statement, dated Jul. 28, 2014.
*Regeneron Pharmaceuticals, Inc.* v. *Merus B.V.*, Regeneron's Opening Claim Construction Brief, dated Aug. 11, 2014.
*Regeneron Pharmaceuticals, Inc.* v. *Merus B.V.*, Declaration of Richard W. Krebs in Support of Plaintiff Regeneron Pharmaceuticals, Inc.'s Opening Claim Construction Brief, dated Aug. 11, 2014.
*Regeneron Pharmaceuticals, Inc.* v. *Merus B.V.*, Expert Declaration of Jeffrey V. Ravetch, dated Aug. 11, 2014.
*Regeneron Pharmaceuticals, Inc.* v. *Merus B.V.*, Merus B.V.'s Memo in Support of Motion in limine No. One and Two, dated May 8, 2015.
*Regeneron Pharmaceuticals, Inc.* v. *Merus B.V.*, Defendant Merus's Answer and First Amended Counterclaims, dated Aug. 18, 2014.
*Regeneron Pharmaceuticals, Inc.* v. *Merus B.V.*, Defendants' Responsive Claim Construction Brief, dated Aug. 21, 2014.
*Regeneron Pharmaceuticals, Inc.* v. *Merus B.V.*, Expert Declaration of William T. Garrard, dated Aug. 21, 2014.
*Regeneron Pharmaceuticals, Inc.* v. *Merus B.V.*, Declaration of Dr. Raphael Clynes, dated Aug. 21, 2014.
*Regeneron Pharmaceuticals, Inc.* v. *Merus B.V.*, Declaration of Yite John Lu in Support of Plaintiff Regeneron Pharmaceuticals Reply Claim Construction Brief, dated Aug. 28, 2014.
*Regeneron Pharmaceuticals, Inc.* v. *Merus B.V.*, Corrected Declaration of Yite John Lu in Support of Plaintiff Regeneron Pharmaceuticals, Inc.'s Reply Claim Construction Brief, dated Sep. 4, 2014.
*Regeneron Pharmaceuticals, Inc.* v. *Merus B.V.*, Defendants' Sur-Reply Claim Construction Brief, dated Sep. 4, 2014.
*Regeneron Pharmaceuticals, Inc.* v. *Merus B.V.*, Reply Expert Declaration of William T. Garrard, dated Sep. 4, 2014.
*Regeneron Pharmaceuticals, Inc.* v. *Merus B.V.*, Errata to Expert Declarations of Jeffrey V. Ravetch, dated Sep. 8, 2014.
*Regeneron Pharmaceuticals, Inc.* v. *Merus B.V.*, Regeneron Pharmaceuticals, Inc.'s Notice of Motion and Motion to Dismiss Merus B.V.'s Third Counterclaim for Declaration of Unenforceability of the '018 Patent and Strike Portions of Merus's Third Defense of Invalidity, dated Sep. 12, 2014.
*Regeneron Pharmaceuticals, Inc.* v. *Merus B.V.*, Memo of Law in Support of Plaintiff Regeneron Pharmaceuticals Inc.'s Motion to Dismiss Merus B.V.'s Third Counterclaim for Declaration of Unenforceability of the '018 Patent and Strike Portions of Merus's Third Defense of Invalidity, dated Sep. 12, 2014.
*Regeneron Pharmaceuticals, Inc.* v. *Merus B.V.*, Letter to Court from Regeneron regarding Amending its Infringement Contentions and Exhibits, dated Sep. 15, 2015.
*Regeneron Pharmaceuticals, Inc.* v. *Merus B.V.*, Letter to Judge regarding Regeneron Claim Construction Hearing Slides, dated Sep. 16, 2014.
*Regeneron Pharmaceuticals, Inc.* v. *Merus B.V.*, Merus Letter to Judge regarding Evidence from Markman Hearing and Exhibits, dated Sep. 16, 2014.
*Regeneron Pharmaceuticals, Inc.* v. *Merus B.V.*, Regeneron Letter to Judge, dated Sep. 17, 2014.
*Regeneron Pharmaceuticals, Inc.* v. *Merus B.V.*, Merus Letter to Court regarding AstraZeneca Subpoena and Exhibits, dated Sep. 18, 2014.
*Regeneron Pharmaceuticals, Inc.* v. *Merus B.V.*, Regeneron Letter to Judge regarding Docket No. 131 and Exhibits, dated Sep. 19, 2014.
*Regeneron Pharmaceuticals, Inc.* v. *Merus B.V.*, Merus Reply Letter to Regeneron Docket No. 138 and Exhibits, dated Sep. 22, 2014.
*Regeneron Pharmaceuticals, Inc.* v. *Merus B.V.*, Declaration of Margarita Wallach in Support of Non-Party AstraZeneca Pharmaceuticals LP's Opposition to Merus' Motion to Compel Response to Subpoena, dated Sep. 22, 2014.
*Regeneron Pharmaceuticals, Inc.* v. *Merus B.V.*, Declaration of Richard W. Krebs in Support of Plaintiff Regeneron Pharmaceuticals, Inc.'s Motion for Leave to Amend its Infringement Contentions, dated Sep. 22, 2014.
*Regeneron Pharmaceuticals, Inc.* v. *Merus B.V.*, Plaintiff Regeneron Pharmaceuticals, Inc.'s Memo in Support of Motion for Leave to Amend its Infringement Contentions, dated Sep. 22, 2014.
*Regeneron Pharmaceuticals, Inc.* v. *Merus B.V.*, Order—No further letters related to Markman issues, dated Sep. 22, 2014.
*Regeneron Pharmaceuticals, Inc.* v. *Merus B.V.*, Order regarding Motion to Compel Compliance with Subpoena, dated Sep. 22, 2014.
*Regeneron Pharmaceuticals, Inc.* v. *Merus B.V.*, Merus's Response to Regeneron Pharmaceuticals, Inc.'s Motion to Dismiss Merus B.V.'s Third Counterclaim for Declaration of Unenforceability of the '018 Patent and Strike Portions of Merus's Third Defense of Invalidity, dated Sep. 29, 2014.
*Regeneron Pharmaceuticals, Inc.* v. *Merus B.V.*, Declaration of Aaron D. Resetarits in Support of Defendant Merus's Response to Regeneron Pharmaceuticals, Inc.'s Motion to Dismiss Merus B.V.'s Third Counterclaim for Declaration of Unenforceability of the '018 Patent and Strike Portions of Merus's Third Defense of Invalidity, dated Sep. 29, 2014.
*Regeneron Pharmaceuticals, Inc.* v. *Merus B.V.*, Defendant Merus B.V.'s Memo in Opposition to Plaintiff Regeneron Pharmaceuticals, Inc.'s Motion for Leave to Amend Infringement Contentions, dated Sep. 29, 2014.
*Regeneron Pharmaceuticals, Inc.* v. *Merus B.V.*, Regeneron Motion for Leave to file a Combined Reply Memo, dated Sep. 30, 2014.
*Regeneron Pharmaceuticals, Inc.* v. *Merus B.V.*, Merus Letter Opposing Regeneron's Request for Reply, dated Oct. 1, 2014.
*Regeneron Pharmaceuticals, Inc.* v. *Merus B.V.*, Johnson and Johnson Letter in Opposition to Regeneron's Motion to Compel Compliance, dated Oct. 6, 2014.
*Regeneron Pharmaceuticals, Inc.* v. *Merus B.V.*, Declaration of Richard W. Krebs in Support of Plaintiff Regeneron Pharmaceuticals, Inc.'s Reply Memo in Support of Motion for Leave to Amend its Infringement Contentions, dated Oct. 6, 2014.
*Regeneron Pharmaceuticals, Inc.* v. *Merus B.V.*, Plaintiff Regeneron Pharmaceuticals, Inc.'s Reply Memo in Support of Motion for Leave to Amend its Infringement Contentions, dated Oct. 6, 2014.
*Regeneron Pharmaceuticals, Inc.* v. *Merus B.V.*, Johnson and Johnson Letter in Opposition to Plaintiff Regeneron Pharmaceuticals, Inc.'s Motion to Compel Compliance, dated Oct. 6, 2014.
*Regeneron Pharmaceuticals, Inc.* v. *Merus B.V.*, Order regarding Court's Resolution of Regeneron's Motion to Amend its Infringement Contentions, dated Oct. 7, 2014.
*Regeneron Pharmaceuticals, Inc.* v. *Merus B.V.*, Merus Letter to Court in Response Pursuant to Court Order D.I., dated Oct. 9, 2014.
*Regeneron Pharmaceuticals, Inc.* v. *Merus B.V.*, Regeneron Letter to Court in Response Pursuant to Court Order D.I., dated Oct. 9, 2014.
*Regeneron Pharmaceuticals, Inc.* v. *Merus B.V.*, Plaintiff Regeneron Pharmaceuticals, Inc.'s Reply in Support of Motion to Dismiss Merus B.V.'s Third Counterclaim for Declaration of Unenforceability of the '018 Patent and Strike Portions of Merus's Third Defense of Invalidity, dated Oct. 9, 2014.
*Regeneron Pharmaceuticals, Inc.* v. *Merus B.V.*, Order Regarding Motion to Dismiss, dated Oct. 10, 2014.
*Regeneron Pharmaceuticals, Inc.* v. *Merus B.V.*, Johnson and Johnson's Letter Brief in Opposition to Regeneron's Motion to Compel, dated Oct. 17, 2014.
*Regeneron Pharmaceuticals, Inc.* v. *Merus B.V.*, Discovery Order #8, dated Oct. 17, 2014.
*Regeneron Pharmaceuticals, Inc.* v. *Merus B.V.*, Memorandum Decision and Order, dated Oct. 17, 2014.

(56) References Cited

OTHER PUBLICATIONS

*Regeneron Pharmaceuticals, Inc.* v. *Merus B.V.*, Ablexis Letter Requesting an Extension to the Current Schedule, dated Oct. 20, 2014.
*Regeneron Pharmaceuticals, Inc.* v. *Merus B.V.*, Order regarding Johnson and Johnson's Motion Requesting a Protective Order, dated Oct. 24, 2014.
*Regeneron Pharmaceuticals, Inc.* v. *Merus B.V.*, Regeneron's Opposition to JJDC's Motion for a Protective Order, dated Oct. 24, 2014.
*Regeneron Pharmaceuticals, Inc.* v. *Merus B.V.*, Order JJDC's Motion for a Protective Order, dated Oct. 24, 2014.
*Regeneron Pharmaceuticals, Inc.* v. *Merus B.V.*, Defendant Merus's Answer and Second Amended Counterclaims, dated Oct. 27, 2014.
*Regeneron Pharmaceuticals, Inc.* v. *Merus B.V.*, Joint Stipulation of Dismissal, dated Oct. 31, 2014.
*Regeneron Pharmaceuticals, Inc.* v. *Merus B.V.*, Regeneron Letter Motion for Extension of Time to File, Nov. 6, 2014.
*Regeneron Pharmaceuticals, Inc.* v. *Merus B.V.*, Merus Letter to Move to Compel Regeneron, dated Nov. 11, 2014.
*Regeneron Pharmaceuticals, Inc.* v. *Merus B.V.*, Joint Motion to Compel, dated Nov. 14, 2014.
*Regeneron Pharmaceuticals, Inc.* v. *Merus B.V.*, Memo Endorsing Joint Motion to Compel, dated Nov. 14, 2014.
*Regeneron Pharmaceuticals, Inc.* v. *Merus B.V.*, Merus Move to Compel Regeneron and Foley Hoag, dated Nov. 17, 2014.
*Regeneron Pharmaceuticals, Inc.* v. *Merus B.V.*, Joint Request that the Court Strike Nov. 19, Dec. 3, and Dec. 10 deadlines, dated Nov. 18, 2014.
*Regeneron Pharmaceuticals, Inc.* v. *Merus B.V.*, Opinion and Order for Claim Construction, dated Nov. 21, 2014.
*Regeneron Pharmaceuticals, Inc.* v. *Merus B.V.*, Declaration of Brendan T. Jones, dated Nov. 21, 2014.
*Regeneron Pharmaceuticals, Inc.* v. *Merus B.V.*, Foley Hoag Letter Responding to Merus Move to Compel, dated Nov. 21, 2014.
*Regeneron Pharmaceuticals, Inc.* v. *Merus B.V.*, Regeneron Letter in Opposition to Merus' Move to Compel, dated Nov. 21, 2014.
*Regeneron Pharmaceuticals, Inc.* v. *Merus B.V.*, Court Order regarding Merus Move to Compel, dated Nov. 24, 2014.
*Regeneron Pharmaceuticals, Inc.* v. *Merus B.V.*, Regeneron Letter to Court regarding clarification of Court Order, dated Nov. 24, 2014.
*Regeneron Pharmaceuticals, Inc.* v. *Merus B.V.*, Regeneron Letter to Court, dated Nov. 25, 2014.
*Regeneron Pharmaceuticals, Inc.* v. *Merus B.V.*, Order—Will Issue an Unredacted Order on Merus's Letter—Motion to Compel Discovery Tomorrow at Noon, dated Dec. 4, 2014.
*Regeneron Pharmaceuticals, Inc.* v. *Merus B.V.*, Discovery Order #10, dated Dec. 5, 2014.
*Regeneron Pharmaceuticals, Inc.* v. *Merus B.V.*, Regeneron Letter—Motion Pursuant to Resolving a Discovery Dispute, dated Dec. 5, 2014.
*Regeneron Pharmaceuticals, Inc.* v. *Merus B.V.*, Defendant Merus's Answer and Third Amended Counterclaims, dated Dec. 8, 2014.
*Regeneron Pharmaceuticals, Inc.* v. *Merus B.V.*, Order regarding Status Conference, dated Dec. 11, 2014.
*Regeneron Pharmaceuticals, Inc.* v. *Merus B.V.*, Plaintiffs Notice of Motion and Motion for Dismissal of Merus's Unenforceability Claim and Entry of Final Judgment, dated Dec. 19, 2014.
*Regeneron Pharmaceuticals, Inc.* v. *Merus B.V.*, Memo in Support of Plaintiffs Motion for Dismissal of Merus's Unenforceability Claim and Entry of Final Judgment, dated Dec. 19, 2014.
*Regeneron Pharmaceuticals, Inc.* v. *Merus B.V.*, Declaration of Christopher P. Borello in Support of Plaintiffs Motion for Dismissal of Merus's Unenforceability Claim and Entry of Final Judgment, dated Dec. 19, 2014.
*Regeneron Pharmaceuticals, Inc.* v. *Merus B.V.*, Regeneron Pharmaceuticals, Inc.'s Answer to Merus B.V.'s Third Amended Counterclaims, dated Dec. 22, 2014.
*Regeneron Pharmaceuticals, Inc.* v. *Merus B.V.*, Order—Clarification of Dec. 11, 2014 Order, dated Dec. 31, 2014.
*Regeneron Pharmaceuticals, Inc.* v. *Merus B.V.*, Letter to Court withdrawing Docket 224, dated Jan. 6, 2015.
*Regeneron Pharmaceuticals, Inc.* v. *Merus B.V.*, Defendant Merus B.V.'s Memo in Opposition to Plaintiff Regeneron Pharmaceuticals, Inc.'s Motion for how this Case Should Proceed, dated Jan. 6, 2015.
*Regeneron Pharmaceuticals, Inc.* v. *Merus B.V.*, Merus Letter to Court Pursuant to Court's Order, Jan. 6, 2015.
*Regeneron Pharmaceuticals, Inc.* v. *Merus B.V.*, Reply Memo in Support of Regeneron's Motion for Dismissal of Merus's Unenforceability Claim and Entry of Final Judgment, dated Jan. 23, 2015.
*Regeneron Pharmaceuticals, Inc.* v. *Merus B.V.*, Declaration of Christopher P. Borello in Support of Regeneron's Reply Memo in Support of Regeneron's Motion for Dismissal of Merus's Unenforceability Claim and Entry of Final Judgment, dated Jan. 13, 2015.
*Regeneron Pharmaceuticals, Inc.* v. *Merus B.V.*, Order regarding Plaintiffs Motion to Dismiss, dated Jan. 15, 2015.
*Regeneron Pharmaceuticals, Inc.* v. *Merus B.V.*, Order regarding Trial for Jun. 8, 2015, dated Jan. 16, 2015.
*Regeneron Pharmaceuticals, Inc.* v. *Merus B.V.*, Merus B.V.'s Notice of Motion for Sanctions Pursuant to Fed R. Civ. p. 37 and/or to Compel Regeneron Pharmaceuticals, Inc. to Comply with the Court's Waiver Order, dated Feb. 10, 2015.
*Regeneron Pharmaceuticals, Inc.* v. *Merus B.V.*, Merus B.V.'s Memo in Support of its Motion for Sanctions Pursuant to Fed. R. Civ. p. 37 and/or to Compel Regeneron Pharmaceuticals, Inc. To Comply with the Court's Waiver Order, dated Feb. 10, 2015.
*Regeneron Pharmaceuticals, Inc.* v. *Merus B.V.*, Declaration of Aaron D. Resetarits, Esq. in Support of Merus's Motion for Sanctions Pursuant to Fed. R. Civ. P. 37 and/or to Compel Regeneron Pharmaceuticals, Inc. To Comply with the Court's Waiver Order, dated Feb. 10, 2015.
*Regeneron Pharmaceuticals, Inc.* v. *Merus B.V.*, Regeneron's Opposition to Merus's Motion Seeking an Adverse Inference of Inequitable Conduct, dated Feb. 17, 2015.
*Regeneron Pharmaceuticals, Inc.* v. *Merus B.V.*, Declaration of Michael E. Furrow in Support of Regeneron's Opposition to Merus's Motion Seeking an Adverse Inference of Inequitable Conduct, dated Feb. 17, 2015.
*Regeneron Pharmaceuticals, Inc.* v. *Merus B.V.*, Merus B.V.'s Reply in Support of its Motion for Sanctions and/or to Compel Regeneron Pharmaceuticals, Inc. to Comply with the Court's Waiver Order, dated Feb. 19, 2015.
*Regeneron Pharmaceuticals, Inc.* v. *Merus B.V.*, Declaration of Peter B. Silverman, esq. in Support of Merus's Reply in Support of its Motion for Sanctions and/or to Compel Regeneron Pharmaceuticals, Inc. to Comply with the Court's Waiver Order, dated Feb. 19, 2015.
*Regeneron Pharmaceuticals, Inc.* v. *Merus B.V.*, Joint Stipulation and [Proposed] Order of Invalidity and Non-Infringement of U.S. Pat. No. 8,502,018, dated Feb. 24, 2015.
*Regeneron Pharmaceuticals, Inc.* v. *Merus B.V.*, Memorandum Decision and Order, dated Feb. 25, 2015.
*Regeneron Pharmaceuticals, Inc.* v. *Merus B.V.*, Order Adjusting the Trial Schedule, dated Mar. 12, 2015.
*Regeneron Pharmaceuticals, Inc.* v. *Merus B.V.*, Regeneron Pharmaceuticals, Inc.'s Notice of Motion to Exclude the Testimony of John Doll, dated Apr. 7, 2015.
*Regeneron Pharmaceuticals, Inc.* v. *Merus B.V.*, Memorandum in Support of Regeneron Pharmaceutical Inc.'s Motion to Exclude the Testimony of John Doll, dated Apr. 7, 2015.
*Regeneron Pharmaceuticals, Inc.* v. *Merus B.V.*, Declaration of Michael E. Furrow in Support of Regeneron Pharmaceuticals, Inc.'s Motion to Exclude the Testimony of John Doll, dated Apr. 7, 2015.
*Regeneron Pharmaceuticals, Inc.* v. *Merus B.V.*, Order regarding Schedule, dated Apr. 17, 2015.
*Regeneron Pharmaceuticals, Inc.* v. *Merus B.V.*, Merus B.V.'s Response to Regeneron Pharmaceuticals, Inc.'s Motion to Exclude the Testimony of John Doll, dated Apr. 20, 2015.
*Regeneron Pharmaceuticals, Inc.* v. *Merus B.V.*, Declaration of Aaron D. Resetarits, Esq. in Support of Merus's Response to

(56) References Cited

OTHER PUBLICATIONS

Regeneron Pharmaceuticals, Inc.'s Motion to Exclude the Testimony of John Doll, dated Apr. 20, 2015.
*Regeneron Pharmaceuticals, Inc. v. Merus B.V.*, Order Ruling on Motion to Preclude the Testimony of John Doll, dated Apr. 27, 2015.
*Regeneron Pharmaceuticals, Inc. v. Merus B.V.*, Order regarding May 1, 2015 Teleconference with Parties, dated May 1, 2015.
*Regeneron Pharmaceuticals, Inc. v. Merus B.V.*, Merus B.V.'s Notice of Motion to Exclude Expert Opinions and Testimony Containing Improper Legal Conclusions that Defy the Court's Claim Construction Order and Law of the Case, and Opine on the Law, and on Intent, dated May 5, 2015.
*Regeneron Pharmaceuticals, Inc. v. Merus B.V.*, Merus's B.V.'s Motion and Supporting Memorandum to Exclude Regeneron's Expert Opinions that Contradict the Court's Claim Construction, and Opine on Intent and the Law, dated May 5, 2015.
*Regeneron Pharmaceuticals, Inc. v. Merus B.V.*, Declaration of Peter B. Silverman, Esq. in Support of Merus's Motion to Exclude Expert Opinions and Testimony Containing Improper Legal Conclusions that Defy the Court's Claim Construction Order and Law of the Case, and Opine on the Law, and on Intent, dated May 5, 2015.
*Regeneron Pharmaceuticals, Inc. v. Merus B.V.*, Merus B.V.'s Notice of Motion in Limine Nos. One and Two Concerning (1) Admissibility of Regeneron's Outside Counsel Notes; and (2) In Camera Review of Redacted Documents, dated May 8, 2015.
*Regeneron Pharmaceuticals, Inc. v. Merus B.V.*, Declaration of Saunak K. Desai in Support of Merus's Motion in Limine Nos. One and Two, dated May 8, 2015.
*Regeneron Pharmaceuticals, Inc. v. Merus B.V.*, Amended Declaration of Peter B. Silverman in Support of Merus's Motion to Exclude Expert Opinions and Testimony Containing Improper Legal Conclusions, dated Apr. 23, 2015.
*Regeneron Pharmaceuticals, Inc. v. Merus B.V.*, Regeneron's Opposition to Merus B.V.'s Motion to Exclude, dated May 12, 2015.
*Regeneron Pharmaceuticals, Inc. v. Merus B.V.*, Declaration of Christopher P. Borello in Support of Regeneron's Opposition to Merus B.V.'s Motion to Exclude, dated May 12, 2015.
*Regeneron Pharmaceuticals, Inc. v. Merus B.V.*, Order, dated May 15, 2015.
*Regeneron Pharmaceuticals, Inc. v. Merus B.V.*, Regeneron's Opposition to Merus B.V.'s Motion in Limine Nos. One and Two, dated May 15, 2015.
*Regeneron Pharmaceuticals, Inc. v. Merus B.V.*, Declaration of Christopher P. Borello in Support of Regeneron's Opposition to Merus B.V.'s Motion in Limine Nos. One and Two, dated May 15, 2015.
*Regeneron Pharmaceuticals, Inc. v. Merus B.V.*, Merus B.V.'s Reply in Support of its Motion to Exclude Regeneron's Expert Opinions that Contradict the Court's Claim Construction, and Opine on Intent and the Law, dated May 19, 2015.
*Regeneron Pharmaceuticals, Inc. v. Merus B.V.*, Declaration of Saunak K. Desai in Support of Merus B.V.'s Reply in Support of its Motion to Exclude Regeneron's Effect Opinions that Contradict the Court's Claim Construction, and Opine on Intent and the Law, dated May 19, 2015.
*Regeneron Pharmaceuticals, Inc. v. Merus B.V.*, Declaration of Peter B. Silverman in Support of Merus B.V.'s Pretrial Brief, dated May 19, 2015.
*Regeneron Pharmaceuticals, Inc. v. Merus B.V.*, Merus B.V.'s Pretrial Brief, dated May 19, 2015.
*Regeneron Pharmaceuticals, Inc. v. Merus B.V.*, Order ruling on Motion to Preclude the Testimony of John Doll, dated May 20, 2015.
*Regeneron Pharmaceuticals, Inc. v. Merus B.V.*, Notice of Regeneron's Renewed Motion to Exclude Testimony of John Doll, dated May 20, 2015.

*Regeneron Pharmaceuticals, Inc. v. Merus B.V.*, Memo in Support of Regeneron's Renewed Motion to Exclude Testimony of John Doll, dated May 21, 2015.
*Regeneron Pharmaceuticals, Inc. v. Merus B.V.*, Declaration of Michael E. Furrow in Support of Regeneron's Renewed Motion to Exclude Testimony of John Doll, dated May 20, 2015.
*Regeneron Pharmaceuticals, Inc. v. Merus B.V.*, Merus's Letter Opposing Renewed Motion to Exclude Testimony of John Doll, dated May 21, 2015.
*Regeneron Pharmaceuticals, Inc. v. Merus B.V.*, Merus B.V.'s Notice of Motion in Limine Nos. Three to Eight Concerning Matters of Law, Evidence, and Privilege, dated May 21, 2015.
*Regeneron Pharmaceuticals, Inc. v. Merus B.V.*, Merus B.V.'s Omnibus Motions in Limine Concerning Matters of Law, Evidence, and Privilege, dated May 21, 2015.
*Regeneron Pharmaceuticals, Inc. v. Merus B.V.*, Declaration of Peter B. Silverman in Support of Merus B.V.'s Motion in Limine Nos. Three to Eight, Concerning Matters of Law, Evidence, and Privilege, dated May 21, 2015.
*Regeneron Pharmaceuticals, Inc. v. Merus B.V.*, Declaration of Michael E. Furrow in Support of Regeneron's Trial Brief, May 26, 2015.
*Regeneron Pharmaceuticals, Inc. v. Merus B.V.*, Regeneron's Trial Brief, dated May 26, 2015.
*Regeneron Pharmaceuticals, Inc. v. Merus B.V.*, Declaration of Michael E. Furrow in Support of Regeneron's Opposition to Merus's Omnibus Motions in Limine Concerning Matters of Law, Evidence, and Privilege, dated May 28, 2015.
*Regeneron Pharmaceuticals, Inc. v. Merus B.V.*, Affidavit of Robert L. Stoll on Behalf of Regeneron Pharmaceuticals, Inc., dated May 29, 2015.
*Regeneron Pharmaceuticals, Inc. v. Merus B.V.*, Affidavit of Brendan Jones, Ph.D. on Behalf of Regeneron Pharmaceuticals, Inc., dated May 29, 2015.
*Regeneron Pharmaceuticals, Inc. v. Merus B.V.*, Affidavit of Donald R. Ware on Behalf of Regeneron Pharmaceuticals, Inc., dated May 29, 2015.
*Regeneron Pharmaceuticals, Inc. v. Merus B.V.*, Affidavit of Tor E. Smeland, Ph.D., dated May 29, 2015.
*Regeneron Pharmaceuticals, Inc. v. Merus B.V.*, Joint Letter Regarding Deposition Designations, dated May 31, 2015.
*Regeneron Pharmaceuticals, Inc. v. Merus B.V.*, Merus B.V.'s Emergency Motion to Strike, dated Jun. 1, 2015.
*Regeneron Pharmaceuticals, Inc. v. Merus B.V.*, Declaration of Peter B. Silverman in Support of Merus B.V.'s Emergency Motion to Strike, dated Jun. 1, 2015.
*Regeneron Pharmaceuticals, Inc. v. Merus B.V.*, Merus B.V.'s Emergency Motion to Strike Improper Expert Opinions and Trial Affidavits, dated Jun. 2, 2015.
*Regeneron Pharmaceuticals, Inc. v. Merus B.V.*, Declaration of Peter B. Silverman in Support of Merus B.V.'s Motion to Strike Improper Expert Opinions and Trial Affidavits, dated Jun. 2, 2015.
*Regeneron Pharmaceuticals, Inc. v. Merus B.V.*, Regeneron Letter to Court regarding Merus's Emergency Motion to Strike, dated Jun. 2, 2015.
*Regeneron Pharmaceuticals, Inc. v. Merus B.V.*, Order regarding Motions in limine, dated Jun. 4, 2015.
*Regeneron Pharmaceuticals, Inc. v. Merus B.V.*, Regeneron's Opposition to Merus B.V.'s Emergency Motion to Strike Improper Expert Opinions and Trial Affidavits, dated Jun. 5, 2015.
*Regeneron Pharmaceuticals, Inc. v. Merus B.V.*, Declaration of Brendan M. O'Malley in Support of Regeneron's Opposition to Merus B.V.'s Emergency Motion to Strike Improper Expert Opinions and Trial Affidavits, dated Jun. 5, 2015.
*Regeneron Pharmaceuticals, Inc. v. Merus B.V.*, Declaration of Michael E. Furrow in Support of Regeneron's Opposition to Merus's Emergency Motion to Strike Portions of Dr. Smeland's Testimony, dated Jun. 5, 2015.
*Regeneron Pharmaceuticals, Inc. v. Merus B.V.*, Merus B.V.'s Reply Brief in Support of its Emergency Motion to Strike, dated Jun. 7, 2015.

(56) References Cited

OTHER PUBLICATIONS

*Regeneron Pharmaceuticals, Inc.* v. *Merus B.V.*, Declaration of Peter B. Silverman in Support of Merus B.V.'s Reply Brief in Support of its Emergency Motion to Strike, dated Jun. 7, 2015.
*Regeneron Pharmaceuticals, Inc.* v. *Merus B.V.*, Order regarding Regeneron USB Drive Containing Docs on its Privilege, dated Jun. 9, 2015.
*Regeneron Pharmaceuticals, Inc.* v. *Merus B.V.*, Order regarding Certain Scheduling Matters, dated Jun. 16, 2015.
*Regeneron Pharmaceuticals, Inc.* v. *Merus B.V.*, Regeneron Letter to Court regarding Briefing on Privilege Waiver Issue, dated Jun. 16, 2015.
*Regeneron Pharmaceuticals, Inc.* v. *Merus B.V.*, Regeneron Letter to Court regarding List of Exhibits, dated Jun. 16, 2015.
*Regeneron Pharmaceuticals, Inc.* v. *Merus B.V.*, Merus B.V.'s List of Exhibits to be Offered by Merus for Trial Days 1-5, dated Jun. 16, 2015.
*Regeneron Pharmaceuticals, Inc.* v. *Merus B.V.*, Memo Endorsement Regeneron's Letter regarding Privilege Waiver, dated Jun. 16, 2015.
*Regeneron Pharmaceuticals, Inc.* v. *Merus B.V.*, Merus B.V.'s List of Exhibits to be Offered by Merus for Trial in Connection with Deposition Designations, dated Jun. 17, 2015.
*Regeneron Pharmaceuticals, Inc.* v. *Merus B.V.*, Order regarding exhibit lists, dated Jun. 19, 2015.
*Regeneron Pharmaceuticals, Inc.* v. *Merus B.V.*, Regeneron's Revised Exhibit List, dated Jun. 19, 2015.
*Regeneron Pharmaceuticals, Inc.* v. *Merus B.V.*, Letter from Merus to Court regarding Clarification of Exhibit List, dated Jun. 22, 2015.
*Regeneron Pharmaceuticals, Inc.* v. *Merus B.V.*, Memo Endorsement regarding Letter filed by Merus, dated Jun. 23, 2015.
*Regeneron Pharmaceuticals, Inc.* v. *Merus B.V.*, Merus B.V.'s Post Trial Brief on Materiality, dated Jun. 30, 2015.
*Regeneron Pharmaceuticals, Inc.* v. *Merus B.V.*, Merus B.V.'s Post Trial Brief Addressing Regeneron's Discovery and Waiver Misconduct, dated Jul. 7, 2015.
*Regeneron Pharmaceuticals, Inc.* v. *Merus B.V.*, Declaration of Aaron D. Resetarits in Support of Merus B.V.'s Post-Trial Brief Addressing Regeneron's Discovery and Waiver Misconduct, dated Jul. 7, 2015.
*Regeneron Pharmaceuticals, Inc.* v. *Merus B.V.*, Declaration of Susanne L. Flanders in Support of Regeneron's Responsive Brief on Materiality, dated Jul. 17, 2015.
*Regeneron Pharmaceuticals, Inc.* v. *Merus B.V.*, Regeneron's Responsive Brief on Materiality, dated Jul. 17, 2015.
*Regeneron Pharmaceuticals, Inc.* v. *Merus B.V.*, Declaration of Christopher P. Borello in Support of Regeneron's Brief Opposing Merus's Motion Seeking Preclusion and Sanctions and Requesting Affirmative Remedies to Mitigate Prejudice to Regeneron, dated Jul. 21, 2015.
*Regeneron Pharmaceuticals, Inc.* v. *Merus B.V.*, Regeneron's Brief Opposing Merus's Motion Seeking Preclusion and Sanctions, and Requesting Affirmative Remedies to Mitigate Prejudice to Regeneron, dated Jul. 21, 2015.
*Regeneron Pharmaceuticals, Inc.* v. *Merus B.V.*, Merus B.V.'s Post Trial Reply Brief on Materiality, dated Jul. 28, 2015.
*Regeneron Pharmaceuticals, Inc.* v. *Merus B.V.*, Declaration of Aaron D. Resetarits in Support of Merus B.V.'s Post-Trial Reply Brief Addressing Regeneron's Discovery and Waiver Misconduct, dated Jul. 30, 2015.
*Regeneron Pharmaceuticals, Inc.* v. *Merus B.V.*, Merus B.V.'s Post-Trial Reply Brief Addressing Regeneron's Discovery and Waiver Misconduct, dated Jul. 30, 2015.
*Regeneron Pharmaceuticals, Inc.* v. *Merus B.V.*, Memorandum Decision and Order, dated Aug. 6, 2015.
*Regeneron Pharmaceuticals, Inc.* v. *Merus B.V.*, Letter to Judge regarding Regeneron's Motion for Leave to Amend its Infringement Contentions, dated Sep. 15, 2014.
*Regeneron Pharmaceuticals, Inc.* v. *Merus B.V.*, Regeneron Letter to Court regarding Court's inquiry, dated Aug. 25, 2015.
*Regeneron Pharmaceuticals, Inc.* v. *Merus B.V.*, Order, dated Oct. 22, 2015.
*Regeneron Pharmaceuticals, Inc.* v. *Merus B.V.*, Letter to Court from Merus, dated Oct. 26, 2015.
*Regeneron Pharmaceuticals, Inc.* v. *Merus B.V.*, Letter to Court from Regeneron, dated Oct. 29, 2015.
*Regeneron Pharmaceuticals, Inc.* v. *Merus B.V.*, Letter to Court from Merus, dated Oct. 2015.
*Regeneron Pharmaceuticals, Inc.* v. *Merus B.V.*, Order, dated Oct. 30, 2015.
*Regeneron Pharmaceuticals, Inc.* v. *Merus B.V.*, Final Inequitable Conduct Opinion, dated Nov. 2, 2015.
*Regeneron Pharmaceuticals, Inc.* v. *Merus B.V.*, Opinion and Order, dated Nov. 2, 2015.
*Regeneron Pharmaceuticals, Inc.* v. *Merus B.V.*, Merus Letter to Court in Response to Regeneron Letter, dated Aug. 26, 2015.
*Regeneron Pharmaceuticals, Inc.* v. *Merus B.V.*, Regeneron Letter to Court regarding Court's Nov. 2 Order, dated Nov. 16, 2015.
*Regeneron Pharmaceuticals, Inc.* v. *Merus B.V.*, Memo Endorsement, dated Nov. 18, 2015.
*Regeneron Pharmaceuticals, Inc.* v. *Merus B.V.*, Final Judgment, dated Nov. 18, 2015.
*Regeneron Pharmaceuticals, Inc.* v. *Merus B.V.*, Merus B.V.'s Notice of Motion for Attorneys' Fees, Experts' Fees, and Costs, dated Nov. 16, 2015.
*Regeneron Pharmaceuticals, Inc.* v. *Merus B.V.*, Regeneron Letter to Court in response to Merus's letter dated Nov. 16, 2015, dated Nov. 17, 2015.
*Regeneron Pharmaceuticals, Inc.* v. *Merus B.V.*, Memo in Support of Motion for Fees, dated Nov. 16, 2015.
*Regeneron Pharmaceuticals, Inc.* v. *Merus B.V.*, Merus Letter concerning Proposed Order of Judgment, dated Nov. 16, 2015.
*Regeneron Pharmaceuticals, Inc.* v. *Merus B.V.*, *Regeneron* v. *Kymab* —Proceedings, dated Nov. 19, 2015.
*Regeneron Pharmaceuticals, Inc.* v. *Merus B.V.*, Exhibit Minutes of Oral Proceedings, dated Nov. 18, 2015.
*Regeneron Pharmaceuticals, Inc.* v. *Kymab Limited and Novo Nordisk A/S*, First Expert Report of Sir Martin Evans, dated Oct. 6, 2014.
*Regeneron Pharmaceuticals, Inc.* v. *Kymab Limited and Novo Nordisk A/S*, First Expert Report of Hidde Ploegh, dated Oct. 6, 2015.
*Regeneron Pharmaceuticals, Inc.* v. *Kymab Limited and Novo Nordisk A/S*, Sir Martin Evans Reply Report, dated Nov. 3, 2015.
*Regeneron Pharmaceuticals, Inc.* v. *Kymab Limited and Novo Nordisk A/S*, Second Expert Report of Hidde Ploegh, dated Nov. 3, 2015.
*Regeneron Pharmaceuticals, Inc.* v. *Kymab Limited and Novo Nordisk A/S*, Third Expert Report of Sir Martin Evans, dated Nov. 12, 2015.
*Regeneron Pharmaceuticals, Inc.* v. *Kymab Limited and Novo Nordisk A/S*, Confidential Expert Report of Adrian Francis Stewart, dated Oct. 6, 2015.
*Regeneron Pharmaceuticals, Inc.* v. *Kymab Limited and Novo Nordisk A/S*, First Expert Report of Jonathan Howard, dated Oct. 6, 2015.
*Regeneron Pharmaceuticals, Inc.* v. *Kymab Limited and Novo Nordisk A/S*, Confidential Second Expert Report of Adrian Francis Stewart, dated Nov. 2, 2015.
*Regeneron Pharmaceuticals, Inc.* v. *Kymab Limited and Novo Nordisk A/S*, Second Expert Report of Jonathan Howard, dated Nov. 3, 2015.
*Regeneron Pharmaceuticals, Inc.* v. *Kymab Limited and Novo Nordisk A/S*, Third Expert Report of Adrian Francis Stewart, dated Nov. 17, 2015.
*Regeneron Pharmaceuticals, Inc.* v. *Kymab Limited and Novo Nordisk A/S*, Fourth Expert Report of Adrian Francis Stewart, dated Nov. 19, 2015.
*Regeneron Pharmaceuticals, Inc.* v. *Kymab Limited and Novo Nordisk A/S*, First Witness Statement of Anthony DeFranco, dated Oct. 2, 2015.

(56) References Cited

OTHER PUBLICATIONS

*Regeneron Pharmaceuticals, Inc. v. Kymab Limited and Novo Nordisk A/S*, First Witness Statement of Professor Isao Ishida, dated Sep. 3, 2015.
*Regeneron Pharmaceuticals, Inc. v. Kymab Limited and Novo Nordisk A/S*, First Witness Statement of Andrew Joseph Murphy, dated Oct. 2, 2015.
*Regeneron Pharmaceuticals, Inc. v. Kymab Limited and Novo Nordisk A/S*, First Witness Statement of George D Yancopoulos, dated Oct. 2, 2015.
*Regeneron Pharmaceuticals, Inc. v. Kymab Limited and Novo Nordisk A/S*, Second Witness Statement of Andrew Joseph Murphy, dated Nov. 3, 2015.
*Regeneron Pharmaceuticals, Inc. v. Kymab Limited and Novo Nordisk A/S*, Third Witness Statement of Andrew Joseph Murphy, dated Nov. 15, 2015.
"Astellas Licenses Regeneron's VelocImmune Technology for Discovering Human Monoclonal Antibodies," dated Mar. 30, 2007.
"AstraZeneca licenses Regeneron's VelocImmune technology for discovering human monoclonal antibodies," Drugs.com, retrieved from: https://www.drugs.com/news/astrazeneca-licenses-regeneron-s-velocimmune-technology-discovering-human-monoclonal-antibodies-5221.html, Feb. 5, 2007.
"Basic Primer Walking," DNA Sequencing Core, retrieved from: https://seqcore.brcf.med.umich.edu/doc/dnaseq/primerwalking. html, Nov. 21, 2015.
"Highlights of the 2007 AACR annual meeting," The Barnes Report, retrieved from: http://www.imakenews.com/barnesreport/e_article000807331.cfm?x=b11,0,w, Jan. 23, 2014.
"Mouse Genome Data Available in Public Databases," National Human Genome Research Institute, retrieved from: https://www.genome.gov/10002191/2001-release-mouse-genome-twothirds-sequenced/, Dec. 22, 2016.
"News in Brief," Nat Biotechnol, 25(6): 613-614 (2007).
"Regeneron and Columbia University Enter into a Strategic VelocImmune Agreement to Discover Human Monoclonal Antibodies," Business Wire, retrieved from: http://www.businesswire.com/news/google/20080916005336/en, Jan. 23, 2014.
"Regeneron partners VelocImmune with University of Texas," Elsevier Business Intelligence, retrieved from: http://www.elsevierbi.com/deals/200920210?p=1, Jan. 23, 2014.
"The life history of the mouse in genetics," Nature, 420: 510-511 (2002).
Aggarwal et al., "Novel site-specific DNA endonucleases," Curr Opin Struct Biol, 8: 19-25 (1998).
Anand, "Cloning into yeast artificial chromosomes," DNA Cloning 3, A Practical Approach, Chapter 4, pp. 112-114 (1995).
Biorad Gene Pulser II Electroporation System, Instruction Manual.
Blankenstein et al., "Immunoglobulin Vh region genes of the mouse are organized in overlapping clusters," Eur J Immunol, 17: 1351-1357 (1987).
Boren et al., "A simple and efficient method for making site-directed mutants, deletions, and fusions of large DNA such as P1 and BAC clones," Genome Res, 6: 1123-1130 (1996).
Bourdeau, et al., "Genome-wide Identification of high-affinity Estrogen Response Elements in Human and Mouse," Mol Endocrinol, 18(6): 1411-1417 (2004).
Call et al., "A Cre-lox recombination system for the targeted integration of circular yeast artificial chromosomes into embryonic stem cells," Human Mol Genet, 9(12): 1745-1751 (2000).
Catalano et al., "Virus DNA packaging: the strategy used by phage lambda," Mol Microbiol, 16(6): 1075-1066 (1995).
Certificate of Analysis, I-CeuI R0699S, New England BioLabs, expires Sep. 2014.
Certificate of Analysis, PI-SceI R0696S, New England BioLabs, expires Feb. 2015.
Cook et al., "A Map of the Human Immunoglobulin VH Locus Completed by Analysis of the Teleomeric Region of Chromosome 14q," Nat Genet, 7(2): 162-168 (1994).
Course Invitation for "Mastering Simple & Elegant DNA Engineering," dated Mar. 24-28, 2003.
Course Packet, "Red/ET Recombination: Cloning Without Restriction Enzymes, A Guide to Next Generation Cloning."
Cowan et al., "Targeting gene expression to endothelium in transgenic animals: a comparison of the human ICAM-2, PECAM-1 and endoglin promoters," Xenotransplantation, 10(3): 223-231 (2003).
D'Eustachio et al., "Mouse Chromosome 12," Mammal Gen, 8: S241-S257 (1998).
Denning et al., "New Frontiers in Gene Targeting and Cloning: Success, Application, and Challenges in Domestic Animals and Human Embryonic Stem Cells," Reproduction, 126: 1-11 (2003).
Dietrich et al., "A comprehensive genetic map of the mouse genome," Nature, 380: 149-152 (1996).
Duthell et al., "Characterization of the mouse Adeno-associated virus AAVS1 ortholog." J Virol, 78(16): 8917-21 (2004).
Eggan et al., "Hybrid vigor, fetal overgrowth, and viability of mice derived by nuclear cloning and tetraploid embryo complementation," PNAS, 98(11): 6209-6214 (2001).
Email from Joseph Sorrentino to Leonard Schleifer, George Yancopoulos, and Eric Brewster regarding GeneBridges, dated Feb. 25, 2003.
Endrizzi et al., "Genomic sequence analysis of the mouse Naip gene array," Genome Res, 10(8): 1095-1102 (2000).
Eppig et al., "Mouse genome informatics (MGI): reflecting on 25 years," Mamm Genome, 26: 272-284 (2015).
Eppig, "Electronic tools for accessing the mouse genome," Mouse Genetics and Transgenics: a practical approach, Chapter 7, pp. 171-183 (2000).
Extract from Fundamental Immunology, 4th Ed., Chapter 5, Figure 16, pp. 140 (1999).
Fan et al., "Gene content and function of the ancestral chromosome fusion site in human chromosome 2q13-2q14.1 and paralogous regions," Genome Res, 12(11): 1663-1672 (2002).
Feeney et al., "Dst4: a new, and probably the last, functional Dh gene in the BALB/c mouse," Immunogenet, 37: 217-221 (1993).
Fenske et al., "Long-curculating vectors for the systemic delivery of genes," Curr Opin Mol Ther, 3(2): 153-158 (2001).
Fox et al., "Fluorescent in situ hybridization (FISH) to mouse chromosomes," Mouse Genetics and Transgenics: a practical approach, Chapter 6B, pp. 154-169 (2000).
Frengen et al., "A modular, positive selection bacterial artificial chromosome vector with multiple cloning sites," Genomics, 58: 250-253 (1999).
Fujieda et al., "Direct evidence that gamma 1 and gamma 3 switching in human B cells is interleukin-10 dependent," Mol Immunol, 33(17-18): 1335-1343 (1996).
Fukita et al., "Somatic hypermutation in the heavy chain locus correlates with transcription," Immunity, 9: 105-114 (1998).
George et al., "Developmental and adult phenotyping directly from mutant embryonic stem cells," PNAS, 104(11): 4455-4460 (2007).
Glaser et al., "Current issues in mouse genome engineering," Nat Genet, 37(11): 1187-1193 (2005).
Gu et al., "Most peripheral B cells in mice are ligand selected," J Exp Med, 173: 1357-1371 (1991).
Hammer et al., "Genetic Engineering of Mammalian Embryos," J Anim Sci, 63(1): 269-278 (1986).
Hammer et al., "Spontaneous Inflammatory Disease in Transgenic Rats Expressing HLA-B27 and Human B2m: An animal model of HLA-B27-associated Human Disorders," Cell, 63(5): 1099-1112 (1990).
Hansen, "Kymab: More mAb diversity," BioCentury, the Bernstein Report on BioBusiness, Reprint from Feb. 27, 2012.
Honjo et al., "Content and organization of the murine v-region locus," Immunoglobulin Genes, 2nd Ed, pp. 71-76 (1995).
Huetz et al., "Targeted disruption of the Vh 81X gene: influence on the B cell repertoire," Eur J Immunol, 27: 307-314 (1997).
Jacks et al., "Effects of an Rb mutation in the Mouse," Nature, 359: 295-300 (1992).
Jaenisch et al., "Transgenic animals," Science, 240(4858): 1468-1474 (1988).

(56) References Cited

OTHER PUBLICATIONS

Kawasaki et al., "Evolutionary dynamics of the human immunoglobulin kappa locus and the germline repertoire of the v kappa genes," Eur J Immunol, 31: 1017-1028 (2001).
Knight, "Mouse genome effort 'on course,'" Nature, 411: 121 (2001).
Kobayashi et al., "The Minipig—A New Tool in Stem Cell Research, Advances in Mechanisms, Methods, and Models," Prof. Craig Atwood (ed.), InTech (2014).
Kohler et al., "Derivation of specific antibody-producing tissue culture and tumor lines by cell fusion," Eur J Immunol, 6(7): 511-519 (1976).
Kolb et al., "Selection-marker-free modification of the murine beta-casein gene using a Iox2272 [correction of Iox2722) site," Anal Biochem, 290(2): 260-271 (2001).
Lee et al., "A highly efficient *Escherichia coli*-based chromosome engineering system adapted for recombinogenic targeting and subcloning of BAC DNA," Genomics, 73: 56-65 (2001).
Lee et al., "Cross-referencing eukaryotic genomes: TIGR Orthologous Genes Alignments (TOGA)," Genome Res, 12(3): 493-502 (2002).
Lefranc et al., "The Human IGK Locus," The Immunoglobulin Factsbook, pp. 52-58 (2001).
Lonberg, "Human antibodies from transgenic animals," Nat Biotechnol, 23(9): 1117-1125 (2005).
Lonberg, "Human monoclonal antibodies from transgenic mice," Handb Exp Pharmacol, 181: 69-97 (2008).
Macdonald et al., "Velocigene technology extended to humanization of several megabases of complex gene loci," abstract, 1st International MUGEN Conference on Animal Models for Human Immunological Disease (2006).
Macdonald et al., "Velocigene technology extended to humanization of several megabases of complex gene loci," poster, 1st International MUGEN Conference on Animal Models for Human Immunological Disease (2006).
Mansour et al., "Disruption of the proto-oncogene int-2 in mouse embryo-derived stem cells: a general strategy for targeting mutations to non-selectable genes," Nature, 336: 348-352 (1988).
Matsuda et al., "Structure and physical map of 64 variable segments in the 3'0.8-megabase region of the human immunoglobulin heavy-chain locus," Nat Genet, 3(1): 88-94 (1993).
McCallister, "Still on the lookout," BioCentury, the Bernstein Report on BioBusiness, 21(48): A1, A13 (2013).
McMurry, et al., "Enhancer control of local accessibility to V(D)J recombinase," Mol Cell Biol, 17(8): 4553-4561 (1997).
Mejia et al., "Retrofitting vectors for *Escherichia coli*-based artificial chromosomes (PACs and PACs) with markers for transfection studies," Genome Res, 7: 179-186 (1997).
Mejia et al., "The assembly of large BACs by in vivo recombination," Genomics, 70: 165-170 (2000).
Merus MeMo—the ingenious mouse, datasheet, version: Dec. 2011.
Merus MeMo transgenic mouse, datasheet, version: Sep. 2012.
Merus presentation, Full Length Human IgG Bispecific Antibodies for Cancer Therapy, May 27, 2013.
Moens et al., "Defects in heart and lung development in compound heterozygotes for two different targeted mutations at the N-myc locus," Development, 119(2): 485-499 (1993).
Morrow et al., "Gene Targeting in mammalian cells by homologous recombination," Curr Opin Biotechnol, 4(5): 577-582 (1993).
Murphy et al., "Use of bacteriophage lambda recombination functions to promote gene replacement in *Escherichia coli*," J Bacteriol, 180(8): 2063-2071 (1998).
Murray et al., "Transgenic Animals in Agriculture," CAB International: Oxon, pp. 58-61 (1999).
Muyrers et al., "ET-Cloning: Think Recombination First," Genet Eng, 77-98 (2000).
Muyrers et al., "Point mutation of bacterial artificial chromosomes by ET recombination," EMBO reports, 1(3): 239-243 (2000).

Nagle, "Regeneron helps make Sanofi VeloImmune to its 'weak' pipeline," Outsourcing Pharma, retrieved from: http://www.outsourcing-pharma.com/content/view/print/325803, Nov. 10, 2013.
Nagy et al., "Cre recombinase: the universal reagent for genome tailoring," Genesis, 26: 99-109 (2000).
Nefedov et al., "Insertion of disease-causing mutations in BACs by homologous recombination in *Escherichia coli*," Nucleic Acid Res, 28(17): e79 (2000).
Nusbaum et al., "A YAC-based physical map of the mouse genome," Nat Genet, 22: 388-393 (1999).
Open Monoclonal Technology, Inc. presentation, "OmniRat, OmniMouse, and OmniFlic, naturally optimized human antibodies," dated Nov. 3, 2013.
Opposition to EP Patent 1360287: Statement of Andrew Murphy.
Opposition to EP Patent 2264163: Declaration from Dr. Andrew Murphy.
Opposition to EP Patent 2264163: Declaration from Dr. Lynn Macdonald.
Opposition to EP Patent 2264163: Declaration from Professor Hidde Ploegh.
Opposition to EP Patent 2264163: Declaration from Professor Kenan Murphy.
Opposition to EP Patent 2264163: Declaration from Professor Sir Martin Evans.
Opposition to EP Patent 2264163: Declaration from Professor Werner Muller.
Opposition to EP Patent 2264163: Merus Examination Response, dated Apr. 23, 2013.
Opposition to EP Patent 2264163: Regeneron's Response to Opposition, dated Dec. 30, 2016.
Orford et al., "Engineering EGFP reporter constructs into a 200 kb human beta-globin BAC clone using GET Recombination," Nucleic Acid Res, 28(18): e84 (2000).
Osoegawa et al., "Bacterial artificial chromosome libraries for mouse sequencing and functional analysis," Genome Res, 10(1): 116-128 (2000).
Peters et al., "Organization of mouse Iroquois homeobox genes in two clusters suggests a conserved regulation and function in vertebrate development," Genome Res, 10(10): 1453-1462 (2000).
Picciotto et al., "Using Knockout and Transgenic Mice to Study Neurophysiology and Behavior," Physiol Rev, 78(4): 1131-1163 (1998).
Platt et al., "New directions for organ transplantation," Nature, 392(6679 Suppl.): 11-17 (1998).
Potter et al., "Enhancer-dependent expression of human kappa immunoglobulin genes introduced into mouse pre-B lymphocytes by electroporation," PNAS, 81: 7161-7165 (1984).
Potter et al., "Transfection by electroporation," Curr Protoc Mol Biol, (2003).
Ramirez-Solis et al., "Gene targeting in embryonic stem cells," Meth Enzymol, 225: 855-878 (1993).
Reyrat et al., "Counterselectable markers: untapped tools for bacterial genetics and pathogenesis," Infect Immun, 66(9): 4011-4017 (1998).
Riblet et al., "Polymorphism and evolution of Igh-V gene families," Curr Top Microbiol Immunol, 127: 167-172 (1986).
Rideout et al., "Generation of mice from wild-type and targeted ES cells by nuclear cloning," Nat Genet, 24: 109-110 (2000).
Roach et al., "A New Embryonic Stem Cell Line from DBA/1IacJ Mice Allows Genetic Modification in a Murine Model of Human Inflammation," Exp Cell Res, 221(2): 520-525 (1995).
Sambrook et al., "Cre-loxP," Molecular Cloning: a Laboratory Manual, Chapter 4, pp. 4.82-4.85 (2001).
Sambrook et al., "Electroporation," Molecular Cloning: a Laboratory Manual, Chapter 16, pp. 16.54-16.57 (2001).
Sambrook et al., "Introduction," Molecular Cloning: a Laboratory Manual, Chapter 1, pp. 1.1-1.25 (2001).
Sambrook et al., "Introduction," Molecular Cloning: a Laboratory Manual, Chapter 4, pp. 4.1-4.8 (2001).
Sambrook et al., "Introduction," Molecular Cloning: a Laboratory Manual, Chapter 5, pp. 5.3 (2001).
Sambrook et al., "Introduction," Molecular Cloning: a Laboratory Manual, Chapter 6, pp. 6.3 (2001).

(56) References Cited

OTHER PUBLICATIONS

Sambrook et al., "Minimizing damage to large DNA molecules," Molecular Cloning: a Laboratory Manual, Chapter 2, pp. 2.110-2.111 (2001).
Sambrook et al., "Protocol 13: Preparation of DNA for pulsed-field gel electrophoresis: isolation of DNA from mammalian cells and tissues," Molecular Cloning: a Laboratory Manual, Chapter 5, pp. 5.61-5.64 (2001).
Sambrook et al., "Protocol 15: Restriction endonuclease digestion of DNA in agarose plugs," Molecular Cloning: a Laboratory Manual, Chapter 5, pp. 5.68-5.70 (2001).
Sambrook et al., "Protocol 19: Direct retrieval of DNA fragments from pulsed-field gels," Molecular Cloning: a Laboratory Manual, Chapter 5, pp. 5.83-5.85 (2001).
Sambrook et al., "Protocol 1: Generation of a library of randomly overlapping DNA inserts," Molecular Cloning: a Laboratory Manual, Chapter 12, pp. 12.11-12.13 (2001).
Sambrook et al., "Protocol 2: Isolation of high-molecular-weight DNA from mamalian cells using formamide," Molecular Cloning: a Laboratory Manual, Chapter 6, pp. 6.13-6.15 (2001).
Sambrook et al., "Protocol 5: DNA transfection by electroporation," Molecular Cloning: a Laboratory Manual, Chapter 16, pp. 6.33-6.36 (2001).
Sambrook et al., "Protocol 7: Working with bacterial artificial chromosomes," Molecular Cloning: a Laboratory Manual, Chapter 4, pp. 4.48-4.52 (2001).
Sambrook et al., "Real Time PCR," Molecular Cloning: a Laboratory Manual, Chapter 8, pp. 8.94-8.95 (2001).
Sauer, "Inducible gene targeting in mice using the Cre/lox system," Meth Enzymol, 14: 381-392 (1998).
Schindelhauer et al., "Efficient combination of large DNA in vitro: in gel site specific recombination (IGSSR) of PAC fragments containing alpha satellite DNA and the human HPRT gene locus," Nucleic Acid Res, 25(11): 2241-2243 (1997).
Sheng et al., "Transformation of *Escherichia coli* with large DNA molecules by electroporation," Nucleic Acid Res, 23(11): 1990-1996 (1995).
Spazierer et al., "Epiplakin gene analysis in mouse reveals a single exon encoding a 725-kDa protein with expression restricted to epithelial tissues," J Biol Chem, 278(34): 31657-31666 (2003).
Stevens et al., "VelocImmune: Humanization of immunoglobulin loci using VelociGene technology," abstract, 1st International MUGEN Conference on Animal Models for Human Immunological Disease (2006).
Stevens et al., "VelocImmune: Humanization of immunoglobulin loci using VelociGene technology," poster, 1st International MUGEN Conference on Animal Models for Human Immunological Disease (2006).
Stevens, "Human Antibody Discovery: VelocImmune—A novel platform," Pharma Focus Asia, 8: 72-74 (2008).
Tao et al., "Cloning and stable maintenance of DNA fragments over 300 kb in *Escherichia coli* with conventional plasmid-based vectors," Nucleic Acid Res, 26(21): 4901-4909 (1998).
Tatusov et al., "A genomic perspective on protein families," Science, 278(5338): 631-637 (1997).
Trucksis et al., "The vibrio cholerae genome contains two unique circular chromosomes," PNAS, 95: 14464-14469 (1998).
Ueda et al., "Establishment of Rat Embryonic Stem Cells and Making of Chimera Rats," PLoS One, 3(7): e2800 (2008).
Van Etten et al., "Radiation hybrid map of the mouse genome," Nat Genet, 22: 384-387 (1999).
Vasicek et al., "B-less: a strain of profoundly B cell-deficient mice expressing a human lambda transgene," J Exp Med, 175: 1169-1180 (1992).
Wade-Martins et al., "Long-term stability of large insert genomic DNA episomal shuttle vectors in human cells," Nucleic Acid Res, 27(7): 1674-1682 (1999).
Wall et al., "Pronuclear microinjection," Cloning Stem Cells, 3(4): 209-220 (2001).
Weigert et al., "The genetic control of antibody variable regions in the mouse," Sem Immunopathol, 1: 133-169 (1978).
Xu et al., "Structure of the bacteriophage lambda cohesive end site genetic analysis of the site (cosN) at which nicks are introduced by terminase," J Med Biol, 220: 281-292 (1991).
Yang et al., "Site-specific gene targeting in mouse embryonic stem cells with intact bacterial artificial chromosomes," Nat Biotechnol, 21: 447-451 (2003).
Zhang et al., "DNA cloning by homologous recombination in *Escherichia coli*," Nat Biotechnol, 18: 1314-1317 (2000).
Zhao, "A comprehensive BAC resource," Nucleic Acid Res, 29(1): 141-143 (2001).
Zhao, "Mouse BAC End Sequencing Project," Trans-NIH Mouse Initiative, retrieved from: http://www.nih.gov/science/models/mouse/resources/mouse_BACendseq.html, Oct. 30, 2015.
Zheng et al., "Engineering mouse chromosomes with Cre-loxP: Range, Efficiency, and Somatic Applications," Mol Cell Biol, 20(2): 648-655 (2000).

\* cited by examiner

FIGURE 3A

```
         10         20         30         40         50         60
CCCCGGGCTT CCTGTTCTAA TAAGAATACC TCCTAGGTCC CCCATGGGCT AACCTCATCT
GGGGCCCGAA GGACAAGATT ATTCTTATGG AGGATCCAGG GGGTACCCGA TTGGAGTAGA 70         80         90        100        110        120
TTGGTACTCA ACAGGGGTCT TCTTTATGAG CTTCGGACCA GCTCTTTTGA TGTGGCAGGG
AACCATGAGT TGTCCCCAGA AGAAATACTC GAAGCCTGGT CGAGAAAACT ACACCGTCCC 130        140        150        160        170        180
ACTGACCCTG GGTGGGGAAG CCACTCAGTG CATGACCCCA GCTGGTTCAC CACATATACC
TGACTGGGAC CCACCCCTTC GGTGAGTCAC GTACTGGGGT CGACCAAGTG GTGTATATGG 190        200        210        220        230
ACATACTTTT CTTGCAGGTC TGGGACACAG C ATG CCC CGG GGC CCA GTG GCT GCC
TGTATGAAAA GAACGTCCAG ACCCTGTGTC G TAC GGG GCC CCG GGT CAC CGA CGG
                                   Met Pro Arg Gly Pro Val Ala Ala>

240        250        260        270        280
TTA CTC CTG CTG ATT CTC CAT GGA GCT TGG AGC TGC CTG GAC CTC ACT
AAT GAG GAC GAC TAA GAG GTA CCT CGA ACC TCG ACG GAC CTG GAG TGA
Leu Leu Leu Leu Ile Leu His Gly Ala Trp Ser Cys Leu Asp Leu Thr>

290        300        310        320        330
TGC TAC ACT GAC TAC CTC TGG ACC ATC ACC TGT GTC CTG GAG ACA CGG
ACG ATG TGA CTG ATG GAG ACC TGG TAG TGG ACA CAG GAC CTC TGT GCC
Cys Tyr Thr Asp Tyr Leu Trp Thr Ile Thr Cys Val Leu Glu Thr Arg>

340        350        360        370
AGC CCC AAC CCC AGC ATA CTC AGT CTC ACC TGG CAA GAT GAA TAT GAG
TCG GGG TTG GGG TCG TAT GAG TCA GAG TGG ACC GTT CTA CTT ATA CTC
Ser Pro Asn Pro Ser Ile Leu Ser Leu Thr Trp Gln Asp Glu Tyr Glu>

380        390        400        410        420
GAA CTT CAG GAC CAA GAG ACC TTC TGC AGC CTA CAC AAG TCT GGC CAC
CTT GAA GTC CTG GTT CTC TGG AAG ACG TCG GAT GTG TTC AGA CCG GTG
Glu Leu Gln Asp Gln Glu Thr Phe Cys Ser Leu His Lys Ser Gly His>

430        440        450        460        470
AAC ACC ACA CAT ATA TGG TAC ACG TGC CAT ATG CGC TTG TCT CAA TTC
TTG TGG TGT GTA TAT ACC ATG TGC ACG GTA TAC GCG AAC AGA GTT AAG
Asn Thr Thr His Ile Trp Tyr Thr Cys His Met Arg Leu Ser Gln Phe>

480        490        500        510        520
CTG TCC GAT GAA GTT TTC ATT GTC AAC GTG ACG GAC CAG TCT GGC AAC
GAC AGG CTA CTT CAA AAG TAA CAG TTG CAC TGC CTG GTC AGA CCG TTG
Leu Ser Asp Glu Val Phe Ile Val Asn Val Thr Asp Gln Ser Gly Asn>

530        540        550        560        570
AAC TCC CAA GAG TGT GGC AGC TTT GTC CTG GCT GAG AGC ATC AAG CCA
TTG AGG GTT CTC ACA CCG TCG AAA CAG GAC CGA CTC TCG TAG TTC GGT
Asn Ser Gln Glu Cys Gly Ser Phe Val Leu Ala Glu Ser Ile Lys Pro>
```

FIGURE 3B

```
         580           590           600           610
   GCT CCC CCC TTG AAC GTG ACT GTG GCC TTC TCA GGA CGC TAT GAT ATC
   CGA GGG GGG AAC TTG CAC TGA CAC CGG AAG AGT CCT GCG ATA CTA TAG
   Ala Pro Pro Leu Asn Val Thr Val Ala Phe Ser Gly Arg Tyr Asp Ile>

620           630           640           650           660
   TCC TGG GAC TCA GCT TAT GAC GAA CCC TCC AAC TAC GTG CTG AGA GGC
   AGG ACC CTG AGT CGA ATA CTG CTT GGG AGG TTG ATG CAC GAC TCT CCG
   Ser Trp Asp Ser Ala Tyr Asp Glu Pro Ser Asn Tyr Val Leu Arg Gly>

670           680           690           700           710
   AAG CTA CAA TAT GAG CTG CAG TAT CGG AAC CTC AGA GAC CCC TAT GCT
   TTC GAT GTT ATA CTC GAC GTC ATA GCC TTG GAG TCT CTG GGG ATA CGA
   Lys Leu Gln Tyr Glu Leu Gln Tyr Arg Asn Leu Arg Asp Pro Tyr Ala>

720           730           740           750           760
   GTG AGG CCG GTG ACC AAG CTG ATC TCA GTG GAC TCA AGA AAC GTC TCT
   CAC TCC GGC CAC TGG TTC GAC TAG AGT CAC CTG AGT TCT TTG CAG AGA
   Val Arg Pro Val Thr Lys Leu Ile Ser Val Asp Ser Arg Asn Val Ser>

770           780           790           800           810
   CTT CTC CCT GAA GAG TTC CAC AAA GAT TCT AGC TAC CAG CTG CAG ATG
   GAA GAG GGA CTT CTC AAG GTG TTT CTA AGA TCG ATG GTC GAC GTC TAC
   Leu Leu Pro Glu Glu Phe His Lys Asp Ser Ser Tyr Gln Leu Gln Met>

820           830           840           850
   CGG GCA GCG CCT CAG CCA GGC ACT TCA TTC AGG GGG ACC TGG AGT GAG
   GCC CGT CGC GGA GTC GGT CCG TGA AGT AAG TCC CCC TGG ACC TCA CTC
   Arg Ala Ala Pro Gln Pro Gly Thr Ser Phe Arg Gly Thr Trp Ser Glu>

860           870           880           890           900
   TGG AGT GAC CCC GTC ATC TTT CAG ACC CAG GCT GGG GAG CCC GAG GCA
   ACC TCA CTG GGG CAG TAG AAA GTC TGG GTC CGA CCC CTC GGG CTC CGT
   Trp Ser Asp Pro Val Ile Phe Gln Thr Gln Ala Gly Glu Pro Glu Ala>

910           920           930           940           950
   GGC TGG GAC CCT CAC ATG CTG CTG CTG GCT GTC TTG ATC ATT GTC
   CCG ACC CTG GGA GTG TAC GAC GAC GAC CGA CAG AAC TAG TAA CAG
   Gly Trp Asp Pro His Met Leu Leu Leu Leu Ala Val Leu Ile Ile Val>

960           970           980           990           1000
   CTG GTT TTC ATG GGT CTG AAG ATC CAC CTG CCT TGG AGG CTA TGG AAA
   GAC CAA AAG TAC CCA GAC TTC TAG GTG GAC GGA ACC TCC GAT ACC TTT
   Leu Val Phe Met Gly Leu Lys Ile His Leu Pro Trp Arg Leu Trp Lys>

1010          1020          1030          1040          1050
   AAG ATA TGG GCA CCA GTG CCC ACC CCT GAG AGT TTC TTC CAG CCC CTG
   TTC TAT ACC CGT GGT CAC GGG TGG GGA CTC TCA AAG AAG GTC GGG GAC
   Lys Ile Trp Ala Pro Val Pro Thr Pro Glu Ser Phe Phe Gln Pro Leu>
```

FIGURE 3C

```
         1060          1070          1080          1090
TAC AGG GAG CAC AGC GGG AAC TTC AAG AAA TGG GTT AAT ACC CCT TTC
ATG TCC CTC GTG TCG CCC TTG AAG TTC TTT ACC CAA TTA TGG GGA AAG
Tyr Arg Glu His Ser Gly Asn Phe Lys Lys Trp Val Asn Thr Pro Phe>

1100          1110          1120          1130          1140
ACG GCC TCC AGC ATA GAG TTG GTG CCA CAG AGT TCC ACA ACA ACA TCA
TGC CGG AGG TCG TAT CTC AAC CAC GGT GTC TCA AGG TGT TGT TGT AGT
Thr Ala Ser Ser Ile Glu Leu Val Pro Gln Ser Ser Thr Thr Thr Ser>

1150          1160          1170          1180          1190
GCC TTA CAT CTG TCA TTG TAT CCA GCC AAG GAG AAG AAG TTC CCG GGG
CGG AAT GTA GAC AGT AAC ATA GGT CGG TTC CTC TTC TTC AAG GGC CCC
Ala Leu His Leu Ser Leu Tyr Pro Ala Lys Glu Lys Lys Phe Pro Gly>

1200          1210          1220          1230          1240
CTG CCG GGT CTG GAA GAG CAA CTG GAG TGT GAT GGA ATG TCT GAG CCT
GAC GGC CCA GAC CTT CTC GTT GAC CTC ACA CTA CCT TAC AGA CTC GGA
Leu Pro Gly Leu Glu Glu Gln Leu Glu Cys Asp Gly Met Ser Glu Pro>

1250          1260          1270          1280          1290
GGT CAC TGG TGC ATA ATC CCC TTG GCA GCT GGC CAA GCG GTC TCA GCC
CCA GTG ACC ACG TAT TAG GGG AAC CGT CGA CCG GTT CGC CAG AGT CGG
Gly His Trp Cys Ile Ile Pro Leu Ala Ala Gly Gln Ala Val Ser Ala>

1300          1310          1320          1330
TAC AGT GAG GAG AGA GAC CGG CCA TAT GGT CTG GTG TCC ATT GAC ACA
ATG TCA CTC CTC TCT CTG GCC GGT ATA CCA GAC CAC AGG TAA CTG TGT
Tyr Ser Glu Glu Arg Asp Arg Pro Tyr Gly Leu Val Ser Ile Asp Thr>

1340          1350          1360          1370          1380
GTG ACT GTG GGA GAT GCA GAG GGC CTG TGT GTC TGG CCC TGT AGC TGT
CAC TGA CAC CCT CTA CGT CTC CCG GAC ACA CAG ACC GGG ACA TCG ACA
Val Thr Val Gly Asp Ala Glu Gly Leu Cys Val Trp Pro Cys Ser Cys>

1390          1400          1410          1420          1430
GAG GAT GAT GGC TAT CCA GCC ATG AAC CTG GAT GCT GGC AGA GAG TCT
CTC CTA CTA CCG ATA GGT CGG TAC TTG GAC CTA CGA CCG TCT CTC AGA
Glu Asp Asp Gly Tyr Pro Ala Met Asn Leu Asp Ala Gly Arg Glu Ser>

1440          1450          1460          1470          1480
GGT CCT AAT TCA GAG GAT CTG CTC TTG GTC ACA GAC CCT GCT TTT CTG
CCA GGA TTA AGT CTC CTA GAC GAG AAC CAG TGT CTG GGA CGA AAA GAC
Gly Pro Asn Ser Glu Asp Leu Leu Leu Val Thr Asp Pro Ala Phe Leu>

1490          1500          1510          1520          1530
TCT TGT GGC TGT GTC TCA GGT AGT GGT CTC AGG CTT GGG GGC TCC CCA
AGA ACA CCG ACA CAG AGT CCA TCA CCA GAG TCC GAA CCC CCG AGG GGT
Ser Cys Gly Cys Val Ser Gly Ser Gly Leu Arg Leu Gly Gly Ser Pro>
```

Figure 3D

```
         1540           1550           1560           1570
  GGC AGC CTA CTG GAC AGG TTG AGG CTG TCA TTT GCA AAG GAA GGG GAC
  CCG TCG GAT GAC CTG TCC AAC TCC GAC AGT AAA CGT TTC CTT CCC CTG
  Gly Ser Leu Leu Asp Arg Leu Arg Leu Ser Phe Ala Lys Glu Gly Asp>

1580           1590           1600           1610           1620
  TGG ACA GCA GAC CCA ACC TGG AGA ACT GGG TCC CCA GGA GGG GGC TCT
  ACC TGT CGT CTG GGT TGG ACC TCT TGA CCC AGG GGT CCT CCC CCG AGA
  Trp Thr Ala Asp Pro Thr Trp Arg Thr Gly Ser Pro Gly Gly Gly Ser>

1630           1640           1650           1660           1670
  GAG AGT GAA GCA GGT TCC CCC CCT GGT CTG GAC ATG GAC ACA TTT GAC
  CTC TCA CTT CGT CCA AGG GGG GGA CCA GAC CTG TAC CTG TGT AAA CTG
  Glu Ser Glu Ala Gly Ser Pro Pro Gly Leu Asp Met Asp Thr Phe Asp>

1680           1690           1700           1710           1720
  AGT GGC TTT GCA GGT TCA GAC TGT GGC AGC CCC GTG GAG ACT GAT GAA
  TCA CCG AAA CGT CCA AGT CTG ACA CCG TCG GGG CAC CTC TGA CTA CTT
  Ser Gly Phe Ala Gly Ser Asp Cys Gly Ser Pro Val Glu Thr Asp Glu>

1730           1740           1750           1760           1770
  GGA CCC CCT CGA AGC TAT CTC CGC CAG TGG GTG GTC AGG ACC CCT CCA
  CCT GGG GGA GCT TCG ATA GAG GCG GTC ACC CAC CAG TCC TGG GGA GGT
  Gly Pro Pro Arg Ser Tyr Leu Arg Gln Trp Val Val Arg Thr Pro Pro>

1780           1790           1800
  CCT GTG GAC AGT GGA GCC CAG AGC AGC TAG
  GGA CAC CTG TCA CCT CGG GTC TCG TCG ATC
  Pro Val Asp Ser Gly Ala Gln Ser Ser ***>
```

Figure 4A Human Ig heavy chain locus (total length ≈1Mb, not drawn to scale):

Figure 4B Mouse IG heavy chain locus (total length ≈1Mb, not drawn to scale):

Figure 4C LTVEC2:

Figure 4D LTVEC1:

SEQUENCE LISTING

```
<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Mouse OCR10 gene primer

<400> SEQUENCE: 1
agctaccagc tgcagatgcg ggcag                                        25

<210> SEQ ID NO 2
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 2
```

```
ctccccagcc tgggtctgaa agatgacg                                          28
```

<210> SEQ ID NO 3
<211> LENGTH: 24
<212> TYPE: DNA
<213> ORGANISM: Artificial Sequence
<220> FEATURE:
<223> OTHER INFORMATION: Mouse OCR10 gene primer

<400> SEQUENCE: 3

```
gacctcactt gctacactga ctac                                              24
```

<210> SEQ ID NO 4
<211> LENGTH: 28
<212> TYPE: DNA
<213> ORGANISM: Artificial Sequence
<220> FEATURE:
<223> OTHER INFORMATION: Mouse OCR10 gene primer

<400> SEQUENCE: 4

```
acttgtgtag gctgcagaag gtctcttg                                          28
```

<210> SEQ ID NO 5
<211> LENGTH: 1799
<212> TYPE: DNA
<213> ORGANISM: Artificial Sequence
<220> FEATURE:
<223> OTHER INFORMATION: Mouse OCR10 cDNA

<400> SEQUENCE: 5

```
ccccgggctt cctgttctaa taagaatacc tcctaggtcc cccatgggct aacctcatct        60
ttggtactca acaggggtct tctttatgag cttcggacca gctcttttga tgtggcaggg       120
actgaccctg ggtggggaag ccactcagtg catgacccca gctggttcac cacatatacc       180
acatactttt cttgcaggtc tgggacacag catgccccgg ggcccagtgg ctgccttact       240
cctgctgatt ctccatggag cttggagctg cctggacctc acttgctaca ctgactacct       300
ctggaccatc acctgtgtcc tggagacacg gagccccaac cccagcatac tcagtctcac       360
ctggcaagat gaatatgagg aacttcagga ccaagagacc ttctgcagcc tacacaagtc       420
tggccacaac accacacata tatggtacac gtgccatatg cgcttgtctc aattcctgtc       480
cgatgaagtt tcattgtca acgtgacgga ccagtctggc aacaactccc aagagtgtgg       540
cagctttgtc ctggctgaga gcatcaagcc agctccccc ttgaacgtga ctgtggcctt       600
ctcaggacgc tatgatatct cctgggactc agcttatgac gaaccctcca actacgtgct       660
gagaggcaag ctacaatatg agctgcagta tcggaacctc agagaccct atgctgtgag       720
gccggtgacc aagctgatct cagtggactc aagaaacgtc tctcctccct gaagagttcc       780
acaaagattc tagctaccag ctgcagatgc gggcagcgcc tcagccaggc acttcattca       840
gggggacctg gagtgagtgg agtgaccccg tcatctttca gacccaggct ggggagcccg       900
aggcaggctg ggaccctcac atgctgctgc tcctggctgt cttgatcatt gtcctggttt       960
tcatgggtct gaagatccac ctgccttgga ggctatggaa aaagatatgg gcaccagtgc      1020
ccacccctga gagtttcttc cagccccgtg cagggagca gcgggaac ttcaagaaat        1080
gggttaatac ccccttcacg gcctccagca tagagttggt gccacagagt tccacaacaa      1140
catcagcctt acatctgtca ttgtatccag ccaaggagaa gaagttcccg gggctgccgg      1200
gtctggaaga gcaactggag tgtgatggaa tgtctgagcc tggtcactgg tgcataatcc      1260
ccttggcagc tggccaagcg gtctcagcct acagtgagga gagagaccgg ccatatggtc      1320
```

-continued

```
tggtgtccat tgacacagtg actgtgggag atgcagaggg cctgtgtgtc tggccctgta    1380
gctgtgagga tgatggctat ccagccatga acctggatgc tggcagagag tctggtccta    1440
attcagagga tctgctcttg gtcacagacc ctgcttttct gtcttgtggc tgtgtctcag    1500
gtagtggtct caggcttggg ggctccccag gcagcctact ggacaggttg aggctgtcat    1560
ttgcaaagga aggggactgg acagcagacc caacctggag aactgggtcc ccaggagggg    1620
gctctgagag tgaagcaggt tccccccctg gtctggacat ggacacattt gacagtggct    1680
ttgcaggttc agactgtggc agcccgtgg agactgatga aggaccccct cgaagctatc      1740
tccgccagtg ggtggtcagg acccctccac ctgtggacag tggagcccag agcagctag     1799
```

<210> SEQ ID NO 6
<211> LENGTH: 529
<212> TYPE: PRT
<213> ORGANISM: Artificial Sequence
<220> FEATURE:
<223> OTHER INFORMATION: Mouse OCR10 protein

<400> SEQUENCE: 6

```
Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
                35                  40                  45

Leu Thr Trp Gln Asp Glu Tyr Glu Glu Leu Gln Asp Gln Glu Thr Phe
 50                  55                  60

Cys Ser Leu His Lys Ser Gly His Asn Thr Thr His Ile Trp Tyr Thr
 65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
                100                 105                 110

Val Leu Ala Glu Ser Ile Lys Pro Ala Pro Pro Leu Asn Val Thr Val
                115                 120                 125

Ala Phe Ser Gly Arg Tyr Asp Ile Ser Trp Asp Ser Ala Tyr Asp Glu
                130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
                180                 185                 190

Asp Ser Ser Tyr Gln Leu Gln Met Arg Ala Ala Pro Gln Pro Gly Thr
                195                 200                 205

Ser Phe Arg Gly Thr Trp Ser Glu Trp Ser Asp Pro Val Ile Phe Gln
                210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
                260                 265                 270

Pro Glu Ser Phe Phe Gln Pro Leu Tyr Arg Glu His Ser Gly Asn Phe
```

-continued

```
        275                 280                 285
Lys Lys Trp Val Asn Thr Pro Phe Thr Ala Ser Ser Ile Glu Leu Val
        290                 295                 300
Pro Gln Ser Ser Thr Thr Thr Ser Ala Leu His Leu Ser Leu Tyr Pro
305                 310                 315                 320
Ala Lys Glu Lys Lys Phe Pro Gly Leu Pro Gly Leu Glu Glu Gln Leu
                325                 330                 335
Glu Cys Asp Gly Met Ser Glu Pro Gly His Trp Cys Ile Ile Pro Leu
                340                 345                 350
Ala Ala Gly Gln Ala Val Ser Ala Tyr Ser Glu Glu Arg Asp Arg Pro
                355                 360                 365
Tyr Gly Leu Val Ser Ile Asp Thr Val Thr Val Gly Asp Ala Glu Gly
        370                 375                 380
Leu Cys Val Trp Pro Cys Ser Cys Glu Asp Asp Gly Tyr Pro Ala Met
385                 390                 395                 400
Asn Leu Asp Ala Gly Arg Glu Ser Gly Pro Asn Ser Glu Asp Leu Leu
                405                 410                 415
Leu Val Thr Asp Pro Ala Phe Leu Ser Cys Gly Cys Val Ser Gly Ser
                420                 425                 430
Gly Leu Arg Leu Gly Gly Ser Pro Gly Ser Leu Leu Asp Arg Leu Arg
            435                 440                 445
Leu Ser Phe Ala Lys Glu Gly Asp Trp Thr Ala Asp Pro Thr Trp Arg
        450                 455                 460
Thr Gly Ser Pro Gly Gly Gly Ser Glu Ser Glu Ala Gly Ser Pro Pro
465                 470                 475                 480
Gly Leu Asp Met Asp Thr Phe Asp Ser Gly Phe Ala Gly Ser Asp Cys
                485                 490                 495
Gly Ser Pro Val Glu Thr Asp Glu Gly Pro Pro Arg Ser Tyr Leu Arg
                500                 505                 510
Gln Trp Val Val Arg Thr Pro Pro Pro Val Asp Ser Gly Ala Gln Ser
            515                 520                 525
Ser
```

METHODS OF MAKING A NUCLEIC ACID ENCODING A HUMAN VARIABLE REGION

CROSS-REFERENCE TO RELATED APPLICATIONS

This application is a continuation of U.S. Ser. No. 13/154,976, filed 7 Jun. 2011, which is a continuation of U.S. Ser. No. 11/595,427, filed 9 Nov. 2006, which is a continuation of U.S. Ser. No. 10/624,044 filed 21 Jul. 2003, which is a divisional of U.S. Ser. No. 09/784,859, filed 16 Feb. 2001, now U.S. Pat. No. 6,596,541, which is a continuation-in-part of U.S. Ser. No. 09/732,234, filed 7 Dec. 2000, now U.S. Pat. No. 6,585,251, which claims the benefit of U.S. Ser. No. 60/244,665, filed 31 Oct. 2000, (each application hereby incorporated by reference); this application is also a continuation of U.S. Ser. No. 11/595,427, filed 9 Nov. 2006, which is a continuation of U.S. Ser. No. 10/624,044 filed 21 Jul. 2003, which is a divisional of U.S. Ser. No. 09/784,859, filed 16 Feb. 2001, now U.S. Pat. No. 6,596,541, which is a continuation-in-part of U.S. Ser. No. 09/732,234, filed 7 Dec. 2000, now U.S. Pat. No. 6,585,251, which claims the benefit of U.S. Ser. No. 60/244,665, filed 31 Oct. 2000, (each application hereby incorporated by reference).

FIELD OF THE INVENTION

The field of this invention is a method for engineering and utilizing large DNA vectors to target, via homologous recombination, and modify, in any desirable fashion, endogenous genes and chromosomal loci in eukaryotic cells. The field also encompasses the use of these cells to generate organisms bearing the genetic modification, the organisms, themselves, and methods of use thereof.

BACKGROUND

The use of LTVECs provides substantial advantages over current methods. For example, since these are derived from DNA fragments larger than those currently used to generate targeting vectors, LTVECs can be more rapidly and conveniently generated from available libraries of large genomic DNA fragments (such as BAC and PAC libraries) than targeting vectors made using current technologies. In addition, larger modifications as well as modifications spanning larger genomic regions can be more conveniently generated than using current technologies. Furthermore, the present invention takes advantage of long regions of homology to increase the targeting frequency of "hard to target" loci, and also diminishes the benefit, if any, of using isogenic DNA in these targeting vectors.

The present invention thus provides for a rapid, convenient, and streamlined method for systematically modifying virtually all the endogenous genes and chromosomal loci of a given organism.

Gene targeting by means of homologous recombination between homologous exogenous DNA and endogenous chromosomal sequences has proven to be an extremely valuable way to create deletions, insertions, design mutations, correct gene mutations, introduce transgenes, or make other genetic modifications in mice. Current methods involve using standard targeting vectors, with regions of homology to endogenous DNA typically totaling less than 10-20 kb, to introduce the desired genetic modification into mouse embryonic stem (ES) cells, followed by the injection of the altered ES cells into mouse embryos to transmit these engineered genetic modifications into the mouse germline (Smithies et al., Nature, 317:230-234, 1985; Thomas et al., Cell, 51:503-512, 1987; Koller et al., Proc Natl Acad Sci USA, 86:8927-8931, 1989; Kuhn et al., Science, 254:707-710, 1991; Thomas et al., Nature, 346:847-850, 1990; Schwartzberg et al., Science, 246:799-803, 1989; Doetschman et al., Nature, 330:576-578, 1987; Thomson et al., Cell, 5:313-321, 1989; DeChiara et al., Nature, 345:78-80, 1990; U.S. Pat. No. 5,789,215, issued Aug. 4, 1998 in the name of GenPharm International) In these current methods, detecting the rare ES cells in which the standard targeting vectors have correctly targeted and modified the desired endogenous gene(s) or chromosomal locus (loci) requires sequence information outside of the homologous targeting sequences contained within the targeting vector. Assays for successful targeting involve standard Southern blotting or long PCR (see for example Cheng, et al., Nature, 369:684-5, 1994; U.S. Pat. No. 5,436,149) from sequences outside the targeting vector and spanning an entire homology arm (see Definitions); thus, because of size considerations that limit these methods, the size of the homology arms are restricted to less than 10-20 kb in total (Joyner, The Practical Approach Series, 293, 1999).

The ability to utilize targeting vectors with homology arms larger than those used in current methods would be extremely valuable. For example, such targeting vectors could be more rapidly and conveniently generated from available libraries containing large genomic inserts (e.g. BAC or PAC libraries) than targeting vectors made using current technologies, in which such genomic inserts have to be extensively characterized and trimmed prior to use. In addition, larger modifications as well as modifications spanning larger genomic regions could be more conveniently generated and in fewer steps than using current technologies. Furthermore, the use of long regions of homology could increase the targeting frequency of "hard to target" loci in eukaryotic cells, since the targeting of homologous recombination in eukaryotic cells appears to be related to the total homology contained within the targeting vector (Deng and Capecchi, Mol Cell Biol, 12:3365-71, 1992). In addition, the increased targeting frequency obtained using long homology arms could diminish any potential benefit that can be derived from using isogenic DNA in these targeting vectors.

The problem of engineering precise modifications into very large genomic fragments, such as those cloned in BAC libraries, has largely been solved through the use of homologous recombination in bacteria (Zhang, et al., Nat Genet, 20:123-8, 1998; Yang, et al., Nat Biotechnol, 15:859-65, 1997; Angrand, et al., Nucleic Acids Res, 27:e16, 1999; Muyrers, et al., Nucleic Acids Res, 27:1555-7, 1999; Narayanan, et al., Gene Ther, 6:442-7, 1999), allowing for the construction of vectors containing large regions of homology to eukaryotic endogenous genes or chromosomal loci. However, once made, these vectors have not been generally useful for modifying endogenous genes or chromosomal loci via homologous recombination because of the difficulty in detecting rare correct targeting events when homology arms are larger than 10-20 kb (Joyner supra). Consequently, vectors generated using bacterial homologous recombination from BAC genomic fragments must still be extensively trimmed prior to use as targeting vectors (Hill et al., Genomics, 64:111-3, 2000). Therefore, there is still a need for a rapid and convenient methodology that makes possible the use of targeting vectors containing large regions of homology so as to modify endogenous genes or chromosomal loci in eukaryotic cells.

In accordance with the present invention, Applicants provide novel methods that enables the use of targeting vectors containing large regions of homology so as to modify endogenous genes or chromosomal loci in eukaryotic cells via homologous recombination. Such methods overcome the above-described limitations of current technologies. In addition, the skilled artisan will readily recognize that the methods of the invention are easily adapted for use with any genomic DNA of any eukaryotic organism including, but not limited to, animals such as mouse, rat, other rodent, or human, as well as plants such as soy, corn and wheat.

SUMMARY OF THE INVENTION

In accordance with the present invention, Applicants have developed a novel, rapid, streamlined, and efficient method for creating and screening eukaryotic cells which contain modified endogenous genes or chromosomal loci. This novel methods combine, for the first time: 1. Bacterial homologous recombination to precisely engineer a desired genetic modification within a large cloned genomic fragment, thereby creating a large targeting vector for use in eukaryotic cells (LTVECs); 2. Direct introduction of these LTVECs into eukaryotic cells to modify the endogenous chromosomal locus of interest in these cells; and 3. An analysis to determine the rare eukaryotic cells in which the targeted allele has been modified as desired, involving an assay for modification of allele (MOA) of the parental allele that does not require sequence information outside of the targeting sequence, such as, for example, quantitative PCR.

A preferred embodiment of the invention is a method for genetically modifying an endogenous gene or chromosomal locus in eukaryotic cells, comprising: a) obtaining a large cloned genomic fragment containing a DNA sequence of interest; b) using bacterial homologous recombination to genetically modify the large cloned genomic fragment of (a) to create a large targeting vector for use in the eukaryotic cells (LTVEC); c) introducing the LTVEC of (b) into the eukaryotic cells to modify the endogenous gene or chromosomal locus in the cells; and d) using a quantitative assay to detect modification of allele (MOA) in the eukaryotic cells of (c) to identify those eukaryotic cells in which the endogenous gene or chromosomal locus has been genetically modified. Another embodiment of the invention is a method wherein the genetic modification to the endogenous gene or chromosomal locus comprises deletion of a coding sequence, gene segment, or regulatory element; alteration of a coding sequence, gene segment, or regulatory element; insertion of a new coding sequence, gene segment, or regulatory element; creation of a conditional allele; or replacement of a coding sequence or gene segment from one species with an homologous or orthologous coding sequence from a different species. An alternative embodiment of the invention is a method wherein the alteration of a coding sequence, gene segment, or regulatory element comprises a substitution, addition, or fusion, wherein the fusion comprises an epitope tag or bifunctional protein. Yet another embodiment of the invention is a method wherein the quantitative assay comprises quantitative PCR, comparative genomic hybridization, isothermic DNA amplification, or quantitative hybridization to an immobilized probe, wherein the quantitative PCR comprises TAQMAN® technology or quantitative PCR using molecular beacons. Another preferred embodiment of the invention is a method wherein the eukaryotic cell is a mammalian embryonic stem cell and in particular wherein the embryonic stem cell is a mouse, rat, or other rodent embryonic stem cell. Another preferred embodiment of the invention is a method wherein the endogenous gene or chromosomal locus is a mammalian gene or chromosomal locus, preferably a human gene or chromosomal locus or a mouse, rat, or other rodent gene or chromosomal locus. An additional preferred embodiment is one in which the LTVEC is capable of accommodating large DNA fragments greater than 20 kb, and in particular large DNA fragments greater than 100 kb. Another preferred embodiment is a genetically modified endogenous gene or chromosomal locus that is produced by the method of the invention. Yet another preferred embodiment is a genetically modified eukaryotic cell that is produced by the method of the invention. A preferred embodiment of the invention is a non-human organism containing the genetically modified endogenous gene or chromosomal locus produced by the method of the invention. Also preferred in a non-human organism produced from the genetically modified eukaryotic cells or embryonic stem cells produced by the method of the invention.

A preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector (LTVEC) for use in embryonic stem cells; c) introducing the LTVEC of (b) into the embryonic stem cells to modify the endogenous gene or chromosomal locus in the cells; d) using a quantitative assay to detect modification of allele (MOA) in the embryonic stem cells of (c) to identify those embryonic stem cells in which the endogenous gene or chromosomal locus has been genetically modified; e) introducing the embryonic stem cell of (d) into a blastocyst; and f) introducing the blastocyst of (e) into a surrogate mother for gestation.

An additional preferred embodiment of the invention is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) removing the nucleus from the eukaryotic cell of (d); f) introducing the nucleus of (e) into an oocyte; and g) introducing the oocyte of (f) into a surrogate mother for gestation.

Yet another preferred embodiment is a non-human organism containing a genetically modified endogenous gene or chromosomal locus, produced by a method comprising the steps of: a) obtaining a large cloned genomic fragment containing a DNA sequence of interest; b) using bacterial homologous recombination to genetically modify the large cloned genomic fragment of (a) to create a large targeting vector for use in eukaryotic cells (LTVEC); c) introducing the LTVEC of (b) into the eukaryotic cells to genetically modify the endogenous gene or chromosomal locus in the cells; d) using a quantitative assay to detect modification of allele (MOA) in the eukaryotic cells of (c) to identify those eukaryotic cells in which the endogenous gene or chromosomal locus has been genetically modified; e) fusing the eukaryotic cell of (d) with another eukaryotic cell; f) introducing the fused eukaryotic cell of (e) into a surrogate mother for gestation.

A preferred embodiment of the invention is a method for genetically modifying an endogenous gene or chromosomal locus of interest in mouse embryonic stem cells, comprising: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR. Also preferred is a genetically modified mouse embryonic stem cell produced by this method; a mouse containing a genetically modified endogenous gene or chromosomal locus produced by this method; and a mouse produced from the genetically modified mouse embryonic stem cell.

Another preferred embodiment is a mouse containing a genetically modified endogenous gene or chromosomal locus of interest, produced by a method comprising the steps of: a) obtaining a large cloned genomic fragment greater than 20 kb which contains a DNA sequence of interest, wherein the large cloned DNA fragment is homologous to the endogenous gene or chromosomal locus; b) using bacterial homologous recombination to genetically modify the large cloned genomic fragment of (a) to create a large targeting vector for use in the mouse embryonic stem cells, wherein the genetic modification is deletion of a coding sequence, gene segment, or regulatory element; c) introducing the large targeting vector of (b) into the mouse embryonic stem cells to modify the endogenous gene or chromosomal locus in the cells; and d) using a quantitative assay to detect modification of allele (MOA) in the mouse embryonic stem cells of (c) to identify those mouse embryonic stem cells in which the endogenous gene or chromosomal locus has been genetically modified, wherein the quantitative assay is quantitative PCR; e) introducing the mouse embryonic stem cell of (d) into a blastocyst; and f) introducing the blastocyst of (e) into a surrogate mother for gestation.

One embodiment of the invention is a method of replacing, in whole or in part, in a non-human eukaryotic cell, an endogenous immunoglobulin variable region gene locus with an homologous or orthologous human gene locus comprising: a) obtaining a large cloned genomic fragment containing, in whole or in part, the homologous or orthologous human gene locus; b) using bacterial homologous recombination to genetically modify the cloned genomic fragment of (a) to create a large targeting vector for use in the eukaryotic cells (LTVEC); c) introducing the LTVEC of (b) into the eukaryotic cells to replace, in whole or in part, the endogenous immunoglobulin variable gene locus; and d) using a quantitative assay to detect modification of allele (MOA) in the eukaryotic cells of (c) to identify those eukaryotic cells in which the endogenous immunoglobulin variable region gene locus has been replaced, in whole or in part, with the homologous or orthologous human gene locus.

Another embodiment is a method of replacing, in whole or in part, in a non-human eukaryotic cell, an endogenous immunoglobulin variable region gene locus with an homologous or orthologous human gene locus further comprising the steps: e) obtaining a large cloned genomic fragment containing a part of the homologous or orthologous human gene locus that differs from the fragment of (a); f) using bacterial homologous recombination to genetically modify the cloned genomic fragment of (e) to create a second LTVEC; g) introducing the second LTVEC of (f) into the eukaryotic cells identified in step (d) to replace, in whole or in part, the endogenous immunoglobulin variable gene locus; and h) using a quantitative assay to detect modification of allele (MOA) in the eukaryotic cells of (g) to identify those eukaryotic cells in which the endogenous immunoglobulin variable region gene locus has been replaced, in whole or in part, with the homologous or orthologous human gene locus.

Another embodiment of the above method is a method wherein steps (e) through (h) are repeated until the endogenous immunoglobulin variable region gene locus is replaced in whole with an homologous or orthologous human gene locus.

Another embodiment of the method is one in which the immunoglobulin variable gene locus is a locus selected from the group consisting of a) a variable gene locus of the kappa light chain; b) a variable gene locus of the lambda light chain; and c) a variable gene locus of the heavy chain.

A preferred embodiment is a method wherein the quantitative assay comprises quantitative PCR, FISH, comparative genomic hybridization, isothermic DNA amplification, or quantitative hybridization to an immobilized probe, and in particular wherein the quantitative PCR comprises TAQMAN®. technology or quantitative PCR using molecular beacons.

Yet another preferred embodiment is a method of replacing, in whole or in part, in a mouse embryonic stem cell, an endogenous immunoglobulin variable region gene locus with its homologous or orthologous human gene locus comprising: a) obtaining a large cloned genomic fragment containing, in whole or in part, the homologous or orthologous human gene locus; b) using bacterial homologous recombination to genetically modify the large cloned genomic fragment of (a) to create a large targeting vector for use in the embryonic stem cells; c) introducing the large targeting vector of (b) into mouse embryonic stem cells to replace, in whole or in part, the endogenous immunoglobulin variable gene locus in the cells; and d) using a quantitative PCR assay to detect modification of allele (MOA) in the mouse embryonic stem cells of (d) to identify those mouse embryonic stem cells in which the endogenous variable gene locus has been replaced, in whole or in part, with the homologous or orthologous human gene locus.

In another embodiment, the method further comprises: e) obtaining a large cloned genomic fragment containing a part of the homologous or orthologous human gene locus that differs from the fragment of (a); f) using bacterial homologous recombination to genetically modify the cloned genomic fragment of (e) to create a large targeting vector for use in the embryonic stem cells; g) introducing the large targeting vector of (f) into the mouse embryonic stem cells identified in step (d) to replace, in whole or in part, the endogenous immunoglobulin variable gene locus; and h) using a quantitative assay to detect modification of allele (MOA) in the mouse embryonic stem cells of (g) to identify those mouse embryonic stem cells in which the endogenous immunoglobulin variable region gene locus has been replaced, in whole or in part, with the homologous or orthologous human gene locus.

Another preferred embodiment is a genetically modified immunoglobulin variable region gene locus produced by the methods described above; a genetically modified eukaryotic cell comprising a genetically modified immunoglobulin variable region gene locus produced by the methods described above; a non-human organism comprising a genetically modified immunoglobulin variable region gene locus produced by the methods described above; and a mouse embryonic stem cell containing a genetically modified immunoglobulin variable region gene locus produced by the methods described above.

Also preferred is an embryonic stem cell wherein the mouse heavy chain variable region locus is replaced, in whole or in part, with a human heavy chain variable gene locus; an embryonic stem cell of claim wherein the mouse kappa light chain variable region locus is replaced, in whole or in part, with a human kappa light chain variable region locus; an embryonic stem cell wherein the mouse lambda light chain variable region locus is replaced, in whole or in part, with a human lambda light chain variable region locus; and an embryonic stem cell wherein the heavy and light chain variable region gene loci are replaced, in whole, with their human homologs or orthologs.

Yet another preferred embodiment is an antibody comprising a human variable region encoded by the genetically modified variable gene locus of described above; an antibody further comprising a non-human constant region; and an antibody further comprising a human constant region.

Also preferred is a transgenic mouse having a genome comprising entirely human heavy and light chain variable region loci operably linked to entirely endogenous mouse constant region loci such that the mouse produces a serum containing an antibody comprising a human variable region and a mouse constant region in response to antigenic stimulation; a transgenic mouse having a genome comprising human heavy and/or light chain variable region loci operably linked to endogenous mouse constant region loci such that the mouse produces a serum containing an antibody comprising a human variable region and a mouse constant region in response to antigenic stimulation; a transgenic mouse containing an endogenous variable region locus that has been replaced with an homologous or orthologous human variable locus, such mouse being produced by a method comprising: a) obtaining one or more large cloned genomic fragments containing the entire homologous or orthologous human variable region locus; b) using bacterial homologous recombination to genetically modify the cloned genomic fragment(s) of (a) to create large targeting vector(s) for use in mouse embryonic stem cells; c) introducing the large targeting vector(s) of (b) into mouse embryonic stem cells to replace the entire endogenous variable region locus in the cells; and d) using a quantitative PCR assay to detect modification of allele (MOA) in the mouse embryonic stem cells of (c) to identify those mouse embryonic stem cells in which the entire endogenous variable region locus has been replaced with the homologous or orthologous human variable region locus; e) introducing the mouse embryonic stem cell of (d) into a blastocyst; and f) introducing the blastocyst of (e) into a surrogate mother for gestation.

Still yet another preferred embodiment of the invention is a method of making a human antibody comprising: a) exposing the mouse described above to antigenic stimulation, such that the mouse produces an antibody against the antigen; b) isolating the DNA encoding the variable regions of the heavy and light chains of the antibody; c) operably linking the DNA encoding the variable regions of (b) to DNA encoding the human heavy and light chain constant regions in a cell capable of expressing active antibodies; d) growing the cell under such conditions as to express the human antibody; and e) recovering the antibody. In another preferred embodiment, the cell described above is a CHO cell. Also preferred is a method of wherein the DNA of step (b) described above is isolated from a hybridoma created from the spleen of the mouse exposed to antigenic stimulation in step (a) described above.

BRIEF DESCRIPTION OF THE FIGURES

FIG. 3A-3D: Sequence of the mouse OCR10 cDNA (upper strand, SEQ ID NO: 5; amino acid, SEQ ID NO: 6), homology box 1 (hb1), homology box 2 (hb2), and TAQMAN® probes and primers used in a quantitative PCR assay to detect modification of allele (MOA) in ES cells targeted using the mOCR10 LTVEC. hb1: base pairs 1 to 211; hb2: base pairs 1586 to 1801; TAQMAN® probe and corresponding PCR primer set derived from mOCR10 exon 3: TAQMAN® probe: nucleotides 413 to 439—upper strand; Primer ex3-5': nucleotides 390 to 410—upper strand; Primer ex3-3': nucleotides 445 to 461—lower strand; TAQMAN® probe and corresponding PCR primer set derived from mOCR10 exon 4: TAQMAN® probe: nucleotides 608 to 639—upper strand; Primer ex4-5': nucleotides 586 to 605—upper strand; Primer ex4-3': nucleotides 642 to 662—lower strand.

DETAILED DESCRIPTION

Figure 1:
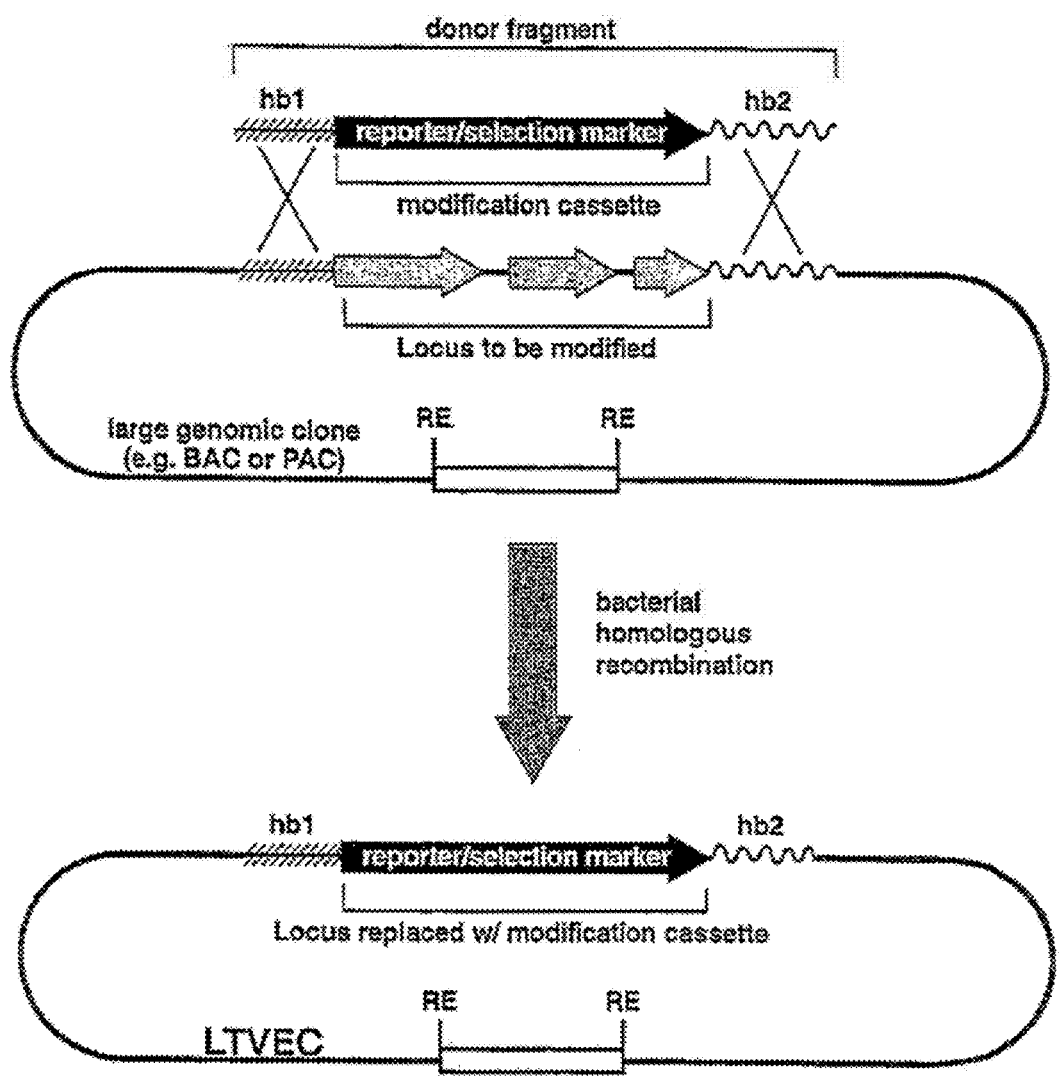
FIG. 1: Schematic diagram of the generation of a typical LTVEC using bacterial homologous recombination. (hb1=homology box 1; hb2=homology box 2; RE=restriction enzyme site).

A "targeting vector" is a DNA construct that contains sequences "homologous" to endogenous chromosomal nucleic acid sequences flanking a desired genetic modification(s). The flanking homology sequences, referred to as "homology arms", direct the targeting vector to a specific chromosomal location within the genome by virtue of the homology that exists between the homology arms and the corresponding endogenous sequence and introduce the desired genetic modification by a process referred to as "homologous recombination".

"Homologous" means two or more nucleic acid sequences that are either identical or similar enough that they are able to hybridize to each other or undergo intermolecular exchange.

"Gene targeting" is the modification of an endogenous chromosomal locus by the insertion into, deletion of, or replacement of the endogenous sequence via homologous recombination using a targeting vector.

A "gene knockout" is a genetic modification resulting from the disruption of the genetic information encoded in a chromosomal locus. A "gene knockin" is a genetic modification resulting from the replacement of the genetic information encoded in a chromosomal locus with a different DNA sequence. A "knockout organism" is an organism in which a significant proportion of the organism's cells harbor a gene knockout. A "knockin organism" is an organism in which a significant proportion of the organism's cells harbor a gene knockin.

A "marker" or a "selectable marker" is a selection marker that allows for the isolation of rare transfected cells expressing the marker from the majority of treated cells in the population. Such marker's gene's include, but are not limited to, neomycin phosphotransferase and hygromycin B phosphotransferase, or fluorescing proteins such as GFP.

An "ES cell" is an embryonic stem cell. This cell is usually derived from the inner cell mass of a blastocyst-stage embryo. An "ES cell clone" is a subpopulation of cells derived from a single cell of the ES cell population following introduction of DNA and subsequent selection.

A "flanking DNA" is a segment of DNA that is collinear with and adjacent to a particular point of reference.

"LTVECs" are large targeting vectors for eukaryotic cells that are derived from fragments of cloned genomic DNA larger than those typically used by other approaches intended to perform homologous targeting in eukaryotic cells.

"Modification of allele" (MOA) refers to the modification of the exact DNA sequence of one allele of a gene(s) or chromosomal locus (loci) in a genome. This modification of allele (MOA) includes, but is not limited to, deletions, substitutions, or insertions of as little as a single nucleotide or deletions of many kilobases spanning a gene(s) or chromosomal locus (loci) of interest, as well as any and all possible modifications between these two extremes.

"Orthologous" sequence refers to a sequence from one species that is the functional equivalent of that sequence in another species.

General Description

Applicants have developed a novel, rapid, streamlined, and efficient method for creating and screening eukaryotic cells which contain modified endogenous genes or chromosomal loci. In these cells, the modification may be gene(s) knockouts, knockins, point mutations, or large genomic insertions or deletions or other modifications. These cells may be embryonic stem cells which are useful for creating knockout or knockin organisms and in particular, knockout or knockin mice, for the purpose of determining the function of the gene(s) that have been altered, deleted and/or inserted.

The novel methods described herein combine, for the first time: 1. Bacterial homologous recombination to precisely engineer a desired genetic modification within a large cloned genomic DNA fragment, thereby creating a large targeting vector for use in eukaryotic cells (LTVECs); 2. Direct introduction of these LTVECs into eukaryotic cells to modify the corresponding endogenous gene(s) or chromosomal locus (loci) of interest in these cells; and 3. An analysis to determine the rare eukaryotic cells in which the targeted allele has been modified as desired, involving a quantitative assay for modification of allele (MOA) of the parental allele.

It should be emphasized that previous methods to detect successful homologous recombination in eukaryotic cells cannot be utilized in conjunction with the LTVECs of Applicants' invention because of the long homology arms present in the LTVECs. Utilizing a LTVEC to deliberately modify endogenous genes or chromosomal loci in eukaryotic cells via homologous recombination is made possible by the novel application of an assay to determine the rare eukaryotic cells in which the targeted allele has been modified as desired, such assay involving a quantitative assay for modification of allele (MOA) of a parental allele, by employing, for example, quantitative PCR or other suitable quantitative assays for MOA.

The ability to utilize targeting vectors with homology arms larger than those used in current methods is extremely valuable for the following reasons: 1. Targeting vectors are more rapidly and conveniently generated from available libraries containing large genomic inserts (e.g. BAC or PAC libraries) than targeting vectors made using previous technologies, in which the genomic inserts have to be extensively characterized and "trimmed" prior to use (explained in detail below). In addition, minimal sequence information needs to be known about the locus of interest, i.e. it is only necessary to know the approximately 80-100 nucleotides that are required to generate the homology boxes (described in detail below) and to generate probes that can be used in quantitative assays for MOA (described in detail below). 2. Larger modifications as well as modifications spanning larger genomic regions are more conveniently generated and in fewer steps than using previous technologies. For example, the method of the invention makes possible the precise modification of large loci that cannot be accommodated by traditional plasmid-based targeting vectors because of their size limitations. It also makes possible the modification of any given locus at multiple points (e.g. the introduction of specific mutations at different exons of a multi-exon gene) in one step, alleviating the need to engineer multiple targeting vectors and to perform multiple rounds of targeting and screening for homologous recombination in ES cells. 3. The use of long regions of homology (long homology arms) increase the targeting frequency of "hard to target" loci in eukaryotic cells, consistent with previous findings that targeting of homologous recombination in eukaryotic cells appears to be related to the total homology contained within the targeting vector. 4. The increased targeting frequency obtained using long homology arms apparently diminishes the benefit, if any, from using isogenic DNA in these targeting vectors. 5. The application of quantitative MOA assays for screening eukaryotic cells for homologous recombination not only empowers the use of LTVECs as targeting vectors (advantages outlined above) but also reduces the time for identifying correctly modified eukaryotic cells from the typical several days to a few hours. In addition, the application of quantitative MOA does not require the use of probes located outside the endogenous gene(s) or chromosomal locus (loci) that is being modified, thus obviating the need to know the sequence flanking the modified gene(s) or locus (loci). This is a significant improvement in the way the screening has been performed in the past and makes it a much less labor-intensive and much more cost-effective approach to screening for homologous recombination events in eukaryotic cells.

Methods

Many of the techniques used to construct DNA vectors described herein are standard molecular biology techniques well known to the skilled artisan (see e.g., Sambrook, J., E. F. Fritsch And T. Maniatis. Molecular Cloning: A Laboratory Manual, Second Edition, Vols 1, 2, and 3, 1989; Current Protocols in Molecular Biology, Eds. Ausubel et al., Greene Publ. Assoc., Wiley Interscience, NY). All DNA sequencing is done by standard techniques using an ABI 373A DNA sequencer and Taq Dideoxy Terminator Cycle Sequencing Kit (Applied Biosystems, Inc., Foster City, Calif.).

Step 1. Obtain a Large Genomic DNA Clone Containing the Gene(s) or Chromosomal Locus (Loci) of Interest.

A gene(s) or locus (loci) of interest can be selected based on specific criteria, such as detailed structural or functional data, or it can be selected in the absence of such detailed information as potential genes or gene fragments become predicted through the efforts of the various genome sequencing projects. Importantly, it should be noted that it is not necessary to know the complete sequence and gene structure of a gene(s) of interest to apply the method of the subject invention to produce LTVECs. In fact, the only sequence information that is required is approximately 80-100 nucleotides so as to obtain the genomic clone of interest as well as to generate the homology boxes used in making the LTVEC (described in detail below) and to make probes for use in quantitative MOA assays.

Once a gene(s) or locus (loci) of interest has been selected, a large genomic clone(s) containing this gene(s) or locus (loci) is obtained. This clone(s) can be obtained in any one of several ways including, but not limited to, screening suitable DNA libraries (e.g. BAC, PAC, YAC, or cosmid) by standard hybridization or PCR techniques, or by any other methods familiar to the skilled artisan.

Step 2. Append Homology Boxes 1 and 2 to a Modification Cassette and Generation of LTVEC.

Homology boxes mark the sites of bacterial homologous recombination that are used to generate LTVECs from large cloned genomic fragments (FIG. 1). Homology boxes are short segments of DNA, generally double-stranded and at least 40 nucleotides in length, that are homologous to regions within the large cloned genomic fragment flanking the "region to be modified". The homology boxes are appended to the modification cassette, so that following homologous recombination in bacteria, the modification cassette replaces the region to be modified (FIG. 1). The technique of creating a targeting vector using bacterial homologous recombination can be performed in a variety of systems (Yang et al. supra; Muyrers et al. supra; Angrand et al. supra; Narayanan et al. supra; Yu, et al., Proc Natl Acad Sci USA, 97:5978-83, 2000). One example of a favored technology currently in use is ET cloning and variations of this technology (Yu et al. supra). ET refers to the recE (Hall and Kolodner, Proc Natl Acad Sci USA, 91:3205-9, 1994) and recT proteins (Kusano et al., Gene, 138:17-25, 1994) that carry out the homologous recombination reaction. RecE is an exonuclease that trims one strand of linear double-stranded DNA (essentially the donor DNA fragment described infra) 5' to 3', thus leaving behind a linear double-stranded fragment with a 3' single-stranded overhang. This single-stranded overhang is coated by recT protein, which has single-stranded DNA (ssDNA) binding activity (Kovall and Matthews, Science, 277:1824-7, 1997). ET cloning is performed using $E.\ coli$ that transiently express the $E.\ coli$ gene products of recE and recT (Hall and Kolodner, Proc Natl Acad Sci USA, 91:3205-9, 1994; Clark et al., Cold Spring Herb Symp Quant Biol, 49:453-62, 1984; Noirot and Kolodner, J Biol Chem, 273:12274-80, 1998; Thresher et al., J Mol Biol, 254:364-71, 1995; Kolodner et al., Mol Microbiol, 11:23-30, 1994; Hall et al., J Bacteriol, 175:277-87, 1993) and the bacteriophage lambda (λ) protein λgam (Murphy, J Bacteriol, 173:5808-21, 1991; Poteete et al., J Bacteriol, 170:2012-21, 1988). The λgam protein is required for protecting the donor DNA fragment from degradation by the recBC exonuclease system (Myers and Stahl, Annu Rev Genet, 28:49-70, 1994) and it is required for efficient ET-cloning in recBC$^+$ hosts such as the frequently used $E.\ coli$ strain DH10b.

The region to be modified and replaced using bacterial homologous recombination can range from zero nucleotides in length (creating an insertion into the original locus) to many tens of kilobases (creating a deletion and/or a replacement of the original locus). Depending on the modification cassette, the modification can result in the following: (a) deletion of coding sequences, gene segments, or regulatory elements; (b) alteration(s) of coding sequence, gene segments, or regulatory elements including substitutions, additions, and fusions (e.g. epitope tags or creation of bifunctional proteins such as those with GFP); (c) insertion of new coding regions, gene segments, or regulatory elements, such as those for selectable marker genes or reporter genes or putting new genes under endogenous transcriptional control; (d) creation of conditional alleles, e.g. by introduction of loxP sites flanking the region to be excised by Cre recombinase (Abremski and Hoess, J Biol Chem, 259:1509-14, 1984), or FRT sites flanking the region to be excised by Flp recombinase (Andrews et al., Cell, 40:795-803, 1985; Meyer-Leon et al., Cold Spring Harb Symp Quant Biol, 49:797-804, 1984; Cox, Proc Natl Acad Sci USA, 80:4223-7, 1983); or (e) replacement of coding sequences or gene segments from one species with orthologous coding sequences from a different species, e.g. replacing a murine genetic locus with the orthologous human genetic locus to engineer a mouse where that particular locus has been 'humanized'.

Any or all of these modifications can be incorporated into a LTVEC. A specific example in which an endogenous coding sequence is entirely deleted and simultaneously replaced with both a reporter gene as well as a selectable marker is provided below in Example 1, as are the advantages of the method of the invention as compared to previous technologies.

Step 3 (Optional). Verify that Each LTVEC has been Engineered Correctly.

Verify that each LTVEC has been engineered correctly by: a. Diagnostic PCR to verify the novel junctions created by the introduction of the donor fragment into the gene(s) or chromosomal locus (loci) of interest. The PCR fragments thus obtained can be sequenced to further verify the novel junctions created by the introduction of the donor fragment into the gene(s) or chromosomal locus (loci) of interest. b. Diagnostic restriction enzyme digestion to make sure that only the desired modifications have been introduced into the LTVEC during the bacterial homologous recombination process. c. Direct sequencing of the LTVEC, particularly the regions spanning the site of the modification to verify the novel junctions created by the introduction of the donor fragment into the gene(s) or chromosomal locus (loci) of interest.

Step 4. Purification, Preparation, and Linearization of LTVEC DNA for Introduction into Eukaryotic Cells.

a. Preparation of LTVEC DNA:

Prepare miniprep DNA (Sambrook et al. supra; Tillett and Neilan, Biotechniques, 24:568-70, 572, 1998; of the selected LTVEC and re-transform the miniprep LTVEC DNA into *E. coli* using electroporation (Sambrook et al. supra). This step is necessary to get rid of the plasmid encoding the recombinogenic proteins that are utilized for the bacterial homologous recombination step. It is useful to get rid of this plasmid (a) because it is a high copy number plasmid and may reduce the yields obtained in the large scale LTVEC preps; (b) to eliminate the possibility of inducing expression of the recombinogenic proteins; and (c) because it may obscure physical mapping of the LTVEC. Before introducing the LTVEC into eukaryotic cells, larger amounts of LTVEC DNA are prepared by standard methodology; Sambrook et al. supra; Tillett and Neilan, Biotechniques, 24:568-70, 572, 1998). However, this step can be bypassed if a bacterial homologous recombination method that utilizes a recombinogenic prophage is used, i.e. where the genes encoding the recombinogenic proteins are integrated into the bacterial chromosome (Yu, et al. supra), is used.

b. Linearizing the LTVEC DNA:

To prepare the LTVEC for introduction into eukaryotic cells, the LTVEC is preferably linearized in a manner that leaves the modified endogenous gene(s) or chromosomal locus (loci) DNA flanked with long homology arms. This can be accomplished by linearizing the LTVEC, preferably in the vector backbone, with any suitable restriction enzyme that digests only rarely. Examples of suitable restriction enzymes include NotI, PacI, SfiI, SrfI, SwaI, FseI, etc. The choice of restriction enzyme may be determined experimentally (i.e. by testing several different candidate rare cutters) or, if the sequence of the LTVEC is known, by analyzing the sequence and choosing a suitable restriction enzyme based on the analysis. In situations where the LTVEC has a vector backbone containing rare sites such as Cos N sites, then it can be cleaved with enzymes recognizing such sites, for example λ terminase (Shizuya et al., Proc Natl Acad Sci USA, 89:8794-7, 1992; Becker and Gold, Proc Natl Acad Sci USA, 75:4199-203, 1978; Rackwitz et al., Gene, 40:259-66, 1985).

Step 5. Introduction of LTVEC into Eukaryotic Cells and Selection of Cells where Successful Introduction of the LTVEC has Taken Place.

LTVEC DNA can be introduced into eukaryotic cells using standard methodology, such as transfection mediated by calcium phosphate, lipids, or electroporation (Sambrook et al. supra). The cells where the LTVEC has been introduced successfully can be selected by exposure to selection agents, depending on the selectable marker gene that has been engineered into the LTVEC. For example, if the selectable marker is the neomycin phosphotransferase (neo) gene (Beck, et al., Gene, 19:327-36, 1982), then cells that have taken up the LTVEC can be selected in G418-containing media; cells that do not have the LTVEC will die whereas cells that have taken up the LTVEC will survive (Santerre, et al., Gene, 30:147-56, 1984). Other suitable selectable markers include any drug that has activity in eukaryotic cells, such as hygromycin B (Santerre, et al., Gene, 30:147-56, 1984; Bernard, et al., Exp Cell Res, 158:237-43, 1985; Giordano and McAllister, Gene, 88:285-8, 1990), Blasticidin S (Izumi, et al., Exp Cell Res, 197: 229-33, 1991), and other which are familiar to those skilled in the art.

Step 6.

Screen for homologous recombination events in eukaryotic cells using quantitative assay for modification of allele (MOA). Eukaryotic cells that have been successfully modified by targeting the LTVEC into the locus of interest can be identified using a variety of approaches that can detect modification of allele within the locus of interest and that do not depend on assays spanning the entire homology arm or arms. Such approaches can include but are not limited to: (a) quantitative PCR using TAQMAN® (Lie and Petropoulos, Curr Opin Biotechnol, 9:43-8, 1998); (b) quantitative MOA assay using molecular beacons (Tan, et al., Chemistry, 6:1107-11, 2000); (c) fluorescence in situ hybridization FISH (Laan, et al., Hum Genet, 96:275-80, 1995) or comparative genomic hybridization (CGH) (Forozan, et al., Trends Genet, 13:405-9, 1997; Thompson and Gray, J Cell Biochem Suppl, 13943, 1993; Houldsworth and Chaganti, Am J Pathol, 145:1253-60, 1994); (d) isothermic DNA amplification (Lizardi et al., Nat Genet, 19:225-32, 1998; Mitra and Church, Nucleic Acids Res, 27:e34, 1999); and (e) quantitative hybridization to an immobilized probe(s) (Southern, J. Mol. Biol. 98: 503, 1975; Kafatos et al., Nucleic Acids Res 7(6):1541-52, 1979).

Applicants provide herein an example in which TAQMAN® quantitative PCR is used to screen for successfully targeted eukaryotic cells. For example, TAQMAN® is used to identify eukaryotic cells which have undergone homologous recombination wherein a portion of one of two endogenous alleles in a diploid genome has been replaced by another sequence. In contrast to traditional methods, in which a difference in restriction fragment length spanning the entire homology arm or arms indicates the modification of one of two alleles, the quantitative TAQMAN® method will detect the modification of one allele by measuring the reduction in copy number (by half) of the unmodified allele. Specifically, the probe detects the unmodified allele and not the modified allele. Therefore, the method is independent of the exact nature of the modification and not limited to the sequence replacement described in this example. TAQMAN® is used to quantify the number of copies of a DNA template in a genomic DNA sample, especially by comparison to a reference gene (Lie and Petropoulos, Curr. Opin. Biotechnol., 9:43-8, 1998). The reference gene is quantitated in the same genomic DNA as the target gene(s) or locus (loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus (loci) which is replaced by successful targeting. The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus (loci) has been replaced by homologous recombination will result in an increase of one Ct for the target TAQMAN® reaction without an increase in the Ct for the reference gene when compared to DNA from non-targeted cells. This allows for ready detection of the modification of one allele of the gene(s) of interest in eukaryotic cells using LTVECs.

As stated above, modification of allele (MOA) screening is the use of any method that detects the modification of one allele to identify cells which have undergone homologous recombination. It is not a requirement that the targeted alleles be identical (homologous) to each other, and in fact, they may contain polymorphisms, as is the case in progeny resulting from crossing two different strains of mice. In addition, one special situation that is also covered by MOA screening is targeting of genes which are normally present as a single copy in cells, such as some of the located on the sex chromosomes and in particular, on the Y chromosome. In this case, methods that will detect the modification of the single targeted allele, such as quantitative PCR, Southern blottings, etc., can be used to detect the targeting event. It is clear that the method of the invention can be used to generate modified eukaryotic cells even when alleles are polymorphic or when they are present in a single copy in the targeted cells.

Step 8.

Uses of genetically modified eukaryotic cells. (a) The genetically modified eukaryotic cells generated by the methods described in steps 1 through 7 can be employed in any in vitro or in vivo assay, where changing the phenotype of the cell is desirable. (b) The genetically modified eukaryotic cell generated by the methods described in steps 1 through 7 can also be used to generate an organism carrying the genetic modification. The genetically modified organisms can be generated by several different techniques including but not limited to: 1. Modified embryonic stem (ES) cells such as the frequently used rat and mouse ES cells. ES cells can be used to create genetically modified rats or mice by standard blastocyst injection technology or aggregation techniques (Robertson, Practical Approach Series, 254, 1987; Wood, et al., Nature, 365:87-9, 1993; Joyner supra), tetraploid blastocyst injection (Wang, et al., Mech Dev, 62:137-45, 1997), or nuclear transfer and cloning (Wakayama, et al., Proc Natl Acad Sci USA, 96:14984-9, 1999). ES cells derived from other organisms such as rabbits (Wang, et al., Mech Dev, 62:137-45, 1997; Schoonjans, et al., Mol Reprod Dev, 45:439-43, 1996) or chickens (Pain, et al., Development, 122:2339-48, 1996) or other species should also be amenable to genetic modification(s) using the methods of the invention. 2. Modified protoplasts can be used to generate genetically modified plants (for example see U.S. Pat. No. 5,350,689 "Zea mays plants and transgenic Zea mays plants regenerated from protoplasts or protoplast-derived cells", and U.S. Pat. No. 5,508,189 "Regeneration of plants from cultured guard cell protoplasts" and references therein). 3. Nuclear transfer from modified eukaryotic cells to oocytes to generate cloned organisms with modified allele (Wakayama, et al., Proc Natl Acad Sci USA, 96:14984-9, 1999; Baguisi, et al., Nat Biotechnol, 17:456-61, 1999; Wilmut, et al., Reprod Fertil Dev, 10:639-43, 1998; Wilmut, et al., Nature, 385:810-3, 1997; Wakayama, et al., Nat Genet, 24:108-9, 2000; Wakayama, et al., Nature, 394:369-74, 1998; Rideout, et al., Nat Genet, 24:109-10, 2000; Campbell, et al., Nature, 380:64-6, 1996). 4. Cell-fusion to transfer the modified allele to another cell, including transfer of engineered chromosome(s), and uses of such cell(s) to generate organisms carrying the modified allele or engineered chromosome(s) (Kuroiwa, et al., Nat Biotechnol, 18:1086-1090, 2000). 5. The method of the invention are also amenable to any other approaches that have been used or yet to be discovered.

While many of the techniques used in practicing the individual steps of the methods of the invention are familiar to the skilled artisan, Applicants contend that the novelty of the method of the invention lies in the unique combination of those steps and techniques coupled with the never-before-described method of introducing a LTVEC directly into eukaryotic cells to modify a chromosomal locus, and the use of quantitative MOA assays to identify eukaryotic cells which have been appropriately modified. This novel combination represents a significant improvement over previous technologies for creating organisms possessing modifications of endogenous genes or chromosomal loci.

EXAMPLES

Example 1. Engineering Mouse ES Cells Bearing a Deletion of the OCR10 Gene a. Selection of a Large Genomic DNA Clone Containing mOCR10.

Figure 2:
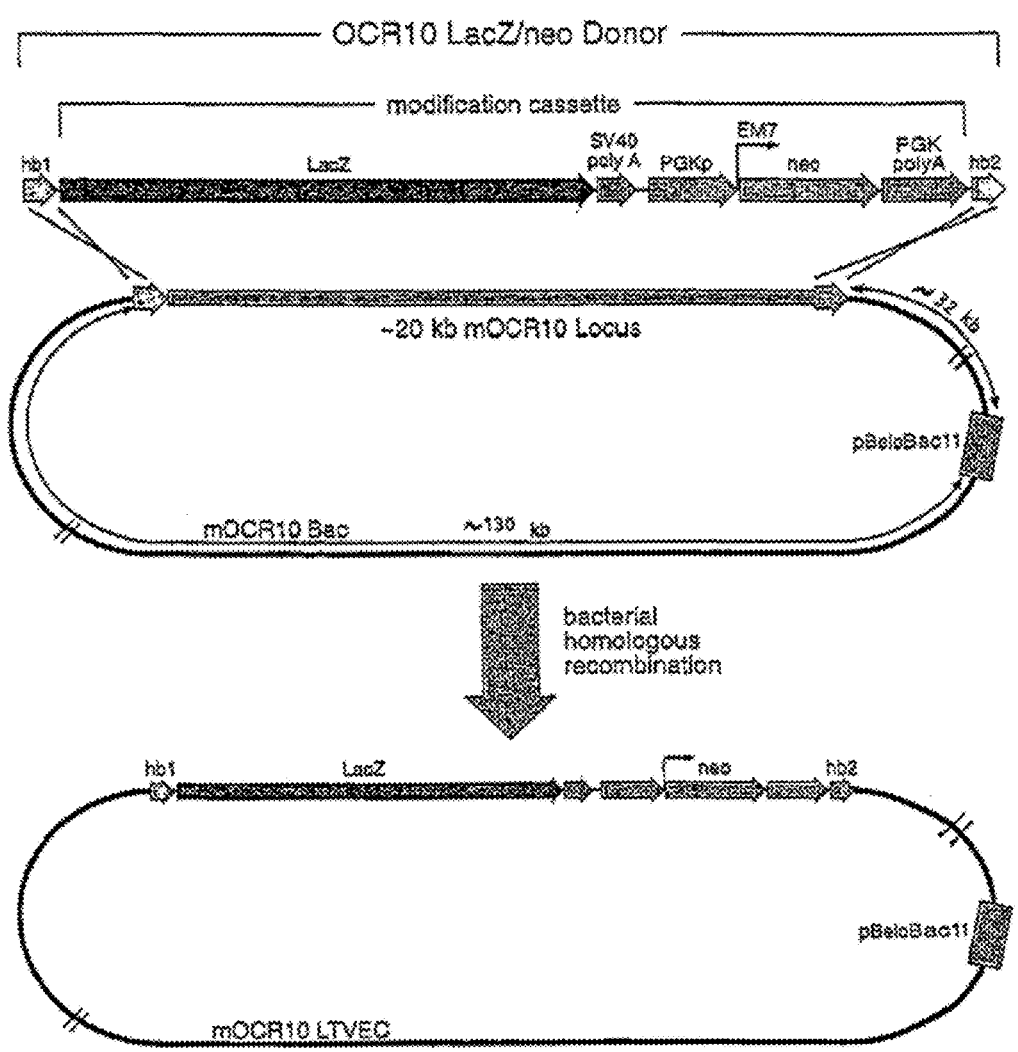
FIG. 2: Schematic diagram of donor fragment and LTVEC for mouse OCR10. (hb1=homology box 1; lacZ=β-galactosidase ORF; SV40 polyA=a DNA fragment derived from Simian Virus 40, containing a polyadenylation site and signal; PGKp=mouse phosphoglycerate kinase (PGK) promoter; EM7=a bacterial promoter; neo=neomycin phosphotransferase; PGK polyA=3' untranslated region derived from the PGK gene and containing a polyadenylation site and signal; hb2=homology box 2)

A Bacterial Artificial Chromosome (BAC) clone carrying a large genomic DNA fragment that contained the coding sequence of the mouse OCR10 (mOCR10) gene was obtained by screening an arrayed mouse genomic DNA BAC library (Incyte Genomics) using PCR. The primers employed to screen this library were derived from the mOCR10 gene cDNA sequence. Two primer pairs where used: (a) OCR10.RAA (SEQ ID NO: 1) and OCR10.PVIrc (SEQ ID NO: 2) which amplifies a 102 bp DNA; and (b) OCR10.TDY (SEQ ID NO: 3)) and OCR10.QETrc (SEQ ID NO: 4)) which amplifies a 1500 bp DNA. This mOCR10 BAC contained approximately 180 kb of genomic DNA including the complete mOCR10 coding sequence. This BAC clone was used to generate an LTVEC which was subsequently used to delete a portion of the coding region of mOCR10 while simultaneously introducing a reporter gene whose initiation codon precisely replaced the initiation codon of OCR10, as well as insertion of a selectable marker gene useful for selection both in *E. coli* and mammalian cells following the reporter gene (FIG. 2). The reporter gene (LacZ), encodes the *E. coli* β-galactosidase enzyme. Because of the position of insertion of LacZ (its initiating codon is at the same position as the initiation codon of mOCR10) the expression of lacZ should mimic that of mOCR10, as has been observed in other examples where similar replacements with LacZ were performed using previous technologies (see "Gene trap strategies in ES cells", by W Wurst and A. Gossler, in Joyner supra). The LacZ gene allows for a simple and standard enzymatic assay to be performed that can reveal its expression patterns in situ, thus providing a surrogate assay that reflects the normal expression patterns of the replaced gene(s) or chromosomal locus (loci).

b. Construction of Donor Fragment and Generation of LTVEC.

The modification cassette used in the construction of the mOCR10 LTVEC is the lacZ-SV40 polyA-PGKp-EM7-neo-PGK polyA cassette wherein lacZ is a marker gene as described above, SV40 polyA is a fragment derived from Simian Virus 40 (Subramanian, et al., Prog Nucleic Acid Res Mol Biol, 19:157-64, 1976; Thimmappaya, et al., J Biol Chem, 253:1613-8, 1978; Dhar, et al., Proc Natl Acad Sci USA, 71:371-5, 1974; Reddy, et al., Science, 200:494-502, 1978) and containing a polyadenylation site and signal (Subramanian, et al., Prog Nucleic Acid Res Mol Biol, 19:157-64, 1976; Thimmappaya, et al., J Biol Chem, 253: 1613-8, 1978; Dhar, et al., Proc Natl Acad Sci USA, 71:371-5, 1974; Reddy, et al., Science, 200:494-502, 1978), PGKp is the mouse phosphoglycerate kinase (PGK) promoter (Adra, et al., Gene, 60:65-74, 1987) (which has been used extensively to drive expression of drug resistance genes in mammalian cells), EM7 is a strong bacterial promoter that has the advantage of allowing for positive selection in bacteria of the completed LTVEC construct by driving expression of the neomycin phosphotransferase (neo) gene, neo is a selectable marker that confers Kanamycin resistance in prokaryotic cells and G418 resistance in eukaryotic cells (Beck, et al., Gene, 19:327-36, 1982), and PGK polyA is a 3' untranslated region derived from the PGK gene and containing a polyadenylation site and signal (Boer, et al., Biochem Genet, 28:299-308, 1990).

To construct the mOCR10 LTVEC, first a donor fragment was generated consisting of a mOCR10 homology box 1 (hb1) attached upstream from the LacZ gene in the modification cassette and a mOCR10 homology box 2 (hb2) attached downstream of the neo-PGK polyA sequence in the modification cassette (FIG. 2), using standard recombinant genetic engineering technology. Homology box 1 (hb1) consists of 211 bp of untranslated sequence immediately upstream of the initiating methionine of the mOCR10 open reading frame (mOCR10 ORF) (FIG. 3A-3D). Homology box 2 (hb2) consists of last 216 bp of the mOCR10 ORF, ending at the stop codon (FIG. 3A-3D).

Subsequently, using bacterial homologous recombination (Zhang, et al. supra; Angrand, et al., supra; Muyrers, et al. supra; Narayanan et al. supra; Yu et al. supra), this donor fragment was used to precisely replace the mOCR10 coding region (from initiation methionine to stop codon) with the insertion cassette, resulting in construction of the mOCR10 LTVEC (FIG. 2). Thus, in this mOCR10 LTVEC, the mOCR10 coding sequence was replaced by the insertion cassette creating an approximately 20 kb deletion in the mOCR10 locus while leaving approximately 130 kb of upstream homology (upstream homology arm) and 32 kb of downstream homology (downstream homology arm).

It is important to note that LTVECs can be more rapidly and conveniently generated from available BAC libraries than targeting vectors made using previous technologies because only a single bacterial homologous recombination step is required and the only sequence information required is that needed to generate the homology boxes. In contrast, previous approaches for generating targeting vectors using bacterial homologous recombination require that large targeting vectors be "trimmed" prior to their introduction in ES cells (Hill et al., Genomics, 64:111-3, 2000). This trimming is necessary because of the need to generate homology arms short enough to accommodate the screening methods utilized by previous approaches. One major disadvantage of the method of Hill et al. is that two additional homologous recombination steps are required simply for trimming (one to trim the region upstream of the modified locus and one to trim the region downstream of the modified locus). To do this, substantially more sequence information is needed, including sequence information spanning the sites of trimming.

In addition, another obvious advantage, illustrated by the above example, is that a very large deletion spanning the mOCR10 gene (approximately 20 kb) can be easily generated in a single step. In contrast, using previous technologies, to accomplish the same task may require several steps and may involve marking the regions upstream and downstream of the coding sequences with loxP sites in order to use the Cre recombinase to remove the sequence flanked by these sites after introduction of the modified locus in eukaryotic cells. This may be unattainable in one step, and thus may require the construction of two targeting vectors using different selection markers and two sequential targeting events in ES cells, one to introduce the loxP site at the region upstream of the coding sequence and another to introduce the loxP site at the region downstream of the coding sequence. It should be further noted that the creation of large deletions often occurs with low efficiency using the previous targeting technologies in eukaryotic cells, because the frequency of achieving homologous recombination may be low when using targeting vectors containing large deletion flanked by relatively short homology arms. The high efficiency obtained using the method of the invention (see below) is due to the very long homology arms present in the LTVEC that increase the rate of homologous recombination in eukaryotic cells.

c. Verification, Preparation, and Introduction of mOCR10 LTVEC DNA into ES Cells.

The sequence surrounding the junction of the insertion cassette and the homology sequence was verified by DNA sequencing. The size of the mOCR10 LTVEC was verified by restriction analysis followed by pulsed field gel electrophoresis (PFGE) (Cantor, et al., Annu Rev Biophys Biophys Chem, 17:287-304, 1988; Schwartz and Cantor, Cell, 37:67-75, 1984). A standard large-scale plasmid preparation of the mOCR10 LTVEC was done, the plasmid DNA was digested with the restriction enzyme NotI, which cuts in the vector backbone of the mOCR10 LTVEC, to generate linear DNA. Subsequently the linearized DNA was introduced into mouse ES cells by electroporation (Robertson, Practical Approach Series, 254, 1987; Joyner supra; Sambrook, et al. supra). ES cells successfully transfected with the mOCR10 LTVEC were selected for in G418-containing media using standard selection methods.

d. Identification of Targeted ES Cells Clones Using a Quantitative Modification of Allele (MOA) Assay.

To identify ES cells in which one of the two endogenous mOCR10 genes had been replaced by the modification cassette sequence, DNA from individual ES cell clones was analyzed by quantitative PCR using standard TAQMAN® methodology as described (Applied Biosystems, TAQMAN® Universal PCR Master Mix, catalog number P/N 4304437). The primers and TAQMAN® probes used are as described in FIG. 3A-3D (SEQ ID NO:5-6). A total of 69 independent ES cells clones where screened and 3 were identified as positive, i.e. as clones in which one of the endogenous mOCR10 coding sequence had been replaced by the modification cassette described above.

Several advantages of the MOA approach are apparent: (i) It does not require the use of a probe outside the locus being modified, thus obviating the need to know the sequence flanking the modified locus. (ii) It requires very little time to perform compared to conventional Southern blot methodology which has been the previous method of choice, thus reducing the time for identifying correctly modified cells from the typical several days to just a few hours. This is a significant improvement in the way screening has been performed in the past and makes it a much less labor-intensive and more cost-effective approach to screening for homologous recombination events in eukaryotic cells. Yet another advantage of the method of the invention is that it is also superior to previous technologies because of its ability to target difficult loci. Using previous technologies, it has been shown that for certain loci the frequency of successful targeting may by as low as 1 in 2000 integration events, perhaps even lower. Using the method of the invention, Applicants have demonstrated that such difficult loci can be targeted much more efficiently using LTVECs that contain long homology arms (i.e. greater than those allowed by previous technologies). As the non-limiting example described above demonstrates, the Applicants have targeted the OCR10 locus, a locus that has previously proven recalcitrant to targeting using conventional technology. Using the method of the invention, Applicants have shown that they have obtained successful targeting in 3 out of 69 ES cells clones in which the mOCR10 LTVEC (containing more than 160 kb of homology arms, and introducing a 20 kb deletion) had integrated, whereas using previous technology for ES cell targeting using a plasmid-based vector with homology arms shorter than 10-20 kb while also introducing a deletion of less than 15 kb, no targeted events were identified among more than 600 integrants of the vector. These data clearly demonstrate the superiority of the method of the invention over previous technologies.

Example 2. Increased Targeting Frequency and Abrogation of the Need to Use Isogenic DNA when LTVECs are used as the Targeting Vectors As noted above, the increased targeting frequency obtained using long homology arms should diminish the benefit, if any, derived from using genomic DNA in constructing LTVECs that is isogenic with (i.e. identical in sequence to) the DNA of the eukaryotic cell being targeted. To test this hypothesis, Applicants have constructed numerous LTVECs using genomic DNA derived from the same mouse substrain as the eukaryotic cell to be targeted (presumably isogenic), and numerous other LTVECs using genomic DNA derived from mouse substrains differing from that of the eukaryotic cell to be targeted (presumably non-isogenic). The two sets of LTVECs exhibited similar targeting frequencies, ranging from 1-13%, indicating that the rate of successful targeting using LTVECs does not depend on isogenicity.

The approach of creating LTVECs and directly using them as targeting vectors combined with MOA screening for homologous recombination events in ES cells creates a novel method for engineering genetically modified loci that is rapid, inexpensive and represents a significant improvement over the tedious, time-consuming methods previously in use. It thus opens the possibility of a rapid large scale in vivo functional genomics analysis of essentially any and all genes in an organism's genome in a fraction of the time and cost necessitated by previous methodologies.

Example 3. Use of LTVECs to Produce Chimeric and Human Antibodies a. Introduction.

The rearrangement of variable region genes during the initial development of B cells is the primary mechanism whereby the immune system produces antibodies capable of recognizing the huge number of antigens that it may encounter. Essentially, through DNA rearrangements during B cell development, a huge repertoire of variable (V) region sequences are assembled which are subsequently joined to a constant (C) region to produce complete heavy and light chains which assemble to form an antibody. After functional antibodies have been assembled, somatic hypermutation which occurs in the secondary lymphoid organs, introduces further diversity which enables the organism to select and optimize the affinity of the antibody.

The production of antibodies to various antigens in non-human species initially provided great promise for the large scale production of antibodies that could be used as human therapeutics. Species differences, however, leads to the production of antibodies by humans which inactivate the foreign antibodies and cause allergic reactions. Attempts were subsequently made to "humanize" the antibodies, thus making them less likely to be recognized as foreign in humans. Initially, this process involved combining the antigen binding portions of antibodies derived from mice with the constant region of human antibodies, thereby creating recombinant antibodies that were less immunogenic in humans. A second approach which was developed was phage display, whereby human V regions are cloned into a phage display library and regions with the appropriate binding characteristics are joined to human constant regions to create human antibodies. This technology is limited, however, by the lack of antibody development and affinity maturation which naturally occurs in B cells.

More recently, endogenous genes have been knocked out of mice, and the genes replaced with their human counterparts to produce entirely human antibodies. Unfortunately, the use of these constructs has highlighted the importance of an endogenous constant region in the development and optimization of antibodies in B cells. Human antibodies produced by transgenic mice with entirely human constructs have reduced affinity as compared to their mouse counterparts. Accordingly, the much acclaimed methods of producing humanized antibodies in mice and other organisms, wherein endogenous variable and constant regions of the mice are knocked out and replaced with their human counterparts, has not resulted in optimal antibodies.

The use of chimeric antibodies, which utilize human variable regions with mouse constant regions through B cell maturation, followed by subsequent engineering of the antibodies to replace the mouse constant regions with their human counterparts, has been suggested (U.S. Pat. No. 5,770,429). However, the only methodology that has existed to date for making such chimeras has been trans-switching, wherein the formation of the chimeras is only a rare event which occurs only in heavy chains. Heretofore, there has been no mechanism to produce, in transgenic animals, large scale replacement of the entire variable gene encoding segments with human genes, thereby producing chimeras in both the heavy and light chains. Utilizing Applicants' technology, as disclosed herein, chimeric antibodies are generated which can then be altered, through standard technology, to create high affinity human antibodies.

b. Brief Description.

A transgenic mouse is created that produces hybrid antibodies containing human variable regions and mouse constant regions. This is accomplished by a direct, in situ replacement of the mouse variable region genes with their human counterparts. The resultant hybrid immunoglobulin loci will undergo the natural process of rearrangements during B-cell development to produce the hybrid antibodies.

Subsequently, fully-human antibodies are made by replacing the mouse constant regions with the desired human counterparts. This approach will give rise to therapeutic antibodies much more efficiently than previous methods, e.g. the "humanization" of mouse monoclonal antibodies or the generation of fully human antibodies in HUMAB™ mice. Further, this method will succeed in producing therapeutic antibodies for many antigens for which previous methods have failed. This mouse will create antibodies that are human variable region-mouse constant region, which will have the following benefits over the previously available HUMAB™ mice that produce totally human antibodies. Antibodies generated by the new mouse will retain murine Fc regions which will interact more efficiently with the other components of the mouse B cell receptor complex, including the signaling components required for appropriate B cell differentiation (such as Iga and Igb). Additionally, the murine Fc regions will be more specific than human Fc regions in their interactions with Fc receptors on mouse cells, complement molecules, etc. These interactions are important for a strong and specific immune response, for the proliferation and maturation of B cells, and for the affinity maturation of antibodies.

Because there is a direct substitution of the human V-D-J/V-J regions for the equivalent regions of the mouse loci all of the sequences necessary for proper transcription, recombination, and/or class switching will remain intact. For example, the murine immunoglobulin heavy chain intronic enhancer, Em, has been shown to be critical for V-D-J recombination as well as heavy chain gene expression during the early stages of B cell development (Ronai et al. Mol Cell Biol 19:7031-7040 (1999)], whereas the immunoglobulin heavy chain 3' enhancer region appears to be critical for class switching (Pan et al. Eur J Immunol 30:1019-1029 (2000)) as well as heavy chain gene expression at later stages of B cell differentiation (Ong, et al. J Immunol 160:4896-4903 (1998)). Given these various, yet crucial, functions of the transcriptional control elements, it is desirable to maintain these sequences intact.

The required recombination events, which occur at the immunoglobulin loci during the normal course of B cell differentiation, may increase the frequency of aberrant, non-productive immunoglobulin rearrangements when these loci are inserted at improper chromosomal locations, or in multiple copies, as in currently available mice. With reductions in productive immunoglobulin rearrangement and, therefore, appropriate signaling at specific steps of B cell development the aberrant cells are eliminated. Reductions of B cell numbers at early stages of development significantly decreases the final overall B cell population and greatly limits the immune responses of the mice. Since there will be only one, chimeric, heavy or light chain locus (as opposed to mutated immunoglobulin loci and with human transgenic loci integrated at distinct chromosomal locations for heavy and light chains in the currently available mice) there should be no trans-splicing or trans-rearrangements of the loci which could result in non-productive rearrangements or therapeutically irrelevant chimeric antibodies (Willers et al. Immunobiology 200:150-164 (2000); Fujieda et al. J. Immunol. 157:3450-3459 (1996)).

The substitutions of the human V-D-J or V-J regions into the genuine murine chromosomal immunoglobulin loci should be substantially more stable, with increased transmission rates to progeny and decreased mosaicism of B cell genotypes compared with the currently available mice (Tomizuka at al Proc Natl Acad Sci (USA) 97:722-727 (2000)). Furthermore, introduction of the human variable regions at the genuine murine loci in vivo will maintain the appropriate global regulation of chromatin accessibility previously shown to be important for appropriately timed recombination events (Haines et al. Eur J Immunol 28:4228-4235 (1998)).

Approximately ⅓ of human antibodies contain lambda light chains, as compared to mice in which only ¹/₂₀ of murine antibodies contain lambda light chains. Therefore, replacing murine lambda light chain V-J sequences with lambda light chain V-J sequences derived from the human locus will serve to increase the repertoire of antibodies as well as more closely match the genuine human immune response, thus increasing the likelihood of obtaining therapeutically useful antibodies.

An additional benefit of integrating the human sequences into the genuine murine immunoglobulin loci is that no novel integration sites are introduced which might give rise to mutagenic disruptions at the insertion site and preclude the isolation of viable homozygous mice. This will greatly simplify the production and maintenance of a breeding mouse colony.

c. Materials and Methods:

Precise replacement of the mouse heavy chain locus variable region (VDJ) with its human counterpart is exemplified using a combination of homologous and site-specific recombination in the following example, which utilizes a two step process. One skilled in the art will recognize that replacement of the mouse locus with the homologous or orthologous human locus may be accomplished in one or more steps. Accordingly, the invention contemplates replacement of the murine locus, in whole or in part, with each integration via homologous recombination.

Figure 4A:
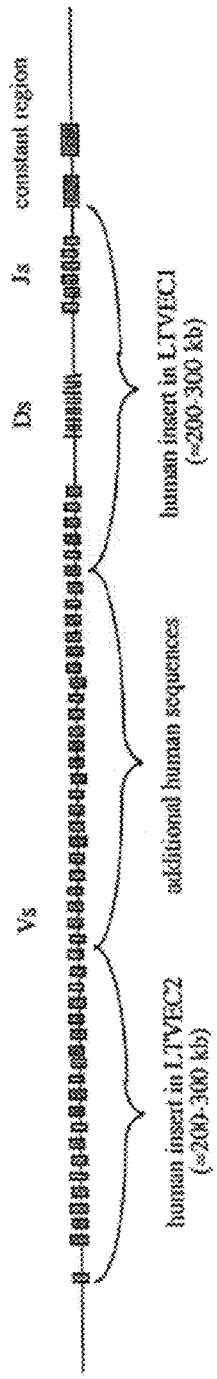
FIG. 4A-4D: (SEQ ID NO: 5-6) Schematic diagram of the two LTVECs constructed to replace the mouse VDJ region with human VDJ region. A: Large insert (BAC) clones spanning the entire VDJ region of the human heavy chain locus are isolated. B: In this example, large insert (BAC) clones are isolated from the ends of the mouse VDJ region as a source of homology arms which are used to direct integration via homologous recombination of the human VDJ sequences in a two step process. C-D: In the first step, LTVEC1 is constructed by bacterial homologous recombination in E. coli. LTVEC1 contains, in order: a large mouse homology arm derived from the region upstream from the mouse DJ region, but whose absolute endpoints are not important; a cassette encoding a selectable marker functional in ES cells (PGK-neomycinR); a loxP site; a large human insert spanning from several V gene segments through the entire DJ region; and a mouse homology arm containing the region immediately adjacent to, but not including, the mouse J segments. In the second step, LTVEC2 is constructed by bacterial homologous recombination in E. coli. LTVEC2 contains, in order: a large mouse homology arm containing the region adjacent to the most distal mouse V gene segment, but not containing any mouse V gene segments; a large insert containing a large number of distal human V gene segments; a mutant loxP site called lox511 in the orientation opposite to that of the wild type loxP sites in LTVEC2 and LTVEC1 (this site will not recombine with wild type loxP sites but will readily recombine with other lox511 sites); a wild type loxP site; a second selectable marker (PGK-hygromycinR); and a mouse homology arm derived from the V region, but whose absolute endpoints are not important.
Figure 4B:
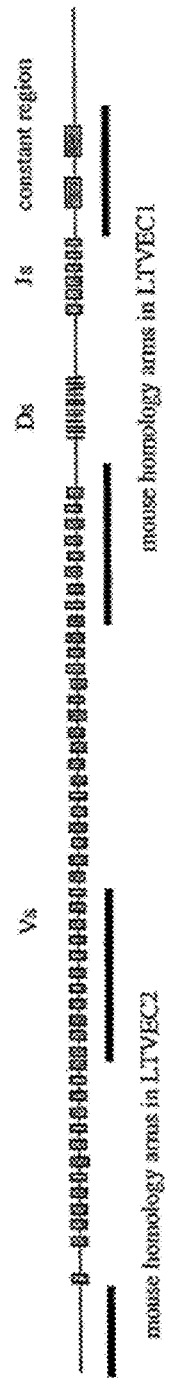

Large insert (BAC) clones spanning the entire VDJ region of the human heavy chain locus are isolated (FIG. 4A). The sequence of this entire region is available in the following GenBank files (AB019437, AB019438, AB019439, AB019440, AB019441, X97051 and X54713). In this example, large insert (BAC) clones are isolated from the ends of the mouse VDJ region as a source of homology arms (FIG. 4B) which are used to direct integration via homologous recombination of the human VDJ sequences in a two step process.

Figure 4C:
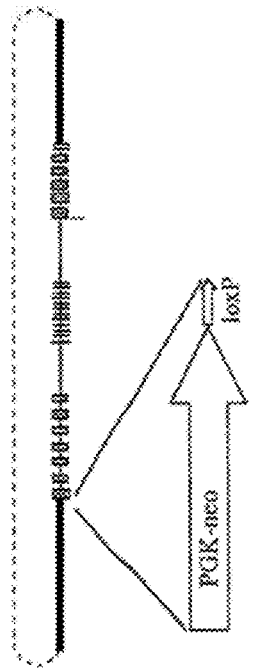
Figure 4D:
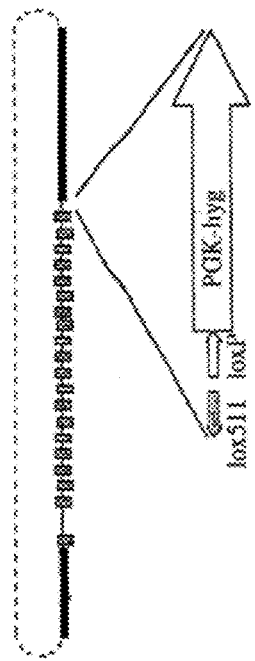

In the first step, LTVEC1 (FIG. 4D) is constructed by bacterial homologous recombination in *E. coli*. LTVEC1 contains, in order: a large mouse homology arm derived from the region upstream from the mouse DJ region, but whose absolute endpoints are not important; a cassette encoding a selectable marker functional in ES cells (PGK-neomycinR); a loxP site; a large human insert spanning from several V gene segments through the entire DJ region; and a mouse homology arm containing the region immediately adjacent to, but not including, the mouse J segments. Mouse ES cells will be transformed by standard techniques, for example, electroporation, with linearized LTVEC1, and neomycin resistant colonies will be screened for correct targeting using a MOA assay. These targeted ES cells can give rise to mice that produce antibodies with hybrid heavy chains.

However, it will be preferable to proceed with subsequent steps that will eliminate the remainder of the mouse variable segments.

In the second step, LTVEC2 (FIG. 4C) is constructed by bacterial homologous recombination in *E. coli*. LTVEC2 contains, in order: a large mouse homology arm containing the region adjacent to the most distal mouse V gene segment, but not containing any mouse V gene segments; a large insert containing a large number of distal human V gene segments; a mutant loxP site called lox511 (Hoess et al. Nucleic Acids Res. 14:2287-2300 (1986)), in the orientation opposite to that of the wild type loxP sites in LTVEC2 and LTVEC1 (this site will not recombine with wild type loxP sites but will readily recombine with other lox511 sites); a wild type loxP site; a second selectable marker (PGK-hygromycinR); and a mouse homology arm derived from the V region, but whose absolute endpoints are not important. Mouse ES cells that were correctly targeted with LTVEC1 will then be transformed by standard techniques with linearized LTVEC2, and hygromycin resistant colonies will be screened for correct targeting using a MOA assay. Correctly targeted ES cells resulting from this transformation will hereafter be referred to as "double targeted ES cells".

Subsequent transient expression of CRE recombinase in the double targeted ES cells will result in deletion of the remainder of the mouse V region. Alternatively, the double targeted ES cells can be injected into host blastocysts for the production of chimeric mice. Breeding of the resultant chimeric mice with mice expressing CRE recombinase early in development will result in deletion of the remainder of the mouse V region in the progeny F1. This later alternative increases the likelihood that the hybrid heavy chain locus will be passed through the germline because it involves culturing the ES cells for fewer generations.

The inclusion of lox511 in LTVEC2 will allow for the insertion of additional human V gene segments into the hybrid locus. One approach would be to use bacterial homologous recombination to flank a large genomic DNA clone containing many additional human V gene segments with lox511 and loxP sites. Co-transformation of such a modified large genomic DNA clone into double targeted ES cells with a plasmid that transiently expresses CRE recombinase will result in the introduction of the additional V gene segments by cassette exchange (Bethke et al. Nucleic Acids Res. 25:2828-2834 (1997)).

A second approach to the incorporation of additional V gene segments is to independently target a large genomic DNA clone containing many additional human V gene segments into the mouse locus using, for instance, the same mouse homology arms included in LTVEC2. In this case, the additional human V gene segments would be flanked by lox511 and loxP sites, and the targeted ES cells would be used to create a mouse. The mice derived from double targeted ES cells and the mice derived from the ES cells containing the additional V gene segments would be bred with a third mouse that directs expression of CRE recombinase during meiosis. The close proximity of the two recombinant loci during meiotic pairing would result in a high frequency of CRE induced inter-chromosomal recombination as has been seen in other systems (Herault et al. Nature Genetics 20: 381-384 (1998)).

The final steps in creating the human variable/mouse constant monoclonal antibody producing-mouse will be performing the equivalent variable region substitutions on the lambda and kappa light chain loci and breeding all three hybrid loci to homozygocity together in the same mouse. The resultant transgenic mouse will have a genome comprising entirely human heavy and light chain variable gene loci operably linked to entirely endogenous mouse constant region such that the mouse produces a serum containing an antibody comprising a human variable region and a mouse constant region in response to antigenic stimulation. Such a mouse may then be used as a source of DNA encoding the variable regions of human antibodies. Using standard recombinant technology, DNA encoding the variable regions of the heavy and light chains of the antibody is operably linked to DNA encoding the human heavy and light chain constant regions in cells, such as a CHO cells, which are capable of expressing active antibodies. The cells are grown under the appropriate conditions to express the fully human antibodies, which are then recovered. Variable region encoding sequences may be isolated, for example, by PCR amplification or cDNA cloning. In a preferred embodiment, hybridomas made from transgenic mice comprising some or all of the human variable region immunoglobulin loci (Kohler et al. Eur. J. Immunol., 6:511-519 (1976) are used as a source of DNA encoding the human variable regions.

We claim:

1. A method of producing a nucleic acid encoding a human immunoglobulin heavy chain variable region, the method comprising:
   (a) providing a transgenic mouse whose genome comprises in its germline unrearranged human immunoglobulin heavy chain V, D, and J gene segments, wherein the unrearranged human immunoglobulin heavy chain V, D, and J gene segments in situ replace endogenous mouse immunoglobulin heavy chain V, D, and J gene segments, and the unrearranged human immunoglobulin heavy chain V, D, and J gene segments are operably linked to an endogenous mouse heavy chain constant region gene, wherein the mouse heavy chain constant region gene is located at an endogenous mouse immunoglobulin heavy chain constant region locus, wherein rearrangement of the unrearranged human immunoglobulin heavy chain V, D, and J gene segments in the mouse results in a rearranged immunoglobulin human heavy chain variable region gene linked to the mouse heavy chain constant region gene, wherein the mouse in response to an antigen produces a hybrid antibody that comprises a human immunoglobulin heavy chain variable region encoded by the rearranged human immunoglobulin heavy chain variable region gene and a mouse heavy chain constant region encoded by the mouse heavy chain constant region gene;
   (b) stimulating an immune response in the mouse by exposing the mouse to an antigen;
   (c) preparing a hybridoma expressing the hybrid antibody from the spleen of the mouse stimulated by the antigen in step (b); and
   (d) isolating DNA encoding the human immunoglobulin heavy chain variable region of the hybrid antibody from the hybridoma of step (c).

2. The method of claim 1, wherein mouse V gene segments are present upstream of the unrearranged human immunoglobulin heavy chain V, D, and J gene segments.

3. The method of claim 1, wherein the endogenous immunoglobulin enhancer Eµ remains intact upstream of the mouse heavy chain constant region gene.

4. The method of claim 3, wherein mouse V gene segments are present upstream of the unrearranged human immunoglobulin heavy chain V, D, and J gene segments.

5. The method of claim 1, wherein the DNA encoding the human immunoglobulin heavy chain variable region of the antibody is isolated in step (d) by PCR amplification or cDNA cloning.

6. A method of producing a nucleic acid encoding a human immunoglobulin heavy chain variable region, the method comprising:
(a) providing a transgenic mouse whose genome comprises in its germline unrearranged human immunoglobulin heavy chain V, D, and J gene segments, wherein the unrearranged human immunoglobulin heavy chain V, D, and J gene segments in situ replace endogenous mouse immunoglobulin heavy chain V, D, and J gene segments, and the unrearranged human immunoglobulin heavy chain V, D, and J gene segments are operably linked to an endogenous mouse heavy chain constant region gene, wherein the mouse heavy chain constant region gene is located at an endogenous mouse immunoglobulin heavy chain constant region locus, wherein rearrangement of the unrearranged human immunoglobulin heavy chain V, D, and J gene segments in the mouse results in a rearranged human immunoglobulin heavy chain gene linked to the mouse heavy chain constant region gene, wherein the mouse in response to an antigen produces a hybrid antibody that comprises a human immunoglobulin heavy chain variable region encoded by the rearranged human immunoglobulin heavy chain variable region gene and a mouse heavy chain constant region encoded by the mouse heavy chain constant region gene;
(b) stimulating an immune response in the mouse by exposing the mouse to an antigen; and
(c) isolating DNA encoding the human immunoglobulin heavy chain variable region of the hybrid antibody from the mouse stimulated by with the antigen in step (b).

7. The method of claim 6, wherein mouse V gene segments are present upstream of the unrearranged human immunoglobulin heavy chain V, D, and J gene segments.

8. The method of claim 6, wherein the endogenous immunoglobulin enhancer Eμ remains intact upstream of the mouse heavy chain constant region gene.

9. The method of claim 8, wherein mouse V gene segments are present upstream of the unrearranged human heavy chain V, D, and J gene segments.

10. The method of claim 6, wherein the DNA encoding the human heavy chain variable region of the antibody is isolated in step (c) by PCR amplification or cDNA cloning.

* * * * *